(12) United States Patent
Chang

(10) Patent No.: US 11,248,058 B2
(45) Date of Patent: Feb. 15, 2022

(54) CHIMERIC ANTIGEN RECEPTORS AND USES THEREOF

(71) Applicant: University of Florida Research Foundation, Incorporated, Gainesville, FL (US)

(72) Inventor: Lung-Ji Chang, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 431 days.

(21) Appl. No.: 15/552,071

(22) PCT Filed: Feb. 19, 2016

(86) PCT No.: PCT/US2016/018716
§ 371 (c)(1),
(2) Date: Aug. 18, 2017

(87) PCT Pub. No.: WO2016/134284
PCT Pub. Date: Aug. 25, 2016

(65) Prior Publication Data
US 2018/0142034 A1 May 24, 2018

Related U.S. Application Data

(60) Provisional application No. 62/165,836, filed on May 22, 2015, provisional application No. 62/152,792, filed on Apr. 24, 2015, provisional application No. 62/134,444, filed on Mar. 17, 2015, provisional application No. 62/118,080, filed on Feb. 19, 2015.

(51) Int. Cl.
| | | |
|---|---|---|
| C07K 16/30 | (2006.01) |
| C07K 14/705 | (2006.01) |
| C07K 14/715 | (2006.01) |
| C07K 16/28 | (2006.01) |
| A61K 39/00 | (2006.01) |
| A61P 35/00 | (2006.01) |
| C07K 14/725 | (2006.01) |
| C12N 15/85 | (2006.01) |

(52) U.S. Cl.
CPC ...... *C07K 16/3076* (2013.01); *A61K 39/0011* (2013.01); *A61K 39/001112* (2018.08); *A61K 39/001171* (2018.08); *A61P 35/00* (2018.01); *C07K 14/7051* (2013.01); *C07K 14/70517* (2013.01); *C07K 14/70521* (2013.01); *C07K 14/70578* (2013.01); *C07K 14/7155* (2013.01); *C07K 16/2803* (2013.01); *C07K 16/2878* (2013.01); *C07K 16/3084* (2013.01); *C12N 15/85* (2013.01); *A61K 2039/5156* (2013.01); *A61K 2039/5158* (2013.01); *C07K 2317/24* (2013.01); *C07K 2317/565* (2013.01); *C07K 2317/622* (2013.01); *C07K 2317/73* (2013.01); *C07K 2319/00* (2013.01); *C07K 2319/03* (2013.01); *C12N 2740/15043* (2013.01)

(58) Field of Classification Search
None
See application file for complete search history.

(56) References Cited

U.S. PATENT DOCUMENTS

| | | | |
|---|---|---|---|
| 9,089,520 B2 | 7/2015 | Brenner | |
| 10,117,932 B2 | 11/2018 | Shultz et al. | |
| 10,647,778 B2 | 5/2020 | Chang | |
| 2005/0113564 A1 | 5/2005 | Campana et al. | |
| 2013/0280220 A1* | 10/2013 | Ahmed | C12N 15/85 424/93.21 |
| 2014/0301993 A1* | 10/2014 | Powell, Jr. | C07K 14/7051 424/93.21 |
| 2014/0322183 A1 | 10/2014 | Milone et al. | |
| 2015/0023937 A1 | 1/2015 | Vera Valdes et al. | |
| 2015/0118252 A1 | 4/2015 | Ho et al. | |
| 2015/0329640 A1 | 11/2015 | Finer | |
| 2016/0046724 A1 | 2/2016 | Brogdon et al. | |
| 2016/0058857 A1 | 3/2016 | Spencer et al. | |
| 2017/0137515 A1 | 5/2017 | Chang et al. | |
| 2017/0226216 A1 | 8/2017 | Morgan et al. | |
| 2018/0022815 A1 | 1/2018 | Chang | |
| 2019/0153109 A1 | 5/2019 | Rivkees et al. | |

FOREIGN PATENT DOCUMENTS

| | | |
|---|---|---|
| WO | WO 2012/033885 A1 | 3/2012 |
| WO | WO 2012/058460 A2 | 5/2012 |
| WO | WO 2013/074916 A1 | 5/2013 |
| WO | WO 2013/123061 A1 | 8/2013 |
| WO | WO 2013/126729 A1 | 8/2013 |
| WO | WO 2014/039523 A1 | 3/2014 |
| WO | WO 2014/055771 A1 | 4/2014 |
| WO | WO 2014/124143 A1 | 8/2014 |
| WO | WO 2014/055657 A1 | 10/2014 |

(Continued)

OTHER PUBLICATIONS

Gill et al (EOBT, 14(1):37-49, 2014).*

(Continued)

*Primary Examiner* — Brad Duffy
(74) *Attorney, Agent, or Firm* — Wolf, Greenfield & Sacks, P.C.

(57) ABSTRACT

Provided herein are chimeric antigen receptors (CARs) comprising an antigen binding domain (e.g., CD19, CD30, GD2, etc.), transmembrane domain (e.g., CD28), and a cytoplasmic domain (e.g., CD27, 4-1BB, etc.). In some aspects, the disclosure relates to use of the CARs in T cells, compositions, kits and methods.

7 Claims, 54 Drawing Sheets

Specification includes a Sequence Listing.

(56) References Cited

FOREIGN PATENT DOCUMENTS

| WO | WO 2014/165707 A2 | 10/2014 |
|---|---|---|
| WO | WO 2015/142675 A2 | 9/2015 |
| WO | WO 2015/179801 A1 | 11/2015 |
| WO | WO 2016/130598 A1 | 8/2016 |

OTHER PUBLICATIONS

International Search Report and Written Opinion dated May 20, 2016 for Application No. PCT/US2016/017219.
International Preliminary Report on Patentability dated Aug. 24, 2017 for Application No. PCT/US2016/017219.
International Search Report and Written Opinion dated Jun. 17, 2016 for Application No. PCT/US2016/018716.
International Preliminary Report on Patentability dated Aug. 31, 2017 for Application No. PCT/US2016/018716.
International Search Report and Written Opinion dated Sep. 14, 2015 for Application No. PCT/US2015/032245.
International Preliminary Report on Patentability dated Dec. 8, 2016 for Application No. PCT/US2015/032245.
International Search Report and Written Opinion dated Sep. 6, 2017 for Application No. PCT/US2017/030279.
International Preliminary Report on Patentability dated Nov. 8, 2018 for Application No. PCT/US2017/030279.
Supplementary European Search Report dated Jun. 12, 2018 for Application No. EP 16749750.2.
Partial Supplementary European Search Report dated Jul. 27, 2018 for Application No. EP 16753166.4.
Supplementary European Search Report dated Nov. 6, 2018 for Application No. EP 16753166.4.
Callahan et al., At the bedside: CTLA-4- and PD-1-blocking antibodies in cancer immunotherapy. J Leukoc Biol. Jul. 2013;94(1):41-53. doi: 10.1189/jlb.1212631. Epub May 10, 2013.
Di Stasi et al., Inducible Apoptosis as a Safety Switch for Adoptive Cell Therapy. The New England Journal of Medicine. Nov. 3, 2011;365(18):1673-83.
Gargett et al., The inducible caspase-9 suicide gene system as a "safety switch" to limit on-target, off-tumor toxicities of chimeric antigen receptor T cells. Frontiers in Pharmacology. Oct. 2014;5:1-7.
GENBANK Submission; "AAAT18_RS09785 hypothetical protein [Rhodococcus aetherivorans]", Gene ID: 29568086, updated on Apr. 20, 2017. 2 pages.
GENBANK Submission; NIH/NCBI, Accession No. NP_001183.2: " TNFRSF17 TNF receptor superfamily member 17[*Homo sapiens*]", Gene ID: 608. Last updated on Sep. 30, 2018. 5 pages.
GENBANK Submission; NIH/NCBI, Accession No. NP_002988.2: "syndecan-1 precursor [*Homo sapiens*]", Nov. 5, 2002. 2 pages.
Heczey et al., Invariant NKT cells with chimeric antigen receptor provide a novel platform for safe and effective cancer immunotherapy. Blood. Oct. 30, 2014;124(18):2824-33. doi: 10.1182/blood-2013-11-541235. Epub Jul. 21, 2014.
Highfill et al., Anti-PD1 Therapy for Pediatric Sarcomas. Retrieved from the Internet. http://sarcomahelp.org/research/immuntherapy-pediatric-sarcomas.html#tpm2_1. May 10, 2016.
Lee et al., The future is now: chimeric antigen receptors as new targeted therapies for childhood cancer. Clin Cancer Res. May 15, 2012;18(10):2780-90. doi: 10.1158/1078-0432.CCR-11-1920.
Novak et al., Expression of BCMA, TACI, and BAFF-R in multiple myeloma: a mechanism for growth and survival. Blood. Jan. 2004;103(2):689-694.
Prosser et al., Tumor PD-L1 co-stimulates primary human CD8(+) cytotoxic T cells modified to express a PD1:CD28 chimeric receptor. Mol Immunol. Jul. 2012;51(3-4):263-72. doi: 10.1016/j.molimm.2012.03.023. Epub Apr. 11, 2012.
Rappl et al., The CD3-Zeta Chimeric Antigen Receptor Overcomes TCR Hypo-Responsiveness of Human Terminal Late-Stage T Cells. PLoS One. 2012;7(1):e30713:1-10.
Sadelain et al., The Basic Principles of Chimeric Antigen Receptor Design. Cancer Discovery. Apr. 2013;3(4):388-98.
Sherbenou et al., The development of potential antibody-based therapies for myeloma. Blood Rev. Mar. 2015;29(2):81-91. doi: 10.1016/j.blre.2014.09.011. Epub Sep. 28, 2014.
Song et al., CD27 costimulation augments the survival and antitumor activity of redirected human T cells in vivo. Blood. Jan. 19, 2012;119(3):696-706. doi: 10.1182/blood-2011-03-344275. Epub Nov. 23, 2011.
Wu et al., The IL-15 receptor $\alpha$ chain cytoplasmic domain is critical for normal IL-15R $\alpha$ function but is not required for trans-presentation. Blood. Sep. 2008;112(12):4411-4419.
U.S. Appl. No. 15/549,961, filed Aug. 9, 2017, Chang.
U.S. Appl. No. 15/312,370, filed Nov. 18, 2016, Chang et al.
U.S. Appl. No. 16/097,437, filed Oct. 29, 2018, Rivkees et al.
EP 16749750.2, Jun. 12, 2018, Supplementary European Search Report.
PCT/US2016/017219, May 20, 2016, International Search Report and Written Opinion.
PCT/US2016/017219, Aug. 24, 2017, International Preliminary Report on Patentability.
EP 16753166.4, Jul. 27, 2018, Partial Supplementary European Search Report.
EP 16753166.4, Nov. 6, 2018, Supplementary European Search Report.
PCT/US2016/018716, Jun. 17, 2016, International Search Report and Written Opinion.
PCT/US2016/018716, Aug. 31, 2017, International Preliminary Report on Patentability.
PCT/US2015/032245, Sep. 14, 2015, International Search Report and Written Opinion.
PCT/US2015/032245, Dec. 8, 2016, International Preliminary Report on Patentability.
PCT/US2017/030279, Sep. 6, 2017, International Search Report and Written Opinion.
PCT/US2017/030279, Nov. 8, 2018, International Preliminary Report on Patentability.
Straathof et al., An inducible caspase 9 safety switch for T-cell therapy. Blood. Jun. 1, 2005;105(11):4247-54. doi: 10.1182/blood-2004-11-4564. Epub Feb. 22, 2005.

\* cited by examiner

19z CAR

273z CAR

ICOSz CAR

OX40z CAR

153z CAR

CD30-CAR T cells targeting primary CD30+ B lymphoma cells
Day 12 under fluorescent microscope GFP+ B lymphoma + control T

+ GD2-CAR T

+ 5F11 CD30-CAR T

+ AC10 CD30-CAR T

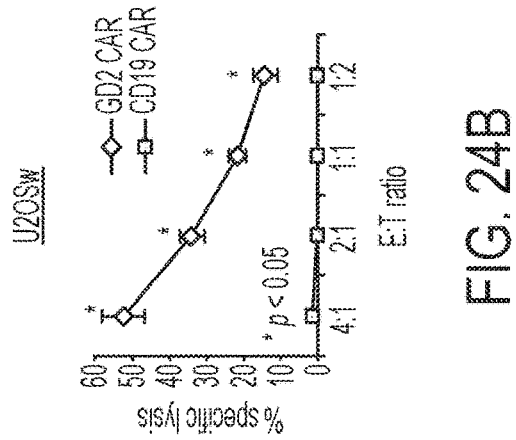
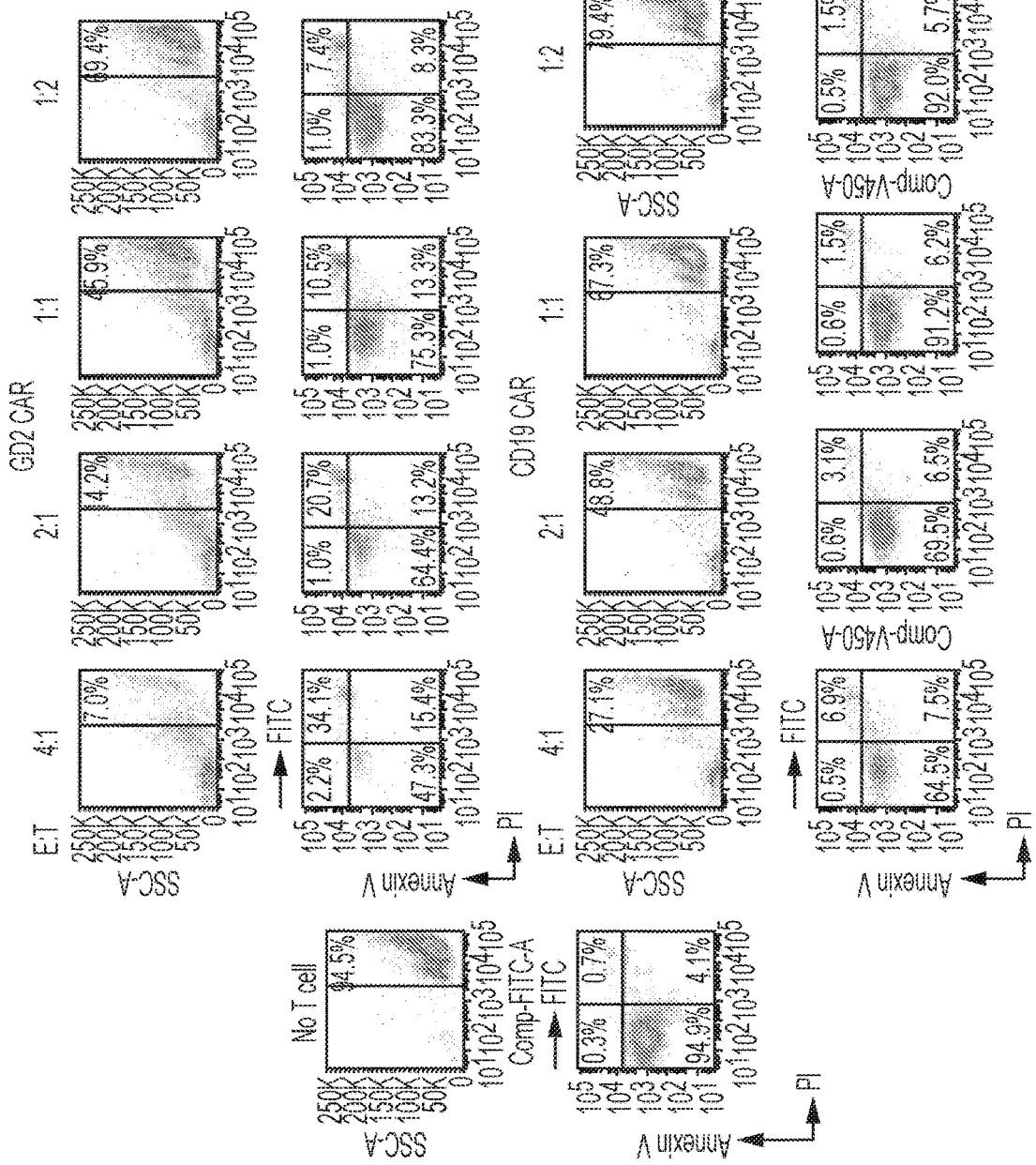
FIG. 24A
FIG. 24B

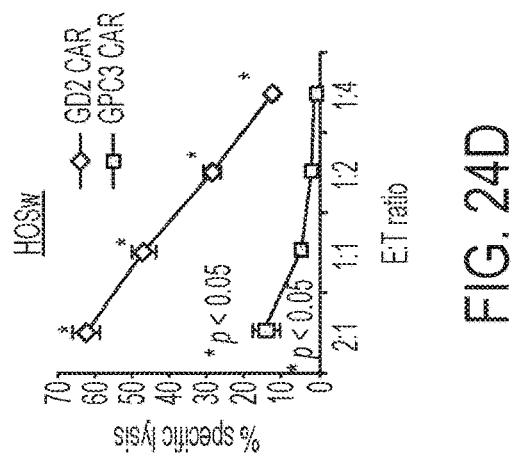
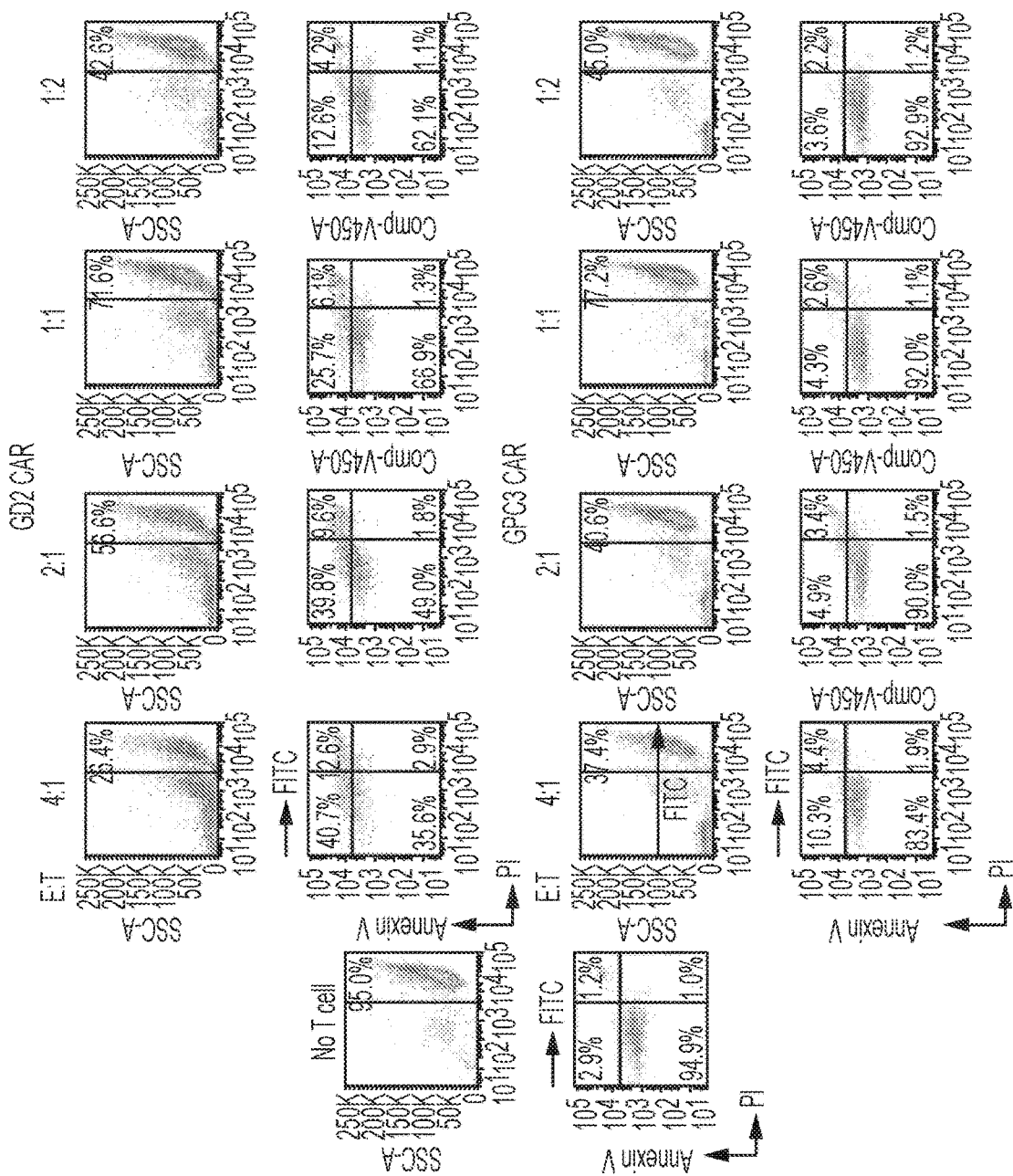
FIG. 24C
FIG. 24D

*Down-regulation of GD2 in RB tumor upon GD2-CAR T targeting*

SEQUENCE LISTING

```
<160> NUMBER OF SEQ ID NOS: 45

<210> SEQ ID NO 1
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 1

Gly Gly Gly Gly Ser
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 2

Gly Gly Gly Gly Ser Gly Gly Gly Gly Ser
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 4
```

```
Gly Ser Thr Ser Gly Gly Gly Ser Gly Gly Ser Gly Gly Gly
1               5                   10                  15

Ser Ser

<210> SEQ ID NO 5
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 5

Gly Ser Thr Ser Gly Ser Gly Lys Pro Gly Ser Ser Glu Gly Ser Thr
1               5                   10                  15

Lys Gly

<210> SEQ ID NO 6
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 6

Gly Gly Gly Gly Ser Gly Gly Gly
1               5

<210> SEQ ID NO 7
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 7

Val Glu Pro Lys Ser Cys Asp Lys Thr His Thr Cys Pro Pro Cys Pro
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 8

Leu Asp Pro Lys Ser Ser Asp Lys Thr His Thr Cys Pro Pro Cys Pro
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 9

Val Glu Pro Lys Ser Pro Asp Lys Thr His Thr Cys Pro Pro Cys Pro
1               5                   10                  15

<210> SEQ ID NO 10
<211> LENGTH: 11
<212> TYPE: PRT
<213> ORGANISM: Artificial Sequence
<220> FEATURE:
<223> OTHER INFORMATION: Synthetic Polypeptide
```

<400> SEQUENCE: 10

Leu Asp Lys Thr His Thr Cys Pro Pro Cys Pro
1               5                   10

<210> SEQ ID NO 11
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 11

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 12
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 12

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
            115                 120

<210> SEQ ID NO 13
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 13

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Trp Thr Phe Gly Gln Gly Thr Lys Val Glu Ile Lys
            100                 105                 110

<210> SEQ ID NO 14
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 14

Val His Gln Ile Gln Leu Val Gln Ser Gly Ala Glu Val Lys Lys Pro
1               5                   10                  15

Gly Ala Ser Val Lys Val Ser Cys Lys Ala Ser Gly Tyr Thr Phe Thr
            20                  25                  30

Asp Tyr Tyr Ile Thr Trp Val Arg Gln Ala Pro Gly Gln Gly Leu Glu
        35                  40                  45

Trp Met Gly Trp Ile Tyr Pro Gly Ser Gly Asn Thr Lys Tyr Asn Glu
    50                  55                  60

Lys Phe Lys Gly Arg Val Thr Met Thr Arg Asp Thr Ser Ile Ser Thr
65                  70                  75                  80

Ala Tyr Met Glu Leu Ser Arg Leu Arg Ser Asp Asp Thr Ala Val Tyr
                85                  90                  95

Tyr Cys Ala Asn Tyr Gly Asn Tyr Trp Phe Ala Tyr Trp Gly Gln Gly
            100                 105                 110

Thr Leu Val Thr Val Ser Ser
        115

<210> SEQ ID NO 15
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 15

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Thr Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asp Ser Tyr Pro Ile
                 85                  90                  95

Thr Phe Gly Gln Gly Thr Arg Leu Glu Ile Lys
            100                 105

<210> SEQ ID NO 16
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 16

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Ala Tyr
             20                  25                  30

Tyr Trp Ser Trp Ile Arg Gln Pro Pro Gly Lys Gly Leu Glu Trp Ile
         35                  40                  45

Gly Asp Ile Asn His Gly Gly Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Asn Ser Val Thr Ala Ala Asp Thr Ala Val Tyr Tyr Cys Ala
             85                  90                  95

Ser Leu Thr Ala Tyr Trp Gly Gln Gly Ser Leu Val Thr Val Ser Ser
            100                 105                 110

<210> SEQ ID NO 17
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 17

Gln Val Gln Leu Val Glu Ser Gly Pro Gly Val Val Gln Pro Gly Arg
 1               5                  10                  15

Ser Leu Arg Ile Ser Cys Ala Val Ser Gly Phe Ser Val Thr Asn Tyr
             20                  25                  30

Gly Val His Trp Val Arg Gln Pro Pro Gly Lys Gly Leu Glu Trp Leu
         35                  40                  45

Gly Val Ile Trp Ala Gly Gly Ile Thr Asn Tyr Asn Ser Ala Phe Met
 50                  55                  60

Ser Arg Leu Thr Ile Ser Lys Asp Asn Ser Lys Asn Thr Val Tyr Leu
 65                  70                  75                  80

Gln Met Asn Ser Leu Arg Ala Glu Asp Thr Ala Met Tyr Tyr Cys Ala
             85                  90                  95

Ser Arg Gly Gly His Tyr Gly Tyr Ala Leu Asp Tyr Trp Gly Gln Gly
            100                 105                 110

Thr Leu Val Thr Val Ser Ser
        115

<210> SEQ ID NO 18
<211> LENGTH: 104
<212> TYPE: PRT
<213> ORGANISM: Artificial Sequence
```

<220> FEATURE:
<223> OTHER INFORMATION: Synthetic Polypeptide

<400> SEQUENCE: 18

```
Glu Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn Asp
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Ser Gly Val Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys
            100
```

<210> SEQ ID NO 19
<211> LENGTH: 241
<212> TYPE: PRT
<213> ORGANISM: Artificial Sequence
<220> FEATURE:
<223> OTHER INFORMATION: Synthetic Polypeptide

<400> SEQUENCE: 19

```
Gln Val Gln Leu Val Glu Ser Gly Pro Gly Val Val Gln Pro Gly Arg
1               5                   10                  15

Ser Leu Arg Ile Ser Cys Ala Val Ser Gly Phe Ser Val Thr Asn Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ile Thr Asn Tyr Asn Ser Ala Phe Met
    50                  55                  60

Ser Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Met Tyr Tyr Cys Ala
                85                  90                  95

Ser Arg Gly Gly His Tyr Gly Tyr Ala Leu Asp Tyr Trp Gly Gln Gly
            100                 105                 110

Thr Leu Val Thr Val Ser Ser Gly Ser Thr Ser Gly Ser Gly Lys Pro
        115                 120                 125

Gly Ser Ser Glu Gly Ser Thr Lys Gly Glu Ile Val Met Thr Gln Thr
    130                 135                 140

Pro Ala Thr Leu Ser Val Ser Ala Gly Glu Arg Val Thr Ile Thr Cys
145                 150                 155                 160

Lys Ala Ser Gln Ser Val Ser Asn Asp Val Thr Trp Tyr Gln Gln Lys
                165                 170                 175

Pro Gly Gln Ala Pro Arg Leu Leu Ile Tyr Ser Ala Ser Asn Arg Tyr
            180                 185                 190

Ser Gly Val Pro Ala Arg Phe Ser Gly Ser Gly Tyr Gly Thr Glu Phe
        195                 200                 205

Thr Phe Thr Ile Ser Ser Val Gln Ser Glu Asp Phe Ala Val Tyr Phe
    210                 215                 220

Cys Gln Gln Asp Tyr Ser Ser Phe Gly Gln Gly Thr Lys Leu Glu Ile
```

-continued

```
225                 230                 235                 240
Lys

<210> SEQ ID NO 20
<211> LENGTH: 249
<212> TYPE: PRT
<213> ORGANISM: Artificial Sequence
<220> FEATURE:
<223> OTHER INFORMATION: Synthetic Polypeptide

<400> SEQUENCE: 20

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser Gly Ser Thr Gly Ser Gly Lys Pro
        115                 120                 125

Gly Ser Ser Glu Gly Ser Thr Lys Gly Asp Val Val Met Thr Gln Thr
    130                 135                 140

Pro Leu Ser Leu Pro Val Ser Leu Gly Asp Gln Ala Ser Ile Ser Cys
145                 150                 155                 160

Arg Ser Ser Gln Ser Leu Leu Lys Asn Asn Gly Asn Thr Phe Leu His
                165                 170                 175

Trp Tyr Leu Gln Lys Ser Gly Gln Ser Pro Lys Leu Leu Ile Tyr Lys
            180                 185                 190

Val Ser Asn Arg Leu Ser Gly Val Pro Asp Arg Phe Ser Gly Ser Gly
        195                 200                 205

Ser Gly Thr Tyr Phe Thr Leu Lys Ile Ser Arg Val Glu Ala Glu Asp
    210                 215                 220

Leu Gly Val Tyr Phe Cys Ser Gln Ser Thr His Ile Pro Tyr Thr Phe
225                 230                 235                 240

Gly Gly Gly Thr Lys Leu Glu Ile Lys
                245

<210> SEQ ID NO 21
<211> LENGTH: 244
<212> TYPE: PRT
<213> ORGANISM: Artificial Sequence
<220> FEATURE:
<223> OTHER INFORMATION: Synthetic Polypeptide

<400> SEQUENCE: 21

Glu Val Gln Leu Val Gln Ser Gly Ala Glu Val Glu Lys Pro Gly Ala
1               5                   10                  15

Ser Val Lys Ile Ser Cys Lys Ala Ser Gly Ser Ser Phe Thr Gly Tyr
            20                  25                  30

Asn Met Asn Trp Val Arg Gln Asn Ile Gly Lys Ser Leu Glu Trp Ile
```

```
            35                  40                  45
Gly Ala Ile Asp Pro Tyr Tyr Gly Gly Thr Ser Tyr Asn Gln Lys Phe
 50                  55                  60

Lys Gly Arg Ala Thr Leu Thr Val Asp Lys Ser Thr Ser Thr Ala Tyr
 65                  70                  75                  80

Met His Leu Lys Ser Leu Arg Ser Glu Asp Thr Ala Val Tyr Tyr Cys
                 85                  90                  95

Val Ser Gly Met Glu Tyr Trp Gly Gln Gly Thr Ser Val Thr Val Ser
                100                 105                 110

Ser Gly Ser Thr Ser Gly Ser Gly Lys Pro Gly Ser Ser Glu Gly Ser
                115                 120                 125

Thr Lys Gly Asp Val Val Met Thr Gln Thr Pro Leu Ser Leu Pro Val
130                 135                 140

Thr Pro Gly Glu Pro Ala Ser Ile Ser Cys Arg Ser Ser Gln Ser Leu
145                 150                 155                 160

Val His Arg Asn Gly Asn Thr Tyr Leu His Trp Tyr Leu Gln Lys Pro
                165                 170                 175

Gly Gln Ser Pro Lys Leu Leu Ile His Lys Val Ser Asn Arg Phe Ser
                180                 185                 190

Gly Val Pro Asp Arg Phe Ser Gly Ser Gly Ser Gly Thr Asp Phe Thr
                195                 200                 205

Leu Lys Ile Ser Arg Val Glu Ala Glu Asp Leu Gly Val Tyr Phe Cys
210                 215                 220

Ser Gln Ser Thr His Val Pro Pro Leu Thr Phe Gly Ala Gly Thr Lys
225                 230                 235                 240

Leu Glu Leu Lys

<210> SEQ ID NO 22
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 22

Tyr Val Asn Gln Thr Asp Ile Tyr Phe Cys Lys Ile Glu Val Met Tyr
 1               5                  10                  15

Pro Pro Pro Tyr Leu Asp Asn Glu Lys Ser Asn Gly Thr Ile Ile His
                20                  25                  30

Val Lys Gly Lys His Leu Cys Pro Ser Pro Leu Phe Pro Gly Pro Ser
                35                  40                  45

Lys Pro
 50

<210> SEQ ID NO 23
<211> LENGTH: 202
<212> TYPE: PRT
<213> ORGANISM: Artificial Sequence
<220> FEATURE:
<223> OTHER INFORMATION: Synthetic Polypeptide

<400> SEQUENCE: 23

Asn Lys Ile Leu Val Lys Gln Ser Pro Met Leu Val Ala Tyr Asp Asn
 1               5                  10                  15

Ala Val Asn Leu Ser Cys Lys Tyr Ser Tyr Asn Leu Phe Ser Arg Glu
                20                  25                  30

Phe Arg Ala Ser Leu His Lys Gly Leu Asp Ser Ala Val Glu Val Cys
```

```
                  35                  40                  45
Val Val Tyr Gly Asn Tyr Ser Gln Gln Leu Gln Val Tyr Ser Lys Thr
 50                  55                  60

Gly Phe Asn Cys Asp Gly Lys Leu Gly Asn Glu Ser Val Thr Phe Tyr
 65                  70                  75                  80

Leu Gln Asn Leu Tyr Val Asn Gln Thr Asp Ile Tyr Phe Cys Lys Ile
                 85                  90                  95

Glu Val Met Tyr Pro Pro Pro Tyr Leu Asp Asn Glu Lys Ser Asn Gly
                100                 105                 110

Thr Ile Ile His Val Lys Gly Lys His Leu Cys Pro Ser Pro Leu Phe
                115                 120                 125

Pro Gly Pro Ser Lys Pro Phe Trp Val Leu Val Val Val Gly Gly Val
                130                 135                 140

Leu Ala Cys Tyr Ser Leu Leu Val Thr Val Ala Phe Ile Ile Phe Trp
145                 150                 155                 160

Val Arg Ser Lys Arg Ser Arg Leu Leu His Ser Asp Tyr Met Asn Met
                165                 170                 175

Thr Pro Arg Arg Pro Gly Pro Thr Arg Lys His Tyr Gln Pro Tyr Ala
                180                 185                 190

Pro Pro Arg Asp Phe Ala Ala Tyr Arg Ser
                195                 200

<210> SEQ ID NO 24
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 24

Phe Trp Val Leu Val Val Val Gly Gly Val Leu Ala Cys Tyr Ser Leu
 1               5                  10                  15

Leu Val Thr Val Ala Phe Ile Ile Phe Trp Val
                20                  25

<210> SEQ ID NO 25
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 25

Ile Glu Val Met Tyr Pro Pro Pro Tyr Leu Asp Asn Glu Lys Ser Asn
 1               5                  10                  15

Gly Thr Ile Ile His Val Lys Gly Lys His Leu Cys Pro Ser Pro Leu
                20                  25                  30

Phe Pro Gly Pro Ser Lys Pro Phe Trp Val Leu Val Val Val Gly Gly
                35                  40                  45

Val Leu Ala Cys Tyr Ser Leu Leu Val Thr Val Ala Phe Ile Ile Phe
                50                  55                  60

Trp Val Arg Ser Lys Arg Ser Arg Leu Leu His Ser Asp Tyr Met Asn
 65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser Ala Ser
                100                 105
```

```
<210> SEQ ID NO 26
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 26

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

<210> SEQ ID NO 27
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 27

Lys Ser Arg Gln Thr Pro Pro Leu Ala Ser Val Glu Met Glu Ala Met
1               5                   10                  15

Glu Ala Leu Pro Val Thr Trp Gly Thr Ser Ser Arg Asp Glu Asp Leu
            20                  25                  30

Glu Asn Cys Ser His His Leu
        35

<210> SEQ ID NO 28
<211> LENGTH: 416
<212> TYPE: PRT
<213> ORGANISM: Artificial Sequence
<220> FEATURE:
<223> OTHER INFORMATION: Synthetic Polypeptide

<400> SEQUENCE: 28

Met Asp Glu Ala Asp Arg Arg Leu Leu Arg Arg Cys Arg Leu Arg Leu
1               5                   10                  15

Val Glu Glu Leu Gln Val Asp Gln Leu Trp Asp Ala Leu Leu Ser Arg
            20                  25                  30

Glu Leu Phe Arg Pro His Met Ile Glu Asp Ile Gln Arg Ala Gly Ser
        35                  40                  45

Gly Ser Arg Arg Asp Gln Ala Arg Gln Leu Ile Ile Asp Leu Glu Thr
    50                  55                  60

Arg Gly Ser Gln Ala Leu Pro Leu Phe Ile Ser Cys Leu Glu Asp Thr
65                  70                  75                  80

Gly Gln Asp Met Leu Ala Ser Phe Leu Arg Thr Asn Arg Gln Ala Ala
                85                  90                  95

Lys Leu Ser Lys Pro Thr Leu Glu Asn Leu Thr Pro Val Val Leu Arg
            100                 105                 110

Pro Glu Ile Arg Lys Pro Glu Val Leu Arg Pro Glu Thr Pro Arg Pro
        115                 120                 125

Val Asp Ile Gly Ser Gly Gly Phe Gly Asp Val Gly Ala Leu Glu Ser
    130                 135                 140

Leu Arg Gly Asn Ala Asp Leu Ala Tyr Ile Leu Ser Met Glu Pro Cys
145                 150                 155                 160

Gly His Cys Leu Ile Ile Asn Asn Val Asn Phe Cys Arg Glu Ser Gly
```

```
                165                 170                 175
Leu Arg Thr Arg Thr Gly Ser Asn Ile Asp Cys Glu Lys Leu Arg Arg
            180                 185                 190

Arg Phe Ser Ser Leu His Phe Met Val Glu Val Lys Gly Asp Leu Thr
        195                 200                 205

Ala Lys Lys Met Val Leu Ala Leu Leu Glu Leu Ala Gln Gln Asp His
    210                 215                 220

Gly Ala Leu Asp Cys Val Val Ile Leu Ser His Gly Cys Gln
225                 230                 235                 240

Ala Ser His Leu Gln Phe Pro Gly Ala Val Tyr Gly Thr Asp Gly Cys
                245                 250                 255

Pro Val Ser Val Glu Lys Ile Val Asn Ile Phe Asn Gly Thr Ser Cys
            260                 265                 270

Pro Ser Leu Gly Gly Lys Pro Lys Leu Phe Phe Ile Gln Ala Cys Gly
        275                 280                 285

Gly Glu Gln Lys Asp His Gly Phe Glu Val Ala Ser Thr Ser Pro Glu
    290                 295                 300

Asp Glu Ser Pro Gly Ser Asn Pro Glu Pro Asp Ala Thr Pro Phe Gln
305                 310                 315                 320

Glu Gly Leu Arg Thr Phe Asp Gln Leu Asp Ala Ile Ser Ser Leu Pro
                325                 330                 335

Thr Pro Ser Asp Ile Phe Val Ser Tyr Ser Thr Phe Pro Gly Phe Val
            340                 345                 350

Ser Trp Arg Asp Pro Lys Ser Gly Ser Trp Tyr Val Glu Thr Leu Asp
        355                 360                 365

Asp Ile Phe Glu Gln Trp Ala His Ser Glu Asp Leu Gln Ser Leu Leu
    370                 375                 380

Leu Arg Val Ala Asn Ala Val Ser Val Lys Gly Ile Tyr Lys Gln Met
385                 390                 395                 400

Pro Gly Cys Phe Asn Phe Leu Arg Lys Lys Leu Phe Phe Lys Thr Ser
                405                 410                 415

<210> SEQ ID NO 29
<211> LENGTH: 278
<212> TYPE: PRT
<213> ORGANISM: Artificial Sequence
<220> FEATURE:
<223> OTHER INFORMATION: Synthetic Polypeptide

<400> SEQUENCE: 29

Val Gly Ala Leu Glu Ser Leu Arg Gly Asn Ala Asp Leu Ala Tyr Ile
1               5                   10                  15

Leu Ser Met Glu Pro Cys Gly His Cys Leu Ile Ile Asn Asn Val Asn
            20                  25                  30

Phe Cys Arg Glu Ser Gly Leu Arg Thr Arg Thr Gly Ser Asn Ile Asp
        35                  40                  45

Cys Glu Lys Leu Arg Arg Arg Phe Ser Ser Leu His Phe Met Val Glu
    50                  55                  60

Val Lys Gly Asp Leu Thr Ala Lys Lys Met Val Leu Ala Leu Leu Glu
65                  70                  75                  80

Leu Ala Gln Gln Asp His Gly Ala Leu Asp Cys Cys Val Val Val Ile
                85                  90                  95

Leu Ser His Gly Cys Gln Ala Ser His Leu Gln Phe Pro Gly Ala Val
            100                 105                 110

Tyr Gly Thr Asp Gly Cys Pro Val Ser Val Glu Lys Ile Val Asn Ile
```

```
                  115                 120                 125
Phe Asn Gly Thr Ser Cys Pro Ser Leu Gly Gly Lys Pro Lys Leu Phe
    130                 135                 140

Phe Ile Gln Ala Cys Gly Gly Glu Gln Lys Asp His Gly Phe Glu Val
145                 150                 155                 160

Ala Ser Thr Ser Pro Glu Asp Glu Ser Pro Gly Ser Asn Pro Glu Pro
                165                 170                 175

Asp Ala Thr Pro Phe Gln Glu Gly Leu Arg Thr Phe Asp Gln Leu Asp
            180                 185                 190

Ala Ile Ser Ser Leu Pro Thr Pro Ser Asp Ile Phe Val Ser Tyr Ser
        195                 200                 205

Thr Phe Pro Gly Phe Val Ser Trp Arg Asp Pro Lys Ser Gly Ser Trp
    210                 215                 220

Tyr Val Glu Thr Leu Asp Asp Ile Phe Glu Gln Trp Ala His Ser Glu
225                 230                 235                 240

Asp Leu Gln Ser Leu Leu Leu Arg Val Ala Asn Ala Val Ser Val Lys
                245                 250                 255

Gly Ile Tyr Lys Gln Met Pro Gly Cys Phe Asn Phe Leu Arg Lys Lys
            260                 265                 270

Leu Phe Phe Lys Thr Ser
            275

<210> SEQ ID NO 30
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 30

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Val Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
            100                 105

<210> SEQ ID NO 31
<211> LENGTH: 527
<212> TYPE: PRT
<213> ORGANISM: Artificial Sequence
<220> FEATURE:
<223> OTHER INFORMATION: Synthetic Polypeptide

<400> SEQUENCE: 31

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30
```

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
    195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Ala Ala Ile Glu Val Met Tyr Pro Pro Pro Tyr
                245                 250                 255

Leu Asp Asn Glu Lys Ser Asn Gly Thr Ile Ile His Val Lys Gly Lys
            260                 265                 270

His Leu Cys Pro Ser Pro Leu Phe Pro Gly Pro Ser Lys Pro Phe Trp
    275                 280                 285

Val Leu Val Val Val Gly Gly Val Leu Ala Cys Tyr Ser Leu Leu Val
    290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
            340                 345                 350

Arg Ser Ala Ser Gly Gly Gly Gly Ser Gly Gly Gly Gly Ser Lys Ser
    355                 360                 365

Arg Gln Thr Pro Pro Leu Ala Ser Val Glu Met Glu Ala Met Glu Ala
    370                 375                 380

Leu Pro Val Thr Trp Gly Thr Ser Ser Arg Asp Glu Asp Leu Glu Asn
385                 390                 395                 400

Cys Ser His His Leu Gly Gly Gly Ser Gly Gly Gly Gly Gly Ser Arg
                405                 410                 415

Val Lys Phe Ser Arg Ser Ala Asp Ala Pro Ala Tyr Gln Gln Gly Gln
            420                 425                 430

Asn Gln Leu Tyr Asn Glu Leu Asn Leu Gly Arg Arg Glu Glu Tyr Asp
    435                 440                 445

Val Leu Asp Lys Arg Arg Gly Arg Asp Pro Glu Met Gly Gly Lys Pro

```
            450                 455                 460
Arg Arg Lys Asn Pro Gln Glu Gly Leu Tyr Asn Glu Leu Gln Lys Asp
465                 470                 475                 480

Lys Met Ala Glu Ala Tyr Ser Glu Ile Gly Met Lys Gly Glu Arg Arg
                485                 490                 495

Arg Gly Lys Gly His Asp Gly Leu Tyr Gln Gly Leu Ser Thr Ala Thr
                500                 505                 510

Lys Asp Thr Tyr Asp Ala Leu His Met Gln Ala Leu Pro Pro Arg
                515                 520                 525

<210> SEQ ID NO 32
<211> LENGTH: 906
<212> TYPE: PRT
<213> ORGANISM: Artificial Sequence
<220> FEATURE:
<223> OTHER INFORMATION: Synthetic Polypeptide

<400> SEQUENCE: 32

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Ala Tyr
                20                  25                  30

Tyr Trp Ser Trp Ile Arg Gln Pro Pro Gly Lys Gly Leu Glu Trp Ile
            35                  40                  45

Gly Asp Ile Asn His Gly Gly Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Ser Leu Thr Ala Tyr Trp Gly Gln Gly Ser Leu Val Thr Val Ser Ser
                100                 105                 110

Gly Ser Thr Ser Gly Ser Gly Lys Pro Gly Ser Ser Glu Gly Ser Thr
                115                 120                 125

Lys Gly Asp Ile Gln Met Thr Gln Ser Pro Thr Ser Leu Ser Ala Ser
        130                 135                 140

Val Gly Asp Arg Val Thr Ile Thr Cys Arg Ala Ser Gln Gly Ile Ser
145                 150                 155                 160

Ser Trp Leu Thr Trp Tyr Gln Gln Lys Pro Glu Lys Ala Pro Lys Ser
                165                 170                 175

Leu Ile Tyr Ala Ala Ser Ser Leu Gln Ser Gly Val Pro Ser Arg Phe
                180                 185                 190

Ser Gly Ser Gly Ser Gly Thr Asp Phe Thr Leu Thr Ile Ser Ser Leu
                195                 200                 205

Gln Pro Glu Asp Phe Ala Thr Tyr Tyr Cys Gln Gln Tyr Asp Ser Tyr
        210                 215                 220

Pro Ile Thr Phe Gly Gln Gly Thr Arg Leu Glu Ile Lys Gly Ser Thr
225                 230                 235                 240

Ser Gly Ser Gly Lys Pro Gly Ser Ser Glu Gly Ser Thr Lys Gly Phe
                245                 250                 255

Trp Val Leu Val Val Val Gly Gly Val Leu Ala Cys Tyr Ser Leu Leu
                260                 265                 270

Val Thr Val Ala Phe Ile Ile Phe Trp Val Lys Arg Gly Arg Lys Lys
                275                 280                 285

Leu Leu Tyr Ile Phe Lys Gln Pro Phe Met Arg Pro Val Gln Thr Thr
```

```
            290                 295                 300
Gln Glu Glu Asp Gly Cys Ser Cys Arg Phe Pro Glu Glu Glu Gly
305                 310                 315                 320

Gly Cys Glu Leu Gln Arg Arg Lys Tyr Arg Ser Asn Lys Gly Glu Ser
                325                 330                 335

Pro Val Glu Pro Ala Glu Pro Cys His Tyr Ser Cys Pro Arg Glu Glu
                340                 345                 350

Glu Gly Ser Thr Ile Pro Ile Gln Glu Asp Tyr Arg Lys Pro Glu Pro
            355                 360                 365

Ala Cys Ser Pro Gly Ser Thr Ser Gly Ser Gly Lys Pro Gly Ser Ser
        370                 375                 380

Glu Gly Ser Thr Lys Gly Arg Val Lys Phe Ser Arg Ser Ala Asp Ala
385                 390                 395                 400

Pro Ala Tyr Lys Gln Gly Gln Asn Gln Leu Tyr Asn Glu Leu Asn Leu
                405                 410                 415

Gly Arg Arg Glu Glu Tyr Asp Val Leu Asp Lys Arg Gly Arg Asp
                420                 425                 430

Pro Glu Met Gly Gly Lys Pro Arg Arg Lys Asn Pro Gln Glu Gly Leu
            435                 440                 445

Tyr Asn Glu Leu Gln Lys Asp Lys Met Ala Glu Ala Tyr Ser Glu Ile
        450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
                485                 490                 495

Gln Ala Leu Pro Pro Arg Gly Ser Thr Ser Gly Ser Gly Lys Pro Gly
            500                 505                 510

Ser Ser Glu Gly Ser Thr Lys Gly Val Gly Ala Leu Glu Ser Leu Arg
        515                 520                 525

Gly Asn Ala Asp Leu Ala Tyr Ile Leu Ser Met Glu Pro Cys Gly His
        530                 535                 540

Cys Leu Ile Ile Asn Asn Val Asn Phe Cys Arg Glu Ser Gly Leu Arg
545                 550                 555                 560

Thr Arg Thr Gly Ser Asn Ile Asp Cys Glu Lys Leu Arg Arg Arg Phe
                565                 570                 575

Ser Ser Leu His Phe Met Val Glu Val Lys Gly Asp Leu Thr Ala Lys
            580                 585                 590

Lys Met Val Leu Ala Leu Leu Glu Leu Ala Gln Gln Asp His Gly Ala
        595                 600                 605

Leu Asp Cys Cys Val Val Val Ile Leu Ser His Gly Cys Gln Ala Ser
610                 615                 620

His Leu Gln Phe Pro Gly Ala Val Tyr Gly Thr Asp Gly Cys Pro Val
625                 630                 635                 640

Ser Val Glu Lys Ile Val Asn Ile Phe Asn Gly Thr Ser Cys Pro Ser
                645                 650                 655

Leu Gly Gly Lys Pro Lys Leu Phe Phe Ile Gln Ala Cys Gly Gly Glu
            660                 665                 670

Gln Lys Asp His Gly Phe Glu Val Ala Ser Thr Ser Pro Glu Asp Glu
        675                 680                 685

Ser Pro Gly Ser Asn Pro Glu Pro Asp Ala Thr Pro Phe Gln Glu Gly
        690                 695                 700

Leu Arg Thr Phe Asp Gln Leu Asp Ala Ile Ser Ser Leu Pro Thr Pro
705                 710                 715                 720
```

```
Ser Asp Ile Phe Val Ser Tyr Ser Thr Phe Pro Gly Phe Val Ser Trp
            725                 730                 735

Arg Asp Pro Lys Ser Gly Ser Trp Tyr Val Glu Thr Leu Asp Asp Ile
        740                 745                 750

Phe Glu Gln Trp Ala His Ser Glu Asp Leu Gln Ser Leu Leu Leu Arg
            755                 760                 765

Val Ala Asn Ala Val Ser Val Lys Gly Ile Tyr Lys Gln Met Pro Gly
        770                 775                 780

Cys Phe Asn Phe Leu Arg Lys Lys Leu Phe Phe Lys Thr Ser Met Gly
785                 790                 795                 800

Val Gln Val Glu Thr Ile Ser Pro Gly Asp Gly Arg Thr Phe Pro Lys
            805                 810                 815

Arg Gly Gln Thr Cys Val Val His Tyr Thr Gly Met Leu Glu Asp Gly
        820                 825                 830

Lys Lys Val Asp Ser Ser Arg Asp Arg Asn Lys Pro Phe Lys Phe Met
            835                 840                 845

Leu Gly Lys Gln Glu Val Ile Arg Gly Trp Glu Glu Gly Val Ala Gln
    850                 855                 860

Met Ser Val Gly Gln Arg Ala Lys Leu Thr Ile Ser Pro Asp Tyr Ala
865                 870                 875                 880

Tyr Gly Ala Thr Gly His Pro Gly Ile Ile Pro Pro His Ala Thr Leu
            885                 890                 895

Val Phe Asp Val Glu Leu Leu Lys Leu Glu
            900                 905

<210> SEQ ID NO 33
<211> LENGTH: 1347
<212> TYPE: PRT
<213> ORGANISM: Artificial Sequence
<220> FEATURE:
<223> OTHER INFORMATION: Synthetic Polypeptide

<400> SEQUENCE: 33

Gln Val Gln Leu Val Glu Ser Gly Pro Gly Val Val Gln Pro Gly Arg
1               5                   10                  15

Ser Leu Arg Ile Ser Cys Ala Val Ser Gly Phe Ser Val Thr Asn Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ile Thr Asn Tyr Asn Ser Ala Phe Met
    50                  55                  60

Ser Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Met Tyr Tyr Cys Ala
            85                  90                  95

Ser Arg Gly Gly His Tyr Gly Tyr Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Ser Thr Ser Gly Ser Gly Lys Pro Gly Ser Ser Glu Gly Ser
    450                 455                 460

Thr Lys Gly Glu Ile Val Met Thr Gln Thr Pro Ala Thr Leu Ser Val
465                 470                 475                 480

Ser Ala Gly Glu Arg Val Thr Ile Thr Cys Lys Ala Ser Gln Ser Val
                485                 490                 495

Ser Asn Asp Val Thr Trp Tyr Gln Gln Lys Pro Gly Gln Ala Pro Arg
            500                 505                 510

Leu Leu Ile Tyr Ser Ala Ser Asn Arg Tyr Ser Gly Val Pro Ala Arg
        515                 520                 525

Phe Ser Gly Ser Gly Tyr Gly Thr Glu Phe Thr Phe Thr Ile Ser Ser
    530                 535                 540

Val Gln Ser Glu Asp Phe Ala Val Tyr Phe Cys Gln Gln Asp Tyr Ser
545                 550                 555                 560

Ser Phe Gly Gln Gly Thr Lys Leu Glu Ile Lys Arg Thr Val Ala Ala
                565                 570                 575

Pro Ser Val Phe Ile Phe Pro Pro Ser Asp Glu Gln Leu Lys Ser Gly
            580                 585                 590
```

```
Thr Ala Ser Val Val Cys Leu Leu Asn Asn Phe Tyr Pro Arg Glu Ala
            595                 600                 605
Lys Val Gln Trp Lys Val Asp Asn Ala Leu Gln Ser Gly Asn Ser Gln
610                 615                 620
Glu Ser Val Thr Glu Gln Asp Ser Lys Asp Ser Thr Tyr Ser Leu Ser
625                 630                 635                 640
Ser Thr Leu Thr Leu Ser Lys Ala Asp Tyr Glu Lys His Lys Val Tyr
            645                 650                 655
Ala Cys Glu Val Thr His Gln Gly Leu Ser Ser Pro Val Thr Lys Ser
                660                 665                 670
Phe Asn Arg Gly Glu Cys Gly Ser Thr Ser Gly Ser Gly Lys Pro Gly
            675                 680                 685
Ser Ser Glu Gly Ser Thr Lys Gly Phe Trp Val Leu Val Val Val Gly
            690                 695                 700
Gly Val Leu Ala Cys Tyr Ser Leu Leu Val Thr Val Ala Phe Ile Ile
705                 710                 715                 720
Phe Trp Val Lys Arg Gly Arg Lys Lys Leu Leu Tyr Ile Phe Lys Gln
                725                 730                 735
Pro Phe Met Arg Pro Val Gln Thr Thr Gln Glu Glu Asp Gly Cys Ser
                740                 745                 750
Cys Arg Phe Pro Glu Glu Glu Gly Gly Cys Glu Leu Gln Arg Arg
            755                 760                 765
Lys Tyr Arg Ser Asn Lys Gly Glu Ser Pro Val Glu Pro Ala Glu Pro
            770                 775                 780
Cys His Tyr Ser Cys Pro Arg Glu Glu Glu Gly Ser Thr Ile Pro Ile
785                 790                 795                 800
Gln Glu Asp Tyr Arg Lys Pro Glu Pro Ala Cys Ser Pro Gly Ser Thr
                805                 810                 815
Ser Gly Ser Gly Lys Pro Gly Ser Ser Glu Gly Ser Thr Lys Gly Arg
                820                 825                 830
Val Lys Phe Ser Arg Ser Ala Asp Ala Pro Ala Tyr Lys Gln Gly Gln
                835                 840                 845
Asn Gln Leu Tyr Asn Glu Leu Asn Leu Gly Arg Arg Glu Glu Tyr Asp
850                 855                 860
Val Leu Asp Lys Arg Arg Gly Arg Asp Pro Glu Met Gly Gly Lys Pro
865                 870                 875                 880
Arg Arg Lys Asn Pro Gln Glu Gly Leu Tyr Asn Glu Leu Gln Lys Asp
                885                 890                 895
Lys Met Ala Glu Ala Tyr Ser Glu Ile Gly Met Lys Gly Glu Arg Arg
                900                 905                 910
Arg Gly Lys Gly His Asp Gly Leu Tyr Gln Gly Leu Ser Thr Ala Thr
                915                 920                 925
Lys Asp Thr Tyr Asp Ala Leu His Met Gln Ala Leu Pro Pro Arg Gly
930                 935                 940
Ser Thr Ser Gly Ser Gly Lys Pro Gly Ser Ser Glu Gly Ser Thr Lys
945                 950                 955                 960
Gly Val Gly Ala Leu Glu Ser Leu Arg Gly Asn Ala Asp Leu Ala Tyr
                965                 970                 975
Ile Leu Ser Met Glu Pro Cys Gly His Cys Leu Ile Ile Asn Asn Val
                980                 985                 990
Asn Phe Cys Arg Glu Ser Gly Leu Arg Thr Arg Thr Gly Ser Asn Ile
                995                 1000                1005
Asp Cys Glu Lys Leu Arg Arg Arg Phe Ser Ser Leu His Phe Met
```

Val Glu Val Lys Gly Asp Leu Thr Ala Lys Met Val Leu Ala
    1025                1030                1035

Leu Leu Glu Leu Ala Gln Gln Asp His Gly Ala Leu Asp Cys Cys
    1040                1045                1050

Val Val Val Ile Leu Ser His Gly Cys Gln Ala Ser His Leu Gln
    1055                1060                1065

Phe Pro Gly Ala Val Tyr Gly Thr Asp Gly Cys Pro Val Ser Val
    1070                1075                1080

Glu Lys Ile Val Asn Ile Phe Asn Gly Thr Ser Cys Pro Ser Leu
    1085                1090                1095

Gly Gly Lys Pro Lys Leu Phe Phe Ile Gln Ala Cys Gly Gly Glu
    1100                1105                1110

Gln Lys Asp His Gly Phe Glu Val Ala Ser Thr Ser Pro Glu Asp
    1115                1120                1125

Glu Ser Pro Gly Ser Asn Pro Glu Pro Asp Ala Thr Pro Phe Gln
    1130                1135                1140

Glu Gly Leu Arg Thr Phe Asp Gln Leu Asp Ala Ile Ser Ser Leu
    1145                1150                1155

Pro Thr Pro Ser Asp Ile Phe Val Ser Tyr Ser Thr Phe Pro Gly
    1160                1165                1170

Phe Val Ser Trp Arg Asp Pro Lys Ser Gly Ser Trp Tyr Val Glu
    1175                1180                1185

Thr Leu Asp Asp Ile Phe Glu Gln Trp Ala His Ser Glu Asp Leu
    1190                1195                1200

Gln Ser Leu Leu Leu Arg Val Ala Asn Ala Val Ser Val Lys Gly
    1205                1210                1215

Ile Tyr Lys Gln Met Pro Gly Cys Phe Asn Phe Leu Arg Lys Lys
    1220                1225                1230

Leu Phe Phe Lys Thr Ser Met Gly Val Gln Val Glu Thr Ile Ser
    1235                1240                1245

Pro Gly Asp Gly Arg Thr Phe Pro Lys Arg Gly Gln Thr Cys Val
    1250                1255                1260

Val His Tyr Thr Gly Met Leu Glu Asp Gly Lys Lys Val Asp Ser
    1265                1270                1275

Ser Arg Asp Arg Asn Lys Pro Phe Lys Phe Met Leu Gly Lys Gln
    1280                1285                1290

Glu Val Ile Arg Gly Trp Glu Glu Gly Val Ala Gln Met Ser Val
    1295                1300                1305

Gly Gln Arg Ala Lys Leu Thr Ile Ser Pro Asp Tyr Ala Tyr Gly
    1310                1315                1320

Ala Thr Gly His Pro Gly Ile Ile Pro Pro His Ala Thr Leu Val
    1325                1330                1335

Phe Asp Val Glu Leu Leu Lys Leu Glu
    1340                1345

<210> SEQ ID NO 34
<211> LENGTH: 892
<212> TYPE: PRT
<213> ORGANISM: Artificial Sequence
<220> FEATURE:
<223> OTHER INFORMATION: Synthetic Polypeptide

<400> SEQUENCE: 34

Gln Val Gln Leu Val Glu Ser Gly Pro Gly Val Val Gln Pro Gly Arg

```
  1               5                   10                  15
Ser Leu Arg Ile Ser Cys Ala Val Ser Gly Phe Ser Val Thr Asn Tyr
                20                  25                  30
Gly Val His Trp Val Arg Gln Pro Pro Gly Lys Gly Leu Glu Trp Leu
                35                  40                  45
Gly Val Ile Trp Ala Gly Gly Ile Thr Asn Tyr Asn Ser Ala Phe Met
                50                  55                  60
Ser Arg Leu Thr Ile Ser Lys Asp Asn Ser Lys Asn Thr Val Tyr Leu
65                  70                  75                  80
Gln Met Asn Ser Leu Arg Ala Glu Asp Thr Ala Met Tyr Tyr Cys Ala
                85                  90                  95
Ser Arg Gly Gly His Tyr Gly Tyr Ala Leu Asp Tyr Trp Gly Gln Gly
                100                 105                 110
Thr Leu Val Thr Val Ser Gly Ser Thr Ser Gly Gly Lys Pro
                115                 120                 125
Gly Ser Ser Glu Gly Ser Thr Lys Gly Glu Ile Val Met Thr Gln Thr
130                 135                 140
Pro Ala Thr Leu Ser Val Ser Ala Gly Glu Arg Val Thr Ile Thr Cys
145                 150                 155                 160
Lys Ala Ser Gln Ser Val Ser Asn Asp Val Thr Trp Tyr Gln Gln Lys
                165                 170                 175
Pro Gly Gln Ala Pro Arg Leu Leu Ile Tyr Ser Ala Ser Asn Arg Tyr
                180                 185                 190
Ser Gly Val Pro Ala Arg Phe Ser Gly Ser Gly Tyr Gly Thr Glu Phe
                195                 200                 205
Thr Phe Thr Ile Ser Ser Val Gln Ser Glu Asp Phe Ala Val Tyr Phe
210                 215                 220
Cys Gln Gln Asp Tyr Ser Ser Phe Gly Gln Gly Thr Lys Leu Glu Ile
225                 230                 235                 240
Lys Phe Trp Val Leu Val Val Val Gly Val Leu Ala Cys Tyr Ser
                245                 250                 255
Leu Leu Val Thr Val Ala Phe Ile Ile Phe Trp Val Lys Arg Gly Arg
                260                 265                 270
Lys Lys Leu Leu Tyr Ile Phe Lys Gln Pro Phe Met Arg Pro Val Gln
                275                 280                 285
Thr Thr Gln Glu Glu Asp Gly Cys Ser Cys Arg Phe Pro Glu Glu Glu
                290                 295                 300
Glu Gly Gly Cys Glu Leu Gln Arg Arg Lys Tyr Arg Ser Asn Lys Gly
305                 310                 315                 320
Glu Ser Pro Val Glu Pro Ala Glu Pro Cys His Tyr Ser Cys Pro Arg
                325                 330                 335
Glu Glu Glu Gly Ser Thr Ile Pro Ile Gln Glu Asp Tyr Arg Lys Pro
                340                 345                 350
Glu Pro Ala Cys Ser Pro Gly Ser Thr Ser Gly Ser Gly Lys Pro Gly
                355                 360                 365
Ser Ser Glu Gly Ser Thr Lys Gly Arg Val Lys Phe Ser Arg Ser Ala
                370                 375                 380
Asp Ala Pro Ala Tyr Lys Gln Gly Gln Asn Gln Leu Tyr Asn Glu Leu
385                 390                 395                 400
Asn Leu Gly Arg Arg Glu Glu Tyr Asp Val Leu Asp Lys Arg Arg Gly
                405                 410                 415
Arg Asp Pro Glu Met Gly Gly Lys Pro Arg Arg Lys Asn Pro Gln Glu
                420                 425                 430
```

```
Gly Leu Tyr Asn Glu Leu Gln Lys Asp Lys Met Ala Glu Ala Tyr Ser
            435                 440                 445

Glu Ile Gly Met Lys Gly Glu Arg Arg Gly Lys Gly His Asp Gly
450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg Gly Ser Thr Ser Gly Ser Gly Lys
                485                 490                 495

Pro Gly Ser Ser Glu Gly Ser Thr Lys Gly Val Gly Ala Leu Glu Ser
                500                 505                 510

Leu Arg Gly Asn Ala Asp Leu Ala Tyr Ile Leu Ser Met Glu Pro Cys
            515                 520                 525

Gly His Cys Leu Ile Ile Asn Asn Val Asn Phe Cys Arg Glu Ser Gly
            530                 535                 540

Leu Arg Thr Arg Thr Gly Ser Asn Ile Asp Cys Glu Lys Leu Arg Arg
545                 550                 555                 560

Arg Phe Ser Ser Leu His Phe Met Val Glu Val Lys Gly Asp Leu Thr
                565                 570                 575

Ala Lys Lys Met Val Leu Ala Leu Leu Glu Leu Ala Gln Gln Asp His
            580                 585                 590

Gly Ala Leu Asp Cys Cys Val Val Ile Leu Ser His Gly Cys Gln
            595                 600                 605

Ala Ser His Leu Gln Phe Pro Gly Ala Val Tyr Gly Thr Asp Gly Cys
            610                 615                 620

Pro Val Ser Val Glu Lys Ile Val Asn Ile Phe Asn Gly Thr Ser Cys
625                 630                 635                 640

Pro Ser Leu Gly Gly Lys Pro Lys Leu Phe Phe Ile Gln Ala Cys Gly
                645                 650                 655

Gly Glu Gln Lys Asp His Gly Phe Glu Val Ala Ser Thr Ser Pro Glu
                660                 665                 670

Asp Glu Ser Pro Gly Ser Asn Pro Glu Pro Asp Ala Thr Pro Phe Gln
            675                 680                 685

Glu Gly Leu Arg Thr Phe Asp Gln Leu Asp Ala Ile Ser Ser Leu Pro
            690                 695                 700

Thr Pro Ser Asp Ile Phe Val Ser Tyr Ser Thr Phe Pro Gly Phe Val
705                 710                 715                 720

Ser Trp Arg Asp Pro Lys Ser Gly Ser Trp Tyr Val Glu Thr Leu Asp
                725                 730                 735

Asp Ile Phe Glu Gln Trp Ala His Ser Glu Asp Leu Gln Ser Leu Leu
            740                 745                 750

Leu Arg Val Ala Asn Ala Val Ser Val Lys Gly Ile Tyr Lys Gln Met
            755                 760                 765

Pro Gly Cys Phe Asn Phe Leu Arg Lys Lys Leu Phe Phe Lys Thr Ser
            770                 775                 780

Met Gly Val Gln Val Glu Thr Ile Ser Pro Gly Asp Gly Arg Thr Phe
785                 790                 795                 800

Pro Lys Arg Gly Gln Thr Cys Val Val His Tyr Thr Gly Met Leu Glu
                805                 810                 815

Asp Gly Lys Lys Val Asp Ser Ser Arg Asp Arg Asn Lys Pro Phe Lys
            820                 825                 830

Phe Met Leu Gly Lys Gln Glu Val Ile Arg Gly Trp Glu Glu Gly Val
            835                 840                 845
```

```
Ala Gln Met Ser Val Gly Gln Arg Ala Lys Leu Thr Ile Ser Pro Asp
    850                 855                 860
Tyr Ala Tyr Gly Ala Thr Gly His Pro Gly Ile Ile Pro Pro His Ala
865                 870                 875                 880
Thr Leu Val Phe Asp Val Glu Leu Leu Lys Leu Glu
                885                 890
```

<210> SEQ ID NO 35
<211> LENGTH: 900
<212> TYPE: PRT
<213> ORGANISM: Artificial Sequence
<220> FEATURE:
<223> OTHER INFORMATION: Synthetic Polypeptide

<400> SEQUENCE: 35

```
Glu Val Lys Leu Val Glu Ser Gly Gly Gly Leu Val Leu Pro Gly Asp
1               5                   10                  15
Ser Leu Arg Leu Ser Cys Ala Thr Ser Glu Phe Thr Phe Thr Asp Tyr
            20                  25                  30
Tyr Met Thr Trp Val Arg Gln Pro Pro Arg Lys Ala Leu Glu Trp Leu
        35                  40                  45
Gly Phe Ile Arg Asn Arg Ala Asn Gly Tyr Thr Thr Glu Tyr Asn Pro
    50                  55                  60
Ser Val Lys Gly Arg Phe Thr Ile Ser Arg Asp Asn Ser Gln Ser Ile
65                  70                  75                  80
Leu Tyr Leu Gln Met Asn Thr Leu Arg Thr Glu Asp Ser Ala Thr Tyr
                85                  90                  95
Tyr Cys Ala Arg Val Ser Asn Trp Ala Phe Asp Tyr Trp Gly Gln Gly
            100                 105                 110
Thr Thr Leu Thr Val Ser Ser Gly Ser Thr Ser Gly Ser Gly Lys Pro
        115                 120                 125
Gly Ser Ser Glu Gly Ser Thr Lys Gly Asp Val Val Met Thr Gln Thr
    130                 135                 140
Pro Leu Ser Leu Pro Val Ser Leu Gly Asp Gln Ala Ser Ile Ser Cys
145                 150                 155                 160
Arg Ser Ser Gln Ser Leu Leu Lys Asn Asn Gly Asn Thr Phe Leu His
                165                 170                 175
Trp Tyr Leu Gln Lys Ser Gly Gln Ser Pro Lys Leu Leu Ile Tyr Lys
            180                 185                 190
Val Ser Asn Arg Leu Ser Gly Val Pro Asp Arg Phe Ser Gly Ser Gly
        195                 200                 205
Ser Gly Thr Tyr Phe Thr Leu Lys Ile Ser Arg Val Glu Ala Glu Asp
    210                 215                 220
Leu Gly Val Tyr Phe Cys Ser Gln Ser Thr His Ile Pro Tyr Thr Phe
225                 230                 235                 240
Gly Gly Gly Thr Lys Leu Glu Ile Lys Phe Trp Val Leu Val Val Val
                245                 250                 255
Gly Gly Val Leu Ala Cys Tyr Ser Leu Leu Val Thr Val Ala Phe Ile
            260                 265                 270
Ile Phe Trp Val Lys Arg Gly Arg Lys Lys Leu Leu Tyr Ile Phe Lys
        275                 280                 285
Gln Pro Phe Met Arg Pro Val Gln Thr Thr Gln Glu Glu Asp Gly Cys
    290                 295                 300
Ser Cys Arg Phe Pro Glu Glu Glu Glu Gly Gly Cys Glu Leu Gln Arg
305                 310                 315                 320
```

-continued

Arg Lys Tyr Arg Ser Asn Lys Gly Glu Ser Pro Val Glu Pro Ala Glu
                325                 330                 335

Pro Cys His Tyr Ser Cys Pro Arg Glu Glu Gly Ser Thr Ile Pro
        340                 345                 350

Ile Gln Glu Asp Tyr Arg Lys Pro Glu Pro Ala Cys Ser Pro Gly Ser
            355                 360                 365

Thr Ser Gly Ser Gly Lys Pro Gly Ser Ser Glu Gly Ser Thr Lys Gly
        370                 375                 380

Arg Val Lys Phe Ser Arg Ser Ala Asp Ala Pro Ala Tyr Lys Gln Gly
385                 390                 395                 400

Gln Asn Gln Leu Tyr Asn Glu Leu Asn Leu Gly Arg Arg Glu Glu Tyr
            405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
            435                 440                 445

Asp Lys Met Ala Glu Ala Tyr Ser Glu Ile Gly Met Lys Gly Glu Arg
450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
            485                 490                 495

Gly Ser Thr Ser Gly Ser Gly Lys Pro Gly Ser Ser Glu Gly Ser Thr
            500                 505                 510

Lys Gly Val Gly Ala Leu Glu Ser Leu Arg Gly Asn Ala Asp Leu Ala
            515                 520                 525

Tyr Ile Leu Ser Met Glu Pro Cys Gly His Cys Leu Ile Ile Asn Asn
            530                 535                 540

Val Asn Phe Cys Arg Glu Ser Gly Leu Arg Thr Arg Thr Gly Ser Asn
545                 550                 555                 560

Ile Asp Cys Glu Lys Leu Arg Arg Arg Phe Ser Ser Leu His Phe Met
                565                 570                 575

Val Glu Val Lys Gly Asp Leu Thr Ala Lys Lys Met Val Leu Ala Leu
            580                 585                 590

Leu Glu Leu Ala Gln Gln Asp His Gly Ala Leu Asp Cys Cys Val Val
            595                 600                 605

Val Ile Leu Ser His Gly Cys Gln Ala Ser His Leu Gln Phe Pro Gly
            610                 615                 620

Ala Val Tyr Gly Thr Asp Gly Cys Pro Val Ser Val Glu Lys Ile Val
625                 630                 635                 640

Asn Ile Phe Asn Gly Thr Ser Cys Pro Ser Leu Gly Gly Lys Pro Lys
                645                 650                 655

Leu Phe Phe Ile Gln Ala Cys Gly Gly Glu Gln Lys Asp His Gly Phe
            660                 665                 670

Glu Val Ala Ser Thr Ser Pro Glu Asp Glu Ser Pro Gly Ser Asn Pro
            675                 680                 685

Glu Pro Asp Ala Thr Pro Phe Gln Glu Gly Leu Arg Thr Phe Asp Gln
            690                 695                 700

Leu Asp Ala Ile Ser Ser Leu Pro Thr Pro Ser Asp Ile Phe Val Ser
705                 710                 715                 720

Tyr Ser Thr Phe Pro Gly Phe Val Ser Trp Arg Asp Pro Lys Ser Gly
                725                 730                 735

Ser Trp Tyr Val Glu Thr Leu Asp Asp Ile Phe Glu Gln Trp Ala His

```
            740                 745                 750
Ser Glu Asp Leu Gln Ser Leu Leu Leu Arg Val Ala Asn Ala Val Ser
            755                 760                 765

Val Lys Gly Ile Tyr Lys Gln Met Pro Gly Cys Phe Asn Phe Leu Arg
            770                 775                 780

Lys Lys Leu Phe Phe Lys Thr Ser Met Gly Val Gln Val Glu Thr Ile
785                 790                 795                 800

Ser Pro Gly Asp Gly Arg Thr Phe Pro Lys Arg Gly Gln Thr Cys Val
            805                 810                 815

Val His Tyr Thr Gly Met Leu Glu Asp Gly Lys Lys Val Asp Ser Ser
            820                 825                 830

Arg Asp Arg Asn Lys Pro Phe Lys Phe Met Leu Gly Lys Gln Glu Val
            835                 840                 845

Ile Arg Gly Trp Glu Glu Gly Val Ala Gln Met Ser Val Gly Gln Arg
            850                 855                 860

Ala Lys Leu Thr Ile Ser Pro Asp Tyr Ala Tyr Gly Ala Thr Gly His
865                 870                 875                 880

Pro Gly Ile Ile Pro Pro His Ala Thr Leu Val Phe Asp Val Glu Leu
            885                 890                 895

Leu Lys Leu Glu
            900

<210> SEQ ID NO 36
<211> LENGTH: 895
<212> TYPE: PRT
<213> ORGANISM: Artificial Sequence
<220> FEATURE:
<223> OTHER INFORMATION: Synthetic Polypeptide

<400> SEQUENCE: 36

Glu Val Gln Leu Val Gln Ser Gly Ala Glu Val Glu Lys Pro Gly Ala
1               5                   10                  15

Ser Val Lys Ile Ser Cys Lys Ala Ser Gly Ser Ser Phe Thr Gly Tyr
            20                  25                  30

Asn Met Asn Trp Val Arg Gln Asn Ile Gly Lys Ser Leu Glu Trp Ile
            35                  40                  45

Gly Ala Ile Asp Pro Tyr Tyr Gly Gly Thr Ser Tyr Asn Gln Lys Phe
        50                  55                  60

Lys Gly Arg Ala Thr Leu Thr Val Asp Lys Ser Thr Ser Thr Ala Tyr
65                  70                  75                  80

Met His Leu Lys Ser Leu Arg Ser Glu Asp Thr Ala Val Tyr Tyr Cys
            85                  90                  95

Val Ser Gly Met Glu Tyr Trp Gly Gln Gly Thr Ser Val Thr Val Ser
            100                 105                 110

Ser Gly Ser Thr Ser Gly Ser Gly Lys Pro Gly Ser Ser Glu Gly Ser
            115                 120                 125

Thr Lys Gly Asp Val Val Met Thr Gln Thr Pro Leu Ser Leu Pro Val
            130                 135                 140

Thr Pro Gly Glu Pro Ala Ser Ile Ser Cys Arg Ser Ser Gln Ser Leu
145                 150                 155                 160

Val His Arg Asn Gly Asn Thr Tyr Leu His Trp Tyr Leu Gln Lys Pro
            165                 170                 175

Gly Gln Ser Pro Lys Leu Leu Ile His Lys Val Ser Asn Arg Phe Ser
            180                 185                 190

Gly Val Pro Asp Arg Phe Ser Gly Ser Gly Ser Gly Thr Asp Phe Thr
```

-continued

```
            195                 200                 205
Leu Lys Ile Ser Arg Val Glu Ala Glu Asp Leu Gly Val Tyr Phe Cys
210                 215                 220

Ser Gln Ser Thr His Val Pro Pro Leu Thr Phe Gly Ala Gly Thr Lys
225                 230                 235                 240

Leu Glu Leu Lys Phe Trp Val Leu Val Val Val Gly Gly Val Leu Ala
                245                 250                 255

Cys Tyr Ser Leu Leu Val Thr Val Ala Phe Ile Ile Phe Trp Val Lys
                260                 265                 270

Arg Gly Arg Lys Lys Leu Leu Tyr Ile Phe Lys Gln Pro Phe Met Arg
            275                 280                 285

Pro Val Gln Thr Thr Gln Glu Glu Asp Gly Cys Ser Cys Arg Phe Pro
290                 295                 300

Glu Glu Glu Glu Gly Gly Cys Glu Leu Gln Arg Arg Lys Tyr Arg Ser
305                 310                 315                 320

Asn Lys Gly Glu Ser Pro Val Glu Pro Ala Glu Pro Cys His Tyr Ser
                325                 330                 335

Cys Pro Arg Glu Glu Glu Gly Ser Thr Ile Pro Ile Gln Glu Asp Tyr
            340                 345                 350

Arg Lys Pro Glu Pro Ala Cys Ser Pro Gly Ser Thr Ser Gly Ser Gly
            355                 360                 365

Lys Pro Gly Ser Ser Glu Gly Ser Thr Lys Gly Arg Val Lys Phe Ser
370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg Gly Ser Thr Ser Gly
                485                 490                 495

Ser Gly Lys Pro Gly Ser Ser Glu Gly Ser Thr Lys Gly Val Gly Ala
            500                 505                 510

Leu Glu Ser Leu Arg Gly Asn Ala Asp Leu Ala Tyr Ile Leu Ser Met
            515                 520                 525

Glu Pro Cys Gly His Cys Leu Ile Ile Asn Asn Val Asn Phe Cys Arg
530                 535                 540

Glu Ser Gly Leu Arg Thr Arg Thr Gly Ser Asn Ile Asp Cys Glu Lys
545                 550                 555                 560

Leu Arg Arg Arg Phe Ser Ser Leu His Phe Met Val Glu Val Lys Gly
                565                 570                 575

Asp Leu Thr Ala Lys Lys Met Val Leu Ala Leu Leu Glu Leu Ala Gln
            580                 585                 590

Gln Asp His Gly Ala Leu Asp Cys Cys Val Val Val Ile Leu Ser His
            595                 600                 605

Gly Cys Gln Ala Ser His Leu Gln Phe Pro Gly Ala Val Tyr Gly Thr
610                 615                 620
```

```
Asp Gly Cys Pro Val Ser Val Glu Lys Ile Val Asn Ile Phe Asn Gly
625                 630                 635                 640

Thr Ser Cys Pro Ser Leu Gly Gly Lys Pro Lys Leu Phe Phe Ile Gln
            645                 650                 655

Ala Cys Gly Gly Glu Gln Lys Asp His Gly Phe Glu Val Ala Ser Thr
        660                 665                 670

Ser Pro Glu Asp Glu Ser Pro Gly Ser Asn Pro Glu Pro Asp Ala Thr
    675                 680                 685

Pro Phe Gln Glu Gly Leu Arg Thr Phe Asp Gln Leu Asp Ala Ile Ser
690                 695                 700

Ser Leu Pro Thr Pro Ser Asp Ile Phe Val Ser Tyr Ser Thr Phe Pro
705                 710                 715                 720

Gly Phe Val Ser Trp Arg Asp Pro Lys Ser Gly Ser Trp Tyr Val Glu
                725                 730                 735

Thr Leu Asp Asp Ile Phe Glu Gln Trp Ala His Ser Glu Asp Leu Gln
            740                 745                 750

Ser Leu Leu Leu Arg Val Ala Asn Ala Val Ser Val Lys Gly Ile Tyr
        755                 760                 765

Lys Gln Met Pro Gly Cys Phe Asn Phe Leu Arg Lys Lys Leu Phe Phe
    770                 775                 780

Lys Thr Ser Met Gly Val Gln Val Glu Thr Ile Ser Pro Gly Asp Gly
785                 790                 795                 800

Arg Thr Phe Pro Lys Arg Gly Gln Thr Cys Val Val His Tyr Thr Gly
                805                 810                 815

Met Leu Glu Asp Gly Lys Lys Val Asp Ser Ser Arg Asp Arg Asn Lys
            820                 825                 830

Pro Phe Lys Phe Met Leu Gly Lys Gln Glu Val Ile Arg Gly Trp Glu
        835                 840                 845

Glu Gly Val Ala Gln Met Ser Val Gly Gln Arg Ala Lys Leu Thr Ile
850                 855                 860

Ser Pro Asp Tyr Ala Tyr Gly Ala Thr Gly His Pro Gly Ile Ile Pro
865                 870                 875                 880

Pro His Ala Thr Leu Val Phe Asp Val Glu Leu Leu Lys Leu Glu
                885                 890                 895

<210> SEQ ID NO 37
<211> LENGTH: 651
<212> TYPE: PRT
<213> ORGANISM: Artificial Sequence
<220> FEATURE:
<223> OTHER INFORMATION: Synthetic Polypeptide

<400> SEQUENCE: 37

Phe Trp Val Leu Val Val Gly Gly Val Leu Ala Cys Tyr Ser Leu
1               5                   10                  15

Leu Val Thr Val Ala Phe Ile Ile Phe Trp Val Lys Arg Gly Arg Lys
            20                  25                  30

Lys Leu Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu Gln Arg Arg Lys Tyr Arg Ser Asn Lys Gly Glu
65                  70                  75                  80

Ser Pro Val Glu Pro Ala Glu Pro Cys His Tyr Ser Cys Pro Arg Glu
                85                  90                  95
```

-continued

```
Glu Glu Gly Ser Thr Ile Pro Ile Gln Glu Asp Tyr Arg Lys Pro Glu
                100             105                 110
Pro Ala Cys Ser Pro Gly Ser Thr Ser Gly Ser Gly Lys Pro Gly Ser
            115                 120                 125
Ser Glu Gly Ser Thr Lys Gly Arg Val Lys Phe Ser Arg Ser Ala Asp
        130                 135                 140
Ala Pro Ala Tyr Lys Gln Gly Gln Asn Gln Leu Tyr Asn Glu Leu Asn
145                 150                 155                 160
Leu Gly Arg Arg Glu Glu Tyr Asp Val Leu Asp Lys Arg Arg Gly Arg
                165                 170                 175
Asp Pro Glu Met Gly Gly Lys Pro Arg Arg Lys Asn Pro Gln Glu Gly
            180                 185                 190
Leu Tyr Asn Glu Leu Gln Lys Asp Lys Met Ala Glu Ala Tyr Ser Glu
        195                 200                 205
Ile Gly Met Lys Gly Glu Arg Arg Arg Gly Lys Gly His Asp Gly Leu
    210                 215                 220
Tyr Gln Gly Leu Ser Thr Ala Thr Lys Asp Thr Tyr Asp Ala Leu His
225                 230                 235                 240
Met Gln Ala Leu Pro Pro Arg Gly Ser Thr Ser Gly Ser Gly Lys Pro
                245                 250                 255
Gly Ser Ser Glu Gly Ser Thr Lys Gly Val Gly Ala Leu Glu Ser Leu
            260                 265                 270
Arg Gly Asn Ala Asp Leu Ala Tyr Ile Leu Ser Met Glu Pro Cys Gly
        275                 280                 285
His Cys Leu Ile Ile Asn Asn Val Asn Phe Cys Arg Glu Ser Gly Leu
    290                 295                 300
Arg Thr Arg Thr Gly Ser Asn Ile Asp Cys Glu Lys Leu Arg Arg Arg
305                 310                 315                 320
Phe Ser Ser Leu His Phe Met Val Glu Val Lys Gly Asp Leu Thr Ala
                325                 330                 335
Lys Lys Met Val Leu Ala Leu Leu Glu Leu Ala Gln Gln Asp His Gly
            340                 345                 350
Ala Leu Asp Cys Cys Val Val Val Ile Leu Ser His Gly Cys Gln Ala
        355                 360                 365
Ser His Leu Gln Phe Pro Gly Ala Val Tyr Gly Thr Asp Gly Cys Pro
    370                 375                 380
Val Ser Val Glu Lys Ile Val Asn Ile Phe Asn Gly Thr Ser Cys Pro
385                 390                 395                 400
Ser Leu Gly Gly Lys Pro Lys Leu Phe Phe Ile Gln Ala Cys Gly Gly
                405                 410                 415
Glu Gln Lys Asp His Gly Phe Glu Val Ala Ser Thr Ser Pro Glu Asp
            420                 425                 430
Glu Ser Pro Gly Ser Asn Pro Glu Pro Asp Ala Thr Pro Phe Gln Glu
        435                 440                 445
Gly Leu Arg Thr Phe Asp Gln Leu Asp Ala Ile Ser Ser Leu Pro Thr
    450                 455                 460
Pro Ser Asp Ile Phe Val Ser Tyr Ser Thr Phe Pro Gly Phe Val Ser
465                 470                 475                 480
Trp Arg Asp Pro Lys Ser Gly Ser Trp Tyr Val Glu Thr Leu Asp Asp
                485                 490                 495
Ile Phe Glu Gln Trp Ala His Ser Glu Asp Leu Gln Ser Leu Leu Leu
            500                 505                 510
```

Arg Val Ala Asn Ala Val Ser Val Lys Gly Ile Tyr Lys Gln Met Pro
            515                 520                 525

Gly Cys Phe Asn Phe Leu Arg Lys Lys Leu Phe Phe Lys Thr Ser Met
530                 535                 540

Gly Val Gln Val Glu Thr Ile Ser Pro Gly Asp Gly Arg Thr Phe Pro
545                 550                 555                 560

Lys Arg Gly Gln Thr Cys Val Val His Tyr Thr Gly Met Leu Glu Asp
                565                 570                 575

Gly Lys Lys Val Asp Ser Ser Arg Asp Arg Asn Lys Pro Phe Lys Phe
            580                 585                 590

Met Leu Gly Lys Gln Glu Val Ile Arg Gly Trp Glu Glu Gly Val Ala
            595                 600                 605

Gln Met Ser Val Gly Gln Arg Ala Lys Leu Thr Ile Ser Pro Asp Tyr
        610                 615                 620

Ala Tyr Gly Ala Thr Gly His Pro Gly Ile Ile Pro Pro His Ala Thr
625                 630                 635                 640

Leu Val Phe Asp Val Glu Leu Leu Lys Leu Glu
                645                 650

<210> SEQ ID NO 38
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 38

Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 39
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 39

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 40

<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 40

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 41
<211> LENGTH: 41
<212> TYPE: PRT
<213> ORGANISM: Artificial Sequence
<220> FEATURE:
<223> OTHER INFORMATION: Synthetic Polypeptide

<400> SEQUENCE: 41

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 42
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 42

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 43
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 43

Cys Trp Leu Thr Lys Lys Lys Tyr Ser Ser Ser Val His Asp Pro Asn
1               5                   10                  15

```
Gly Glu Tyr Met Phe Met Arg Ala Val Asn Thr Ala Lys Lys Ser Arg
            20                  25                  30

Leu Thr Asp Val Thr Leu
        35
```

<210> SEQ ID NO 44
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 44

```
Ala Leu Tyr Leu Leu Arg Arg Asp Gln Arg Leu Pro Pro Asp Ala His
1               5                   10                  15

Lys Pro Pro Gly Gly Ser Phe Arg Thr Pro Ile Gln Glu Glu Gln
            20                  25                  30

Ala Asp Ala His Ser Thr Leu Ala Lys Ile
        35                  40
```

<210> SEQ ID NO 45
<211> LENGTH: 194
<212> TYPE: PRT
<213> ORGANISM: Artificial Sequence
<220> FEATURE:
<223> OTHER INFORMATION: Synthetic Polypeptide

<400> SEQUENCE: 45

```
Lys Arg Ile Lys Pro Ile Val Trp Pro Ser Leu Pro Asp His Lys Lys
1               5                   10                  15

Thr Leu Glu His Leu Cys Lys Lys Pro Arg Lys Asn Leu Asn Val Ser
            20                  25                  30

Phe Asn Pro Glu Ser Phe Leu Asp Cys Gln Ile His Arg Val Asp Asp
        35                  40                  45

Ile Gln Ala Arg Asp Glu Val Glu Gly Phe Leu Gln Asp Thr Phe Pro
    50                  55                  60

Gln Gln Leu Glu Glu Ser Glu Lys Gln Arg Leu Gly Gly Asp Val Gln
65                  70                  75                  80

Ser Pro Asn Cys Pro Ser Glu Asp Val Val Ile Thr Pro Glu Ser Phe
                85                  90                  95

Gly Arg Asp Ser Ser Leu Thr Cys Leu Ala Gly Asn Val Ser Ala Cys
            100                 105                 110

Asp Ala Pro Ile Leu Ser Ser Arg Ser Leu Asp Cys Arg Glu Ser
        115                 120                 125

Gly Lys Asn Gly Pro His Val Tyr Gln Asp Leu Leu Leu Ser Leu Gly
    130                 135                 140

Thr Thr Asn Ser Thr Leu Pro Pro Pro Phe Ser Leu Gln Ser Gly Ile
145                 150                 155                 160

Leu Thr Leu Asn Pro Val Ala Gln Gly Gln Pro Ile Leu Thr Ser Leu
                165                 170                 175

Gly Ser Asn Gln Glu Glu Ala Tyr Val Thr Met Ser Ser Phe Tyr Gln
            180                 185                 190

Asn Gln
```

CHIMERIC ANTIGEN RECEPTORS AND USES THEREOF

RELATED APPLICATIONS

This application is a National Stage Application of PCT/US16/18716, filed Feb. 19, 2016, entitled "CHIMERIC ANTIGEN RECEPTORS AND USES THEREOF", which claims the benefit under 35 U.S.C. § 119(e) of U.S. Provisional Application Ser. No. 62/118,080, filed on Feb. 19, 2015, entitled "CHIMERIC ANTIGEN RECEPTOR COMPRISING INTERLEUKIN-15 RECEPTOR INTRACELLULAR DOMAIN AND USES THEREOF", 62/134,444, filed on Mar. 17, 2015, entitled "CHIMERIC ANTIGEN RECEPTORS THAT TARGET GD2", 62/152,792, filed on Apr. 24, 2015, entitled "CHIMERIC ANTIGEN RECEPTORS THAT TARGET CD30 AND USES THEREOF", and 62/165,836, filed on May 22, 2015, entitled "CHIMERIC ANTIGEN RECEPTORS THAT TARGET GD2", the entire contents of each application which are incorporated herein by reference.

BACKGROUND

Chimeric Antigen Receptors (CARs) are engineered T cell receptors displaying specificity against target antigens based on a single chain FV (scFv) antibody moiety. Although CARs show promise as therapeutic agents, several challenges (e.g., the induction of antigen-specific toxicities targeting normal tissues expressing the target-antigen, and the extreme potency of CAR-T cell treatments resulting in life-threatening cytokine-release syndromes) limit their use in a clinical context. Therefore, there is a need to develop safer and more clinically effective CARs.

SUMMARY

In some aspects, the disclosure relates to chimeric antigen receptors (CARs) comprising an antigen binding domain (e.g., anti-CD19, anti-CD30, anti-GD2), and/or a cytoplasmic domain of a interleukin (IL)-15-receptor α, and/or a chimeric cytoplasmic domain including a CD27 cytoplasmic domain fused to a 4-1BB cytoplasmic domain. Use of the CARs in T cells, compositions, kits and methods is also contemplated by the disclosure.

Aspects of the disclosure relate to CARs comprising a cytoplasmic domain of a interleukin(IL)-15-receptor α, and uses of such CARs to produce CAR T-cells (CARTs) and/or CAR-modified immune cells such as NK (natural killer) cells, which can be used in various methods, such as treatment methods, or compositions.

As described herein, it was found that including the cytoplasmic domain of IL-15-receptor α (IL-15Rα) in a CAR construct resulted in CARTs with greater expansion potential upon antigen stimulation and higher killing efficacy. Further, the CARTs maintained killing efficacy even on repetitive addition of an excess of target cells. The CARTs also produced increased amounts of effector cytokines, as determined by intracellular staining and flow cytometry based bead assays.

Accordingly, aspects of the disclosure relate to a chimeric antigen receptor (CAR) comprising an antigen binding domain; a transmembrane domain; and a cytoplasmic domain containing an interleukin 15-receptor α (IL-15Rα) cytoplasmic domain. In some embodiments, the transmembrane domain is a CD28 or CD8 transmembrane domain. In some embodiments, the cytoplasmic domain further comprises a CD3zeta signal transduction domain. In some embodiments, the cytoplasmic domain further comprises a CD27 signaling domain. In some embodiments, the antigen binding domain is a single-chain variable fragment (scFv). In some embodiments, the antigen binding domain is specific for CD19.

Aspects of the disclosure relate to CARs comprising a chimeric cytoplasmic domain including a CD27 cytoplasmic domain fused to a 4-1BB cytoplasmic domain, and uses of such CARs to produce CARTs and/or CAR-modified immune cells such as NK (natural killer) cells, which can be used in various methods, such as treatment methods, or compositions.

In some aspects, the disclosure relates to a chimeric antigen receptor (CAR) comprising: an antigen binding domain; a transmembrane domain; and a cytoplasmic domain containing a CD27 intracellular domain.

In some embodiments, the transmembrane domain is a CD28 or CD8 transmembrane domain. In some embodiments, the cytoplasmic domain further comprises a 4-1BB intracellular domain. In some embodiments, the cytoplasmic domain further comprises a CD3zeta signal transduction domain. In some embodiments, the cytoplasmic domain further comprises an iCasp9 domain and/or a FKBP domain. In some embodiments, the antigen binding domain is a single-chain variable fragment (scFv).

In some embodiments, a CAR comprises a CD28 transmembrane domain, cytoplasmic domain comprising a CD27 intracellular domain and a 4-1BB intracellular domain, and a CD3zeta signal transduction domain. In some embodiments, a CAR further comprises an iCasp9 domain and/or a FKBP domain.

In some embodiments, a CAR further comprises a first spacer between the CD28 transmembrane domain and the cytoplasmic domain comprising a CD27 intracellular domain and a 4-1BB intracellular domain, and a second spacer between the cytoplasmic domain comprising a CD27 intracellular domain and a 4-1BB intracellular domain and the CD3zeta signal transduction domain. In some embodiments, the CAR further comprises a third spacer between the CD3zeta signal transduction domain and the iCasp9 domain and/or a FKBP domain. In some embodiments, the antigen binding domain of a CAR is specific for CD30.

Aspects of the disclosure relate to CARs comprising an antigen-binding domain specific for Disialoganglioside 2 (GD2), and uses of such CARs to produce CAR-modified immune cells such as T cells (also referred to herein as CARTs) or NK (natural killer) cells, which can be used in various methods, such as treatment methods, or compositions. In some aspects of the disclosure, such CARs are used to treat retinoblastoma or osteosarcoma, such as a juvenile subject having retinoblastoma or osteosarcoma.

As described herein, it was found that GD2-specific CAR-expressing T cells could kill both osteosarcoma and retinoblastoma cells, both of which express GD2. As a result, it is expected that GD2-specific CARs will be useful for treatment of both osteosarcoma and retinoblastoma.

Aspects of the disclosure relate to a chimeric antigen receptor (CAR) comprising an antigen binding domain specific for GD2; a transmembrane domain; and a cytoplasmic domain containing one or more (e.g., one, two, or three) of a CD27 signaling domain, a 4-1BB intracellular domain, and a CD3zeta signal transduction domain. In some embodiments, the transmembrane domain is a CD28 or CD8 transmembrane domain. In some embodiments, the antigen binding domain is a single-chain variable fragment (scFv).

Other aspects of the disclosure relate to a nucleic acid comprising a sequence that encodes the CAR of any one of the above embodiments or as otherwise described herein.

Yet other aspects relate to an immune cell comprising a CAR of any one of the above embodiments or as otherwise described herein and/or a nucleic acid of any one of the above embodiments or as otherwise described herein. In some embodiments, the immune cell is a T cell or NK cell. In some embodiments, the immune cell is a T cell.

Other aspects of the disclosure relate to a composition comprising a plurality of the immune cell of any one of the above embodiments or as otherwise described herein. In some embodiments, the composition comprises a pharmaceutically acceptable carrier.

Another aspect of the disclosure relates to a method of generating a plurality of CAR-modified immune cells, the method comprising introducing a lentiviral vector comprising a nucleic acid of any one of the above embodiments or as otherwise described herein into a plurality of immune cells. In some embodiments, the immune cells are T cells.

Other aspects of the disclosure relate to a method of treating a subject having a disease, the method comprising administering an immune cell of any one of the above embodiments or as otherwise described herein, the composition of any one of the above embodiments or as otherwise described herein, or the plurality of immune cells produced by a method of any one of the above embodiments or as otherwise described herein into a subject having a disease or at risk of having a disease.

In some embodiments, the disease is cancer, an autoimmune disease or an infection. In some embodiments, the disease is cancer. In some embodiments, the disease is a CD30+ cancer. In some embodiments, the cancer is osteosarcoma or retinoblastoma.

In some embodiments, the method further comprises administering a PD-L1 or PD1 inhibitor to the subject.

Other aspects of the disclosure relate to a method of treating a subject having cancer, the method comprising administering (a) an immune cell expressing a CAR that targets GD2 and (b) a PD-L1 or PD1 inhibitor to a subject having cancer. In some embodiments, the cancer is osteosarcoma or retinoblastoma. In some embodiments, the immune cell is a T cell. In some embodiments, the immune cell is a plurality of immune cells in a composition.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It should be appreciated that in greyscale versions of the drawings, GFP fluorescence appears as areas of lighter shading (e.g., white shading)

FIG. 23A) Representative dot plots from short term killing of U2OS cells by GD2 CAR-JK cells (E:T ratio=2:1). Effecter and target cells are separated by FITC signal, FITC positive target cells (upper panels) were gated and determined percentage of death cell by Annexin V versus PI plots (lower panels). FIG. 23B) Percent specific lysis of U2OS by GD2 CAR-JK cell was presented in comparison with control CAR-JK cell, * indicates a significant difference (p=0.0049). FIG. 23C) Representative dot plots from short term killing of HOS cells by GD2 CAR-JK cells (E:T ratio=2:1) showing percentage of FITC positive target cells (upper panels) and Annexin V and/or PI positive target cells (lower panels). FIG. 23D) Percent specific lysis of HOS by GD2 CAR-JK cell shows higher but not significant different compare to control CAR-JK cells (p=0.078; NS=not significant different).

FIGS. 24A-24G show exemplary CAR-Primary T cell killing of OS target. The killing ability of GD2 CAR in primary T cells were determined. FIG. 24A) Flow cytometry analysis of U2OSw cells by GD2 CAR-T cells after co-culture at E:T ratio of 4:1, 2:1, 1:1, 1:2, * indicates significant different from controls (p<0.05). FIG. 24B) Percent specific lyses of U2OSw cells after 3 day co-culture, * indicates significant different from control T cells (p<0.05). FIG. 24C) Flow cytometry analysis of HOSw cells by GD2 CAR-T cells after co-culture at E:T ratio of 4:1, 2:1, 1:1, 1:2, * indicates significant different from controls (p<0.05). FIG. 24D) Percent specific lyses of HOSw cells after 3 day co-culture, * indicates significant different from control T cells (p<0.05). FIG. 24E) Percent specific lyses of OS156 cells after 3 day co-culture, * indicates significant different from control T cells (p<0.05). FIG. 24F) Target cells (green, fluorescent) and effecter cells (no color) under fluorescence microscope after 4 days co-culture. FIG. 24G) Target cells (green, fluorescent) and effecter cells (no color) under fluorescence microscope after 3, 7 or 12 days co-culture.

FIG. 25A) and FIG. 25B) Flow cytometry histogram overlays show surface expression of PD-L1 in U2OS and HOS cell. The shadowed area represents isotype control. Inner number indicates percent positive population and MFI of the positive population. FIG. 25C) and FIG. 25D) MFI analysis of PD-L1 expression in OS cells after CAR T co-culture.

FIG. 26C) and FIG. 26F) Increased CAR T cell death after PD-1 up-regulation. Percent CAR T cell death after 1 day co-culture with U2OSw (C) and HOSw (D) cells, # indicates significant different at p<0.05.

FIG. 29A shows analysis of cell death by using AnnexinV/PI staining. After 24 hr of co-culture experiment, the suspension cells were harvested and stained with AnnexinV-PE/PI dye followed by flow cytometric analysis. FIG. 29B shows the percent cell death at 1 day after co-culture. FIG. 29C shows the % of specific lysis. FIG. 29D is a series of photographs showing fluorescence microscopic monitoring of tumor cell lysis. Y79 RB wasort cells (1×105) were cultured with control T cells or CD19 CAR T cells, or GD2 CAR T cells at the effector/target ratio (1:1) for 24 h, and the lysis of tumor cells were monitored under fluorescence microscope.

DETAILED DESCRIPTION

Figure 1:
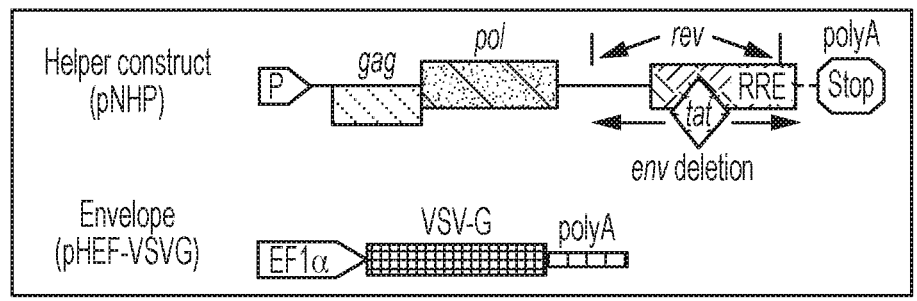
FIG. 1 is a diagram showing an exemplary Chimeric Antigen Receptor (CAR) basic structure including the antigen binding scFv domain and the various co-stimulatory domains.
Figure 1:
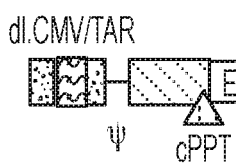
Figure 1:
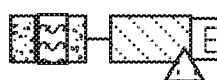
Figure 1:
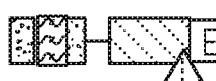
Figure 1:
Figure 1:

In some aspects, the disclosure relates to chimeric antigen receptors (CARs) comprising an antigen binding domain (e.g., anti-CD19, anti-CD30, anti-GD2), and/or a cytoplasmic domain of a interleukin(IL)-15-receptor α, and/or a chimeric cytoplasmic domain including a CD27 cytoplasmic domain fused to a 4-1BB cytoplasmic domain. Use of the CARs in T cells, compositions, kits and methods is also contemplated by the disclosure.

The invention relates, in some embodiments, to chimeric antigen receptors (CARs) and uses thereof in T cells (e.g., to make CAR T cells), methods, nucleic acids, compositions, kits and the like. CARs are molecules that combine antibody-based specificity for a desired antigen (e.g., tumor antigen) with a T cell receptor-activating intracellular domain to generate a chimeric protein that exhibits a specific anti-tumor cellular immune activity. It should be appreciated that, in some embodiments, exemplary, non-limiting arrangements of CARs are described from left to right, N-terminus to C-terminus of the CAR.

In some aspects, the disclosure relates to CARs having an interleukin 15-receptor α (IL-15Rα) cytoplasmic domain. CARs containing this domain had several advantageous and surprising features including greater expansion potential upon antigen stimulation, higher killing efficacy, maintained killing efficacy upon repetitive addition of excess target cells, and an increased amount of effector cytokines compared to CARs not containing this domain.

In some embodiments, the present invention relates, in part, to the use of T cells genetically modified to stably express a desired CAR, e.g., containing a IL-15Rα cytoplasmic domain, containing a CD30 antigen binding domain, containing a GD2 antigen binding domain, etc. T cells expressing a CAR are referred to herein as CAR T cells, CARTs, or CAR modified T cells. Preferably, the cell can be genetically modified to stably express an antibody binding domain on its surface, conferring novel antigen specificity that is MHC independent. In some instances, the T cell is genetically modified to stably express a CAR that combines an antigen recognition domain of a specific antibody with an transmembrane domain and a cytoplasmic domain into a single chimeric protein. In some embodiments, two CAR proteins dimerize (e.g., form homo- or heterodimers) in vivo.

In some embodiments, a CAR comprises an antigen binding domain, a transmembrane domain, a cytoplasmic domain comprising an IL-15Rα cytoplasmic domain, optionally further comprising a CD3 zeta (CD3z) signaling domain and/or a CD27 signaling domain. In some embodiments, the arrangement of the elements of the CAR is selected from one of the following exemplary, non-limiting arrangements (from N-terminus to C-terminus):
scFv-CD28-IL-15Rα-CD3z
scFv-CD28-CD27-IL-15Rα-CD3z
scFv-CD28-(4-1BB)-CD27-IL-15Rα-CD3z
scFv-CD8-CD27-IL-15Rα-CD3z
scFv-CD8-(4-1BB)-CD27-IL-15Rα-CD3z In some aspects, the disclosure relates to CARs having a CD30 antigen binding domain and an intracellular domain comprising a 4-1BB intracellular domain and a CD27 intracellular domain. In some embodiments, the CARs further comprise a self-destructive domain (e.g., an iCasp9-FKBP domain) that further improves safety. CARs containing these domains had several surprising features including an acceptable safety profile, and mediate effective killing of CD30+ cancer cells both in vitro and in vivo.

In some embodiments, a CAR (e.g., CAR having a CD30 antigen binding domain) comprises an antigen binding domain, a transmembrane domain, a cytoplasmic domain comprising a 4-1BB intracellular domain and a CD27 intracellular domain, optionally further comprising a CD3 zeta (CD3z) signaling domain, and/or an apoptosis-inducing iCasp9-FKBP domain. In some embodiments, the arrangement of the elements of the CAR is selected from one of the following exemplary, non-limiting arrangements (from N-terminus to C-terminus):
scFv-CD28-(4-1BB)-CD27-CD3z-iCasp9-FKBP
scFv-CD28-CD27-(4-1BB)-CD3z-iCasp9-FKBP
scFv-CD8-(4-1BB)-CD27-CD3z-iCasp9-FKBP
scFv-CD8-CD27-(4-1BB)-CD3z-iCasp9-FKBP In some aspects, the disclosure relates to the discovery that GD2 was expressed on both osteosarcoma and retinoblastoma cells and that GD2-specific CAR-expressing T cells could kill both osteosarcoma and retinoblastoma cells. As a result, it is expected that such CARs (e.g., GD2-specific CARs) will be useful for treatment of both osteosarcoma and retinoblastoma. In some embodiments, GD2-specific CARs contain an antigen binding domain (such as an scFV) specific for GD2. In some embodiments, the arrangement of the elements of the CAR (e.g., GD2-specific CAR) is selected from one of the following exemplary, non-limiting arrangements (from N-terminus to C-terminus):
GD2scFv-CD28-(4-1BB)-CD27-CD3z
GD2scFv-CD8-CD28-CD3z
GD2scFv-CD28-(4-1BB)-CD27-CD3z-Casp9-FKBP
GD2scFv-CD8-CD28-CD3z-Casp9-FKBP A CAR molecule may also include several hinge elements and/or spacer sequences (such as between individual domain elements). In some embodiments, the spacer and/or hinge sequences of the CAR are selected from one or more of the following exemplary sequences:

GGGGS, (SEQ ID NO: 1)

GGGGSGGGGS, (SEQ ID NO: 2)

(GGGGS)x3, (SEQ ID NO: 3)

GSTSGGGSGGGSGGGSS, (SEQ ID NO: 4)

GSTSGSGKPGSSEGSTKG, (SEQ ID NO: 5)

GGGGSGGG, (SEQ ID NO: 6)

VEPKSCDKTHTCPPCP, (SEQ ID NO: 7)

LDPKSSDKTHTCPPCP, (SEQ ID NO: 8)

VEPKSPDKTHTCPPCP, (SEQ ID NO: 9)
or

LDKTHTCPPCP. (SEQ ID NO: 10)

In some embodiments, the present invention relates, in part, to a CAR that incorporates a series of domains that provide different functional aspects that may synergistically work together to improve efficacy. For example, the CAR may include one or more of: an antigen binding domain, a hinge domain, an antigen co-signaling domain that stimulates activity (e.g., an IL-15Rα cytoplasmic domain, a 4-1BB cytoplasmic domain, or another cytoplasmic domain), a survival domain that increases T-cell or immune effector cell survival, a T-cell or immune effector cell memory domain, and an effector activating domain. Alternatively, the CAR may further include a domain that induces safety (e.g., an apoptosis-inducing iCasp9-FKBP domain).

In some embodiments, a CAR of the invention comprises an extracellular domain having an antigen binding domain, a transmembrane domain, and a multi-functional cytoplasmic domain. In some embodiments, the CAR comprises a fully human antibody or antibody fragment. In some embodiments, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex.

In some embodiments, the CAR T cells or other CAR-modified immune cells (e.g., CAR-modified NK cells) of the invention are generated by introducing a lentiviral vector comprising a nucleic acid that encodes a desired CAR into T cells or other immune cells (e.g., into NK cells). In some embodiments, the lentiviral vector comprises a nucleic acid that encodes a CAR comprising an antigen binding domain (e.g., that targets CD19), a transmembrane domain, and a cytoplasmic domain. In some embodiments, the CAR T cells or other CAR-modified immune cells (e.g., NK cells) of the invention are able to replicate in vivo resulting in long-term persistence that can lead to sustained tumor control. In some embodiments, the CAR T cell or other CAR-modified immune cells of the invention can be generated by transfecting a transposon or RNA encoding the desired CAR, into the T cells or other immune cells. In some embodiments, the CAR is transiently expressed in the genetically modified CAR T cell or other CAR-modified immune cells.

In some embodiments, the invention relates to administering a genetically modified immune cell (e.g., a genetically modified T cell or NK cell) expressing a CAR for the treatment of a patient having cancer or at risk of having cancer, or having an autoimmune disease or at risk of having an autoimmune disease, e.g., using lymphocyte infusion. In some embodiments, autologous lymphocyte infusion is used in the treatment. In some embodiments, autologous PBMCs are collected from a patient in need of treatment and immune cells (e.g., T cells or NK cells) are activated and expanded using the methods described herein and known in the art and then infused back into the patient.

In some embodiments, the cancer is a CD30+ cancer (e.g., a cancer expressing CD30). Examples of cancers expressing CD30 include Hodgkin's lymphoma (HL), anaplastic large cell lymphoma (ALCL), diffuse large B cell lymphoma, primary effusion lymphoma, adult T-cell leukemia/lymphoma, mycosis fungoides, extranodal natural killer/T-cell lymphoma and peripheral T/NK cell lymphoma. In some embodiments the cancer is a GD2-expressing cancer, such as retinoblastoma or osteosarcoma.

Exemplary Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies, human antibodies, and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')$_2$, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations, ϰ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "tumor antigen" as used herein refers to an antigen associated with a cancer cell. In some embodiments the tumor antigen is CD19, which is associated with B cell malignancies. In some embodiments, the tumor antigen is CD30, which is typically associated with lymphomas (e.g., HL, ALCL, diffuse large cell B-lymphoma, etc. Examples of other tumor antigens include, but are not limited to, CD2, CD5, CD10, CD20, CD22, CD30, CD33, CD38, CD52, CD56, CD74, CD138, CD317, Her2, VEGFR2, EGFRviii, CXCR4, BCMA, GD2, GD3, and any other antigens over-expressed in tumor cells.

In some embodiments the tumor antigen is GD2. GD2 is a disialoganglioside that is expressed on cancer cells, such as retinoblastoma or osteosarcoma. An exemplary structure of GD2 is as follows:

tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, the term "autologous" is meant to refer to any material derived from the same individual to which it is later to be re-introduced into the individual.

"Allogeneic" refers to a graft derived from a different animal of the same species. "Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include, but are not limited to, breast cancer, prostate cancer, ovarian cancer, cervical cancer, skin cancer, pancreatic cancer, colorectal cancer, renal cancer, liver cancer, brain cancer, lymphoma, leukemia (e.g., chronic lymphocytic leukemia, acute lymphoblastic leukemia, pediatric acute B cell leukemia, or post hematopoietic stem cell transplant relapsed leukemia), lung cancer and the like. In some embodiments, cancer refers to B-cell related malignancies (e.g., B-cell chronic lymphocytic leukemia,

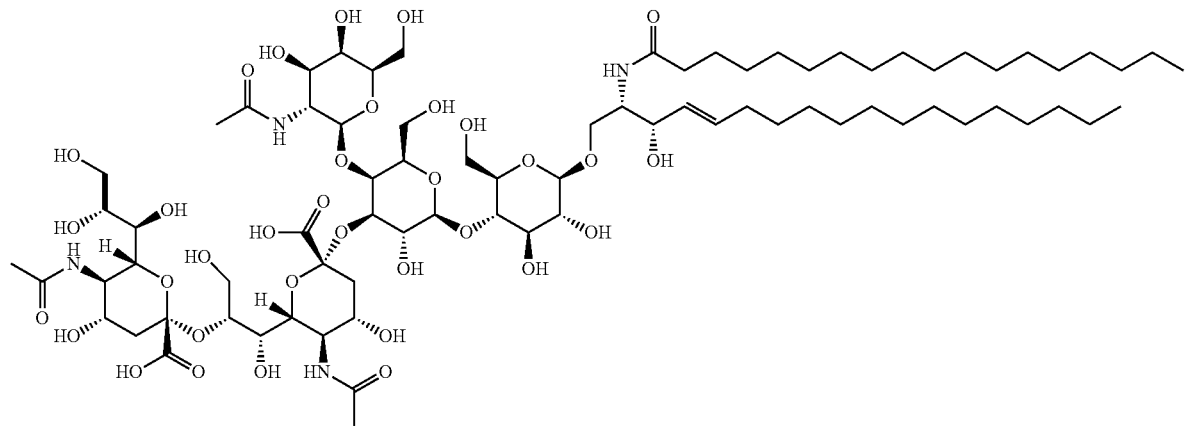

The IUPAC name for GD2 is (2R,4R,5S,6S)-2-[3-[(2S, 3S,4R,6S)-6-[(2S,3R,4R,5S,6R)-5-[(2S,3R,4R,5R,6R)-3-acetamido-4,5-dihydroxy-6-(hydroxymethyl)oxan-2-yl] oxy-2-[(2R,3S,4R,5R,6R)-4,5-dihydroxy-2-(hydroxymethyl)-6-RE)-3-hydroxy-2-(octadecanoylamino) octadec-4-enoxy]oxan-3-yl]oxy-3-hydroxy-6-(hydroxymethyl)oxan-4-yl]oxy-3-amino-6-carboxy-4-hydroxyoxan-2-yl]-2,3-dihydroxypropoxyl-5-amino-4-hydroxy-6-(1,2,3-trihydroxypropyl)oxane-2-carboxylic acid (see, e.g., PubChem ID 6450346).

The term "target antigen" as used herein refers to an antigen associated with a disease-associated target cell. Examples of target antigens include but are not limited to CD2, CD5, CD7, CD10, CD19, CD20, CD22, CD30, CD33, CD38, CD52, CD56, CD74, CD138, CD317, Her2, VEGFR2, EGFRviii, CXCR4, BCMA, GD2, GD3, and any other antigens over-expressed in target cells or diseased cells. In some embodiments, the diseased cell is a B cell that produces auto-antibodies.

The term "anti-tumor effect" as used herein, refers to a biological effect which can be manifested by a decrease in acute lymphoblastic leukemia, B-cell prolymphocytic leukemia, precursor B lymphoblastic leukemia, Hairy cell leukemia, diffuse large B cell lymphoma, follicular lymphoma, marginal zone lymphoma, small cell lymphocytic lymphoma, mantle cell lymphoma, Burkitt lymphoma, primary mediastinal (thymic) large B-cell lymphoma, lymphoplasmacytic lymphoma, nodal marginal zone B cell lymphoma, intravascular large B-cell lymphoma, primary effusion lymphoma, lymphomatoid granulomatosis, or plasmablastic lymphoma).

In some embodiments, cancer refers to CD30+ cancers (e.g., Hodgkin's lymphoma (HL), anaplastic large cell lymphoma (ALCL), diffuse large B cell lymphoma, and peripheral T/NK cell lymphoma, primary effusion lymphoma, adult T-cell leukemia/lymphoma, mycosis fungoides, and extranodal natural killer/T-cell lymphoma).

In some embodiments, the cancer is a GD2-expressing cancer. In some embodiments, the cancer is retinoblastoma or osteosarcoma. Retinoblastoma is a cancer that develops from cells of the retina and is the most common malignant tumor in children. Retinoblastoma can be identified by the skilled practitioner, e.g., using techniques known in the art including red reflex, Hirschberg test, an eye examination, computerized tomography (CT), magnetic resonance imaging (MRI), or ultrasound. Genetic testing, e.g., mutations in the RB1 gene may also be used to identify subjects. Osteosarcoma is a tumor that occurs in the bone which is of mesenchymal origin. Osteosarcoma occurs most often in children and young adults. Osteosarcoma can be identified by the skilled practitioner, e.g., using techniques known in the art including X-ray, CT scan, PET scan, bone scan, MRI, or biopsy.

The term "autoimmune disease" as used herein refers to a disease characterized by an abnormal immune response of the body against the body's own cells and tissues. The immune response may be systemic or may be restricted to certain tissue types or organs. Examples of various autoimmune diseases include, but are not limited to, acute disseminated encephalomyelitis, Addison's disease, alopecia areata, autoimmune cardiomyopathy, autoimmune hemolytic anemia, autoimmune hepatitis, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticarial, autoimmune uveitis, Behçet's disease, Celiac disease, Churg-Strauss syndrome, cold agglutinin disease, Crohn's disease, dermatomyositis, diabetes mellitus type 1, eosinophilic fasciitis, gastrointestinal pemphigoid, Goodpasture's syndrome, Graves' disease, Guillain-Barré syndrome, Hashimoto's encephalopathy, Hashimoto's thyroiditis, idiopathic thrombocytopenic purpura, lupus erythematosus, Miller-Fisher syndrome, mixed connective tissue disease, multiple sclerosis, myasthenia gravis, pemphigus vulgaris, pernicious anaemia, polymyositis, primary biliary cirrhosis, psoriasis, psoriatic arthritis, relapsing polychondritis, rheumatoid arthritis, rheumatic fever, Sjögren's syndrome, temporal arteritis, transverse myelitis, ulcerative colitis, undifferentiated connective tissue disease, vasculitis, and Wegener's granulomatosis.

The term "infection" as used herein refers to an invasion of a host's cells or tissues with an infectious organism, such as a bacteria, virus, or fungus.

An "effective amount" as used herein, means an amount which provides a therapeutic or prophylactic benefit.

As used herein, the term "exogenous" refers to any material introduced from or produced outside an organism, cell, tissue or system.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

Unless otherwise specified, a "nucleotide sequence or nucleic acid encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lenti viruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lenti viruses. Vectors derived from lenti viruses offer the means to achieve significant levels of gene transfer in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Codon-optimized" means that codons relating to a specific amino acid are optimized for translational efficiency of a gene of interest. Codon optimization typically involves evaluating the gene or sequence of interest and substituting the codon with a more prevalent or common codon used for the same amino acid in a specific cell or species. Programs used by those in the art to evaluate codon optimization include those provided by Integrated DNA Technologies, EnCor Biotechnology, Inc., JCat, OptimumGene™ (GenScript USA, Inc., Pisataway, N.J. 08854), etc. The sequences encoding the CAR embodiments described herein may be codon-optimized, which can increase their translational efficiency.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence.

Generally, operably linked DNA sequences are contiguous and, where necessary to join two protein coding regions, in the same reading frame.

The term "overexpressed" or "overexpression" is intended to indicate an abnormal level of expression (e.g., of the tumor antigen) in a cell from a disease area (e.g., a solid tumor within a specific tissue or organ of the patient) relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In some embodiments, the patient, subject or individual is a human. In some embodiments, the patient, subject or individual is a child (such as 18 years of age or younger).

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner. A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds" or "specific for", as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "subject" is intended to include living organisms in which an immune response can be elicited (e.g., mammals). Examples of subjects include humans, dogs, cats, mice, rats, and transgenic species thereof.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Compositions

In some embodiments, the present invention provides a chimeric antigen receptor (CAR) comprising (a) an extracellular domain comprising an antigen binding domain, (b) a transmembrane domain and (c) a cytoplasmic domain. It should be appreciated that in some embodiments, CAR molecules described by the following exemplary, non-limiting arrangements are from left to right, N-terminus to C-terminus of the CAR. A CAR molecule as described by the disclosure may comprise or further comprise any other combination of elements as described herein.

In some embodiments, a CAR as described by the disclosure is fully human. In some embodiments, a CAR has a cytoplasmic domain comprising, a IL-15Rα cytoplasmic domain in combination with one or more other cytoplasmic domains described herein, e.g., a CD3 zeta domain. In some embodiments, the arrangement of the elements of a CAR is selected from one of the following exemplary, non-limiting arrangements:
scFv-CD28-IL-15Rα-CD3z
scFv-CD28-CD27-IL-15Rα-CD3z
scFv-CD28-(4-1BB)-CD27-IL-15Rα-CD3z
scFv-CD8-CD27-IL-15Rα-CD3z
scFv-CD8-(4-1BB)-CD27-IL-15Rα-CD3z In some embodiments, a CAR has a cytoplasmic domain comprising, a CD27 cytoplasmic domain in combination with one or more other cytoplasmic domains described herein, e.g., a 4-1BB intracellular domain and/or a CD3 zeta domain. In some embodiments, the cytoplasmic domain further comprises a safety-enhancing domain, e.g., an apoptosis-inducing iCasp9-FKBP domain. In some embodiments, the arrangement of the elements of a CAR is selected from one of the following exemplary, non-limiting arrangements:
scFv-CD28-(4-1BB)-CD27-CD3z-iCasp9-FKBP
scFv-CD28-CD27-(4-1BB)-CD3z-iCasp9-FKBP
scFv-CD8-(4-1BB)-CD27-CD3z-iCasp9-FKBP
scFv-CD8-CD27-(4-1BB)-CD3z-iCasp9-FKBP In some embodiments, a CAR described by the disclosure comprises an antigen binding domain specific for GD2. In some embodiments, the arrangement of the elements of the CAR is selected from one of the following exemplary, non-limiting arrangements:
GD2scFv-CD28-(4-1BB)-CD27-CD3z
GD2scFv-CD8-CD28-CD3z
GD2scFv-CD28-(4-1BB)-CD27-CD3z-Casp9-FKBP
GD2scFv-CD8-CD28-CD3z-Casp9-FKBP Between the extracellular domain (comprising the antigen binding domain) and the transmembrane domain of the CAR, or between the cytoplasmic domain and the transmembrane domain of the CAR, there may be incorporated a spacer or hinge domain. As used herein, the term "spacer domain" generally means any oligo- or polypeptide that functions to link the transmembrane domain to the extracellular domain and/or the cytoplasmic domain in the polypeptide chain. As used herein, a hinge domain generally means any oligo- or polypeptide that functions to provide flexibility to the CAR, or domains thereof, and/or prevent steric hindrance of the CAR, or domains thereof. In some embodiments, a spacer or hinge domain may comprise up to 300 amino acids, preferably 10 to 100 amino acids and most preferably 5 to 20 amino acids. It also should be appreciated that one or more spacer domains may be included in other regions of a CAR, as aspects of the disclosure are not limited in this respect.

It is to be understood that a CAR can include a region (e.g., an antigen binding domain, a transmembrane domain, a cytoplasmic domain, a signaling domain, a safety domain, and/or a linker, or any combination thereof) having a sequence provided herein or a variant thereof or a fragment of either one thereof (e.g., a variant and/or fragment that retains the function required for the CAR activity) can be included in a CAR protein as described herein. In some embodiments, a variant has 1, 2, 3, 4, 5, 6, 7, 8, 9, or 10 amino acid changes relative to the illustrated sequence. In some embodiments, a variant has a sequence that is at least 80%, at least 85%, at least 90%, 90%-95%, at least 95% or at least 99% identical to the illustrated sequence. In some embodiments, a fragment is 1-5, 5-10, 10-20, 20-30, 30-40, or 40-50 amino acids shorter than a sequence provided herein. In some embodiments, a fragment is shorter at the N-terminal, C-terminal, or both terminal regions of the sequence provided. In some embodiments, a fragment contains 80%-85%, 85%-90%, 90%-95%, or 95%-99% of the number of amino acids in a sequence provided herein.

In some embodiments, the spacer and/or hinge sequences of the CAR are selected from one or more of the following exemplary sequences:
Spacer Sequences:

```
                                        (SEQ ID NO: 1)
    GGGGS (SEQ ID NO: 2)
    GGGGSGGGGS (SEQ ID NO: 3)
    GGGGS x3

GS18:
                                        (SEQ ID NO: 4)
    GSTSGGGSGGGSGGGGSS

218S:
                                        (SEQ ID NO: 5)
    GSTSGSGKPGSSEGSTKG

GS8:
                                        (SEQ ID NO: 6)
    GGGGSGGG
```

Hinge Sequences:

```
    Native:
                                        (SEQ ID NO: 7)
    VEPKSCDKTHTCPPCP C233S:
                                        (SEQ ID NO: 8)
    LDPKSSDKTHTCPPCP C233P:
                                        (SEQ ID NO: 9)
    VEPKSPDKTHTCPPCP Delta5:
                                        (SEQ ID NO: 10)
    LDKTHTCPPCP
```

Antigen Binding Domains

In some embodiments, the CAR of the invention comprises an antigen binding domain. The choice of binding domain depends upon the type and number of ligands that define the surface of a target cell. For example, the antigen binding domain may be chosen to recognize a ligand that acts as a cell surface marker on target cells associated with a particular disease state, such as cancer or an autoimmune disease. Thus examples of cell surface markers that may act as ligands for the antigen binding domain in the CAR of the invention include those associated with cancer cells and other forms of diseased cells, for example, autoimmune disease cells and pathogen infected cells. In some embodiments, the CAR of the invention is engineered to target a tumor antigen of interest by way of engineering a desired antigen binding domain that specifically binds to an antigen on a tumor cell. In the context of the present invention, "tumor antigen" refers to antigens that are common to specific hyperproliferative disorders such as cancer. The antigens discussed herein are merely included by way of example. The list is not intended to be exclusive and further examples will be readily apparent to those of skill in the art.

The antigen binding domain of the CAR may target, for example, CD19, CD30, or GD2. Other examples of target antigens include, but are not limited to, CD2, CD5, CD7, CD10, CD19, CD20, CD22, CD30, CD33, CD38, CD52, CD56, CD74, CD138, CD317, Her2, VEGFR2, EGFRviii, CXCR4, BCMA, GD2, GD3, and any other antigens overexpressed in target or diseased cells. Other antigens specific for cancer that may be targeted at taught in PCT publication No. WO2013/123061 (page 20), which is incorporated herein by reference with respect to the antigens recited therein.

The antigen binding domain can be any domain that binds to the antigen including but not limited to monoclonal antibodies, scFvs, polyclonal antibodies, synthetic antibodies, human antibodies, humanized antibodies, and fragments thereof. In some instances, it is beneficial for the antigen binding domain to be derived from the same species in which the CAR will ultimately be used in. For example, for use in humans, it may be beneficial for the antigen binding domain of the CAR to comprise a human antibody or fragment thereof. Thus, in some embodiments, the antigen binding domain comprises a human antibody or a fragment thereof.

An antigen binding domain (e.g., an scFV) that "specifically binds" to a target or an epitope is a term understood in the art, and methods to determine such specific binding are also known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antigen binding domain (e.g., an scFV) that specifically binds to GD2 or an epitope therein is an antibody that binds this target antigen with greater affinity, avidity, more readily, and/or with greater duration than it binds to other antigens or other epitopes in the same antigen. It is also understood by reading this definition that, for example, an antigen binding domain (e.g., an scFV) that specifically binds to a first target antigen may or may not specifically bind to a second target antigen. As such, "specific binding" does not necessarily require (although it can include) exclusive binding. Generally, but not necessarily, reference to binding means specific binding. In some embodiments, antigen binding domains (e.g., scFVs) described herein have a suitable binding affinity to GD2. As used herein, "binding affinity" refers to the apparent association constant or $K_A$. The $K_A$ is the reciprocal of the dissociation constant ($K_D$). The antibody described herein may have a binding affinity ($K_A$) of at least $10^5$, $10^6$, $10^7$, $10^8$, $10^9$, $10^{10}$ M, or higher. An increased binding affinity corresponds to a decreased $K_D$. Higher affinity binding of an antibody to a first target relative to a second target can be indicated by a higher $K_A$ (or a smaller numerical value $K_D$) for binding the first target than the $K_A$ (or numerical value $K_D$) for binding the second target. In such cases, the antibody has specificity for the first target relative to the second target. Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in, e.g., TRIS-buffer (50 mM TRIS, 150 mM NaCl, 5 mM CaCl2 at pH7.5). These techniques can be used to measure the concentration of bound binding protein as a function of target protein concentration. The concentration of bound binding protein ([Bound]) is related to the concentration of free target protein ([Free]) and the concentration of binding sites for the binding protein on the target where (N) is the number of binding sites per target molecule by the following equation:

$$[Bound]=[N][Free]/(Kd+[Free])$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, W098/16654, WO 96/34096, WO 96/33735, and WO91/10741; each of which is incorporated herein by reference in its entirety. A human antibody can also be an antibody wherein the heavy and light chains are encoded by a nucleotide sequence derived from one or more sources of human DNA. Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention.

Antibodies directed against an antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For a detailed discussion of this technology for producing human antibodies and human monoclonal antibodies and protocols for producing such antibodies, see, e.g., PCT Publication Nos. WO2014/055771, WO 98/24893, WO 96/34096, and WO 96/33735; and U.S. Pat. Nos. 5,413,923; 5,625,126; 5,633,425; 5,569, 825; 5,661,016; 5,545,806; 5,814,318; and 5,939,598, each of which is incorporated by reference herein in their entirety.

A "humanized" antibody retains a similar antigenic specificity as the original antibody, i.e., in the present invention, the ability to bind an antigen described herein, for example, CD19, CD30, or GD2.

In some embodiments, the antigen binding domain of the CAR of the invention targets CD19. In some embodiments, the antigen binding moiety portion in the CAR of the invention is a fully human anti-CD19 scFV. In some embodiments, the anti-CD19 scFV comprises the sequence below, or the complementarity determining regions (CDRs, underlined below and numbered CDR1-3) contained within the sequence below.

Exemplary CD19 scFv:

```
Light chain:
                                                 (SEQ ID NO: 11)
DIQMTQTTSSLSASLGDRVTISC RASQDISKYLN (CDR 1)

WYQQKPDGTVKLLIY HTSRLHS (CDR2)

GVPSRFSGSGSGTDYSLTISNLEQEDIATYFC QQGNTLPYT (CDR3)

FGGGTKLEIT

Heavy chain:
                                                 (SEQ ID NO: 12)
EVKLQESGPGLVAPSQSLSVTCTVSGVSLP DYGVS (CDR1)

WIRQPPRKGLEWLG VIWGSETTY (CDR2)

YNSALKSRLTIIKDNSKSQVFLKMNSLQTDDTAIYYCAK

HYYYGGSYAMDY (CDR3) WGQGTSVTVSS
```

In some embodiments, the antigen binding domain of the CAR of the disclosure targets CD30. In some embodiments, the antigen binding moiety portion in the CAR of the disclosure is a fully human anti-CD30 scFV. In some embodiments, the anti-CD30 scFV comprises a sequence below, or the complementarity determining regions (CDRs, underlined below and numbered CDR1-3) contained within the sequences below:

Exemplary CD30 scFvs:

```
AC10 scFv Light chain:
                                                 (SEQ ID NO: 13)
DIVMTQSPDSLAVSLGERATINC KASQSVDFDGDSYMN (CDR1)

WYQQKPGQPPKLLIY AASNLES (CDR2)

GVPDRFSGSGSGTDFTLTISSLQAEDVAVYYCQQSNEDPWT (CDR3) FGQGTKVEIK

AC10 scFv Heavy chain:
                                                 (SEQ ID NO: 14)
VHQIQLVQSGAEVKKPGASVKVSCKAS GYTFTDYYIT (CDR1)

WVRQAPGQGLEWMG WIYPGSGNTKYNEKFKG (CDR2)

RVTMTRDTSISTAYMELSRLRSDDTAVYYCANYGNYWFAY (CDR3)

WGQGTLVTVSS

5F11 scFv Light Chain:
                                                 (SEQ ID NO: 15)
DIQMTQSPTSLSASVGDRVTITC RASQGISSWLT (CDR1) WYQQKPEKAPKSLIY

AASSLQS (CDR2)
GVPSRFSGSGSGTDFTLTISSLQPEDFATYYCQQYDSYPIT (CDR3)
FGQGTRLEIK

5F11 scFv Heavy Chain:
                                                 (SEQ ID NO: 16)
QVQLQQWGAGLLKPSETLSLTCAVYGGSFS AYYWS (CDR1) WIRQPPGKGLEWIG

DINHGGGTNYNPSLKS (CDR2)

RVTISVDTSKNQFSLKLNSVTAADTAVYYCASLTAY (CDR3) WGQGSLVTVSS
```

In some embodiments, the antigen binding domain of the CAR of the invention is specific for GD2. In some embodiments, the antigen binding moiety portion in the CAR of the invention is an anti-GD2 scFV, such as a fully human anti-GD2 scFV. In some embodiments, the anti-GD2 scFV comprises the sequence(s) of the light and/or heavy chain variable regions of hu3F8, c.60C3 or hu14.18, or the complementarity determining regions (CDRs) contained within the light and/or heavy chain variable regions of hu3F8, c.60C3 or hu14.18 (see, e.g., Yu, A. L., et al., Anti-GD2 antibody with GM-CSF, interleukin-2, and isotretinoin for neuroblastoma. N Engl J Med, 2010. 363(14): p. 1324-34; Ahmed, M. and N. K. Cheung, Engineering anti-GD2 monoclonal antibodies for cancer immunotherapy. FEBS Lett, 2014. 588(2): p. 288-97; and Alvarez-Rueda, N., et al., Binding activities and antitumor properties of a new mouse/human chimeric antibody specific for GD2 ganglioside antigen. Clin Cancer Res, 2007. 13(18 Pt 2): p. 5613s-5620s). In some embodiments, the anti-GD2 scFV comprises the variable heavy chain (VH) and variable light chain (VL) sequences below, or the complementarity determining regions (CDRs, underlined below) contained within the sequences below.

Exemplary GD2 scFV:

VH: (CDR regions underlined)
(SEQ ID NO: 17)
QVQLVESGPGVVQPGRSLRISCAVSGFSVT NYGVH WVRQPPGKGLEWLG

VIWAGGITNYNSAFMS RLTISKDNSKNTVYLQMNS LRAEDTAMYYCAS

RGGHYGYALDY WGQGTLVTVSS

VL: (CDR regions underlined)
(SEQ ID NO: 18)
EIVMTQTPATLSVSAGERVTITC KASQSVSNDVT WYQQKPGQAPRLLIY

SASNRYS GVPARFSGSGYGTEFTFTISSVQSEDFAVYFC QQDYSS

FGQGTKLEIK

Other exemplary_anti-GD2 scFV sequences are shown below with an exemplary 218S linker sequence underlined.

hu3F8 scFv: (VH and VL linked by 218S linker)
(SEQ ID NO: 19)
QVQLVESGPGVVQPGRSLRISCAVSGFSVTNYGVHWVRQPPGKGLEWLGVIW

AGGITNYNSAFMSRLTISKDNSKNTVYLQMNSLRAEDTAMYYCASRGGHYGY

ALDYWGQGTLVTVSSGSTSGSGKPGSSEGSTKGEIVMTQTPATLSVSAGERV

TITCKASQSVSNDVTWYQQKPGQAPRLLIYSASNRYSGVPARFSGSGYGTEF

TFTISSVQSEDFAVYFCQQDYSSFGQGTKLEIK

C60c3 ScFv: (VH and VL linked by 218S linker)
(SEQ ID NO: 20)
EVKLVESGGGLVLPGDSLRLSCATSEFTFTDYYMTWVRQPPRKALEWLGFIR

NRANGYTTEYNPSVKGRFTISRDNSQSILYLQMNTLRTEDSATYYCARVSNW

AFDYWGQGTTLTVSSGSTSGSGKPGSSEGSTKGDVVMTQTPLSLPVSLGDQA

SISCRSSQSLLKNNGNTFLHWYLQKSGQSPKLLIYKVSNRLSGVPDRFSGSG

SGTYFTLKISRVEAEDLGVYFCSQSTH1PYTFGGGTKLEIK

Hu14.18 scFv:: (VH and VL linked by 218S linker)
(SEQ ID NO: 21)
EVQLVQSGAEVEKPGASVKISCKASGSSFTGYNMNWVRQNIGKSLEWIGAID

PYYGGTSYNQKFKGRATLTVDKSTSTAYMHLKSLRSEDTAVYYCVSGMEYWG

QGTSVTVSSGSTSGSGKPGSSEGSTKGDVVMTQTPLSLPVTPGEPASISCRS

SQSLVHRNGNTYLHWYLQKPGQSPKLLIHKVSNRFSGVPDRFSGSGSGTDFT

LKISRVEAEDLGVYFCSQSTHVPPLTFGAGTKLELK

Further Extracellular Domain

In some embodiments, the CAR is designed to include an extracellular T cell co-stimulatory domain such as CD28 extracellular domain, or a portion thereof. The extracellular domain may serve as a hinge domain or T cell activation domain. Examples include the CD28 extracellular domain, which has 50 amino acids. An exemplary sequence of the CD28 extracellular domain is:

(SEQ ID NO: 22)
YVNQTDIYFCKIEVMYPPPYLDNEKSNGTIIHVKGKHLCPSPLFPGPSKP.

Transmembrane Domain

With respect to the transmembrane domain, the CAR can be designed to comprise a transmembrane domain that is fused to the extracellular domain (e.g., the antigen binding domain) of the CAR. Any transmembrane domain is contemplated for use herein as long as the domain is capable of anchoring a CAR comprising the domain to a cell membrane. In some embodiments, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex. One skilled in the art would appreciate that the full transmembrane domain, or portion thereof, is implemented with the cytoplasmic domain, or a portion thereof. Typically, the transmembrane and cytoplasmic domains used would be contiguous portions of the CD28 sequence.

The transmembrane domain may be derived either from a natural or from a synthetic source. Where the source is natural, the domain may be derived from any membrane-bound or transmembrane protein. Transmembrane domains of particular use in this invention may be derived from (e.g., comprise at least the transmembrane domain(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, and CD154. Transmembrane domains can be identified using any method known in the art or described herein, e.g., by using the UniProt Database.

In some embodiments, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In some embodiments, the transmembrane domain in the CAR of the invention is the CD8 transmembrane domain. Sequences of CD8 for this purposes are taught in PCT pub no. WO2014/055771.

In some embodiments, the transmembrane domain in the CAR of the invention is a CD28 transmembrane domain. An exemplary sequence of CD28 is provided below, as well as an exemplary transmembrane domain sequence. In some embodiments, the CD28 transmembrane domain comprises the exemplary transmembrane domain sequence below, or a fragment or variant thereof that is capable of anchoring a CAR comprising the sequence to a cell membrane.

```
CD28 (amino acids 19-220)
                                        (SEQ ID NO: 23)
NKILVKQSPMLVAYDNAVNLSCKYSYNLFSREFRASLHKGLDSAVEVC

VVYGNYSQQLQVYSKTGFNCDGKLGNESVTFYLQNLYVNQTDIYFCKI

EVMYPPPYLDNEKSNGTIIHVKGKHLCPSPLFPGPSKPFWVLVVVGGV

LACYSLLVTVAFIIFWVRSKRSRLLHSDYMNMTPRRPGPTRKHYQPYA

PPRDFAAYRS

CD28 (amino acids 153-179, transmembrane domain)
                                        (SEQ ID NO: 24)
FWVLVVVGGVLACYSLLVTVAFIIFWV
```

In some embodiments, the CAR of the invention is comprises a region of CD28 that contains all or part of an extracellular domain, all or part of a transmembrane domain and all or part of a cytoplasmic domain. An exemplary sequence of a region of CD28 for inclusion in a CAR is provided below. In some embodiments, the CD28 transmembrane domain comprises the exemplary transmembrane domain sequence below, or a fragment or variant thereof that is capable of anchoring a CAR comprising the sequence to a cell membrane.

```
CD28 region
                                        (SEQ ID NO: 25)
IEVMYPPPYLDNEKSNGTIIHVKGKHLCPSPLFPGPSKPFWVLVVVGG

VLACYSLLVTVAFIIFWVRSKRSRLLHSDYMNMTPRRPGPTRKHYQPY

APPRDFAAYRSAS
```

In some embodiments, the transmembrane domain of the CAR of the invention comprises a hinge domain such as a CD8 hinge domain. An exemplary CD8 hinge domain sequence is provided below. In some embodiments, the CD8 hinge domain comprises the exemplary sequence below, or a fragment or variant thereof that is capable of providing flexibility to or preventing steric hindrance of the CAR or the domain(s) attached to the hinge domain. In some instances, a variety of human hinges can be employed as well including the human Ig (immunoglobulin) hinge.

```
CD8 hinge domain
                                        (SEQ ID NO: 26)
AKPTTTPAPRPPTPAPTIASQPLSLRPEACRPAAGGAVHTRGLDFACD
```

Cytoplasmic Domain

In some embodiments, the cytoplasmic domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire domain. To the extent that a truncated portion of the intracellular signaling domain is used, such truncated portion may be used in place of the intact domain as long as it transduces the effector function signal. The term intracellular signaling domain is thus meant to include any truncated portion of the intracellular signaling domain sufficient to transduce the effector function signal.

In some embodiments, the cytoplasmic domain comprises an IL-15Rα cytoplasmic domain. In some embodiments, the intracellular IL-15Rα cytoplasmic domain displays effector signaling function that enhances immune effector activities including, but not limited to cell proliferation and cytokine production. An exemplary IL-15Rα cytoplasmic domain sequence is provided below. In some embodiments, the IL-15Rα cytoplasmic domain comprises the exemplary sequence below, or a fragment or variant thereof that, when included in a CAR, has the same or an improved function (such as cytolytic activity, cell proliferation or secretion of cytokines) compared to a CAR comprising the exemplary sequence below. The function may be tested using a method provided herein, such as the method provided in Example 1.

```
IL-15Rα intracellular domain
                                        (SEQ ID NO: 27)
KSRQTPPLASVEMEAMEALPVTWGTSSRDEDLENCSHHL
```

In some embodiments, the cytoplasmic domain comprises a CD27 intracellular domain (e.g., CD27 cytoplasmic domain). In some embodiments, the intracellular CD27 cytoplasmic domain displays effector signaling function that enhances immune effector activities including, but not limited to cell proliferation and cytokine production. An exemplary CD27 cytoplasmic domain sequence is provided below. In some embodiments, the CD27 cytoplasmic domain comprises the exemplary sequence below, or a fragment or variant thereof that, when included in a CAR, has the same or an improved function (such as cytolytic activity, cell proliferation or secretion of cytokines) compared to a CAR comprising the exemplary sequence below. The function may be tested using any suitable method known in the art.

```
CD27 intracellular domain
                                        (SEQ ID NO: 38)
QRRKYRSNKGESPVEPAEPCHYSCPREEEGSTIPIQEDYRKPEPACSP
```

Examples of other intracellular signaling domains for use in the CAR of the invention include the cytoplasmic sequences of the T cell receptor (TCR) and co-receptors that act in concert to initiate signal transduction following antigen receptor engagement, as well as any fragment or variant of these sequences and any synthetic sequence that has the same functional capability.

It is known that signals generated through the endogenous TCR alone are insufficient for full activation of the T cell and that a secondary or co-stimulatory signal is also required. Thus, T cell activation can be mediated by two distinct classes of cytoplasmic signaling sequences: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3zeta. Exemplary CD3 zeta domain sequences are provided below. In some embodiments, the CD3zeta signaling domain comprises one of the exemplary sequences below, or a fragment or variant thereof that, when included in a CAR, has the same or an improved function (such as cytolytic activity or secretion of cytokines) compared to a CAR comprising the exemplary sequence below. The function may be tested using a method provided herein, such as the method provided in Example 1.

```
CD3 zeta signaling domain
                                       (SEQ ID NO: 39)
RVKFSRSADAPAYKQGQNQLYNELNLGRREEYDVLDKRRGRDPEMGGK

PRRKNPQEGLYNELQKDKMAEAYSEIGMKGERRRGKGHDGLYQGLSTA

TKDTYDALHMQALPPR

CD3 zeta signaling domain
                                       (SEQ ID NO: 40)
RVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTA

TKDTYDALHMQALPPR
```

The cytoplasmic domain of the CAR can be designed to comprise a CD3-zeta signaling domain combined with any other desired cytoplasmic domain(s) useful in the context of the CAR of the invention. For example, the cytoplasmic domain of the CAR can comprise a CD3 zeta domain and a costimulatory signaling region. The costimulatory signaling region refers to a portion of the CAR comprising the intracellular domain of a costimulatory molecule. Thus, while the invention in exemplified primarily with 4-1BB, CD28, and CD27 as the co-stimulatory signaling element, other additional costimulatory elements are within the scope of the invention. Exemplary co-stimulatory signaling regions include 4-1BB, CD21, CD28, CD27, CD127, ICOS, IL-15Rα, and OX40.

In some embodiments, the cytoplasmic domain of a CAR can be designed to comprise an IL-15Rα cytoplasmic domain and a CD3-zeta signaling domain combined with any other desired cytoplasmic domain(s) useful in the context of the CAR of the invention. For example, the cytoplasmic domain of the CAR can comprise an IL-15Rα cytoplasmic domain, a CD3 zeta domain and a costimulatory signaling region. The costimulatory signaling region refers to a portion of the CAR comprising the intracellular domain of a costimulatory molecule. Thus, while the invention in exemplified primarily with 4-1BB, CD28, CD137 and CD27 as the co-stimulatory signaling element, other additional costimulatory elements are within the scope of the invention.

The cytoplasmic domain of the CAR can be designed to comprise CD27 cytoplasmic domain and a CD3-zeta signaling domain combined with any other desired cytoplasmic domain(s) useful in the context of the CAR of the disclosure. For example, the cytoplasmic domain of the CAR can comprise CD27 cytoplasmic domain, a CD3 zeta domain and a costimulatory signaling region. The costimulatory signaling region refers to a portion of the CAR comprising the intracellular domain of a costimulatory molecule. Thus, while the disclosure is exemplified primarily with IL-15Rα, 4-1BB, CD28, CD137 and CD27 as the co-stimulatory signaling element, other additional costimulatory elements are within the scope of the disclosure. Example sequences of co-stimulatory signaling regions are shown below.

```
CD28 (amino acids 180-220, cytoplasmic domain)
                                       (SEQ ID NO: 41)
RSKRSRLLHSDYMNMTPRRPGPTRKHYQPYAPPRDFAAYRS 4-1BB (CD137) intracellular TRAF binding domain
                                       (SEQ ID NO: 42)
KRGRKKLLYIFKQPFMRPVQTTQEEDGCSCRFPEEEEGGCEL ICOS intracellular domain
                                       (SEQ ID NO: 43)
CWLTKKKYSSSVHDPNGEYMFMRAVNTAKKSRLTDVTL OX40 intracellular domain
                                       (SEQ ID NO: 44)
ALYLLRRDQRLPPDAHKPPGGGSFRTPIQEEQADAHSTLAKI CD27 intracellular domain
                                       (SEQ ID NO: 38)
QRRKYRSNKGESPVEPAEPCHYSCPREEEGSTIPIQEDYRKPEPACSP CD127 intracellular domain
                                       (SEQ ID NO: 45)
KRIKPIVWPSLPDHKKTLEHLCKKPRKNLNVSFNPESFLDCQIHRVDD

IQARDEVEGFLQDTFPQQLEESEKQRLGGDVQSPNCPSEDVVITPESF

GRDSSLTCLAGNVSACDAPILSSSRSLDCRESGKNGPHVYQDLLLSLG

TTNSTLPPPFSLQSGILTLNPVAQGQPILTSLGSNQEEAYVTMSSFYQ

NQ

IL-15Rα intracellular domain
                                       (SEQ ID NO: 27)
KSRQTPPLASVEMEAMEALPVTWGTSSRDEDLENCSHHL
```

In some embodiments, CAR of the invention comprises the apoptosis inducing gene Casp9 or a domain or truncated version thereof. An exemplary Casp9 sequence and truncated sequence is below. In some embodiments, the CAR comprises a 2A peptide linker between a CD3 zeta domain and Casp9.

```
CASP9 amino acid sequence
                                       (SEQ ID NO: 28)
MDEADRRLLRRCRLRLVEELQVDQLWDALLSRELFRPHMIEDIQRAGS

GSRRDQARQLIIDLETRGSQALPLFISCLEDTGQDMLASFLRTNRQAA

KLSKPTLENLTPVVLRPEIRKPEVLRPETPRPVDIGSGGFGDVGALES

LRGNADLAYILSMEPCGHCLIINNVNFCRESGLRTRTGSNIDCEKLRR

RFSSLHFMVEVKGDLTAKKMVLALLELAQQDHGALDCCVVVILSHGCQ

ASHLQFPGAVYGTDGCPVSVEKIVNIFNGTSCPSLGGKPKLFFIQACG

GEQKDHGFEVASTSPEDESPGSNPEPDATPFQEGLRTFDQLDAISSLP
```

-continued
TPSDIFVSYSTFPGFVSWRDPKSGSWYVETLDDIFEQWAHSEDLQSLL

LRVANAVSVKGIYKQMPGCFNFLRKKLFFKTS

A truncated CASP9 amino acid sequence
(SEQ ID NO: 29)
VGALESLRGNADLAYILSMEPCGHCLIINNVNFCRESGLRTRTGSNID

CEKLRRRFSSLHFMVEVKGDLTAKKMVLALLELAQQDHGALDCCVVVI

LSHGCQASHLQFPGAVYGTDGCPVSVEKIVNIFNGTSCPSLGGKPKLF

FIQACGGEQKDHGFEVASTSPEDESPGSNPEPDATPFQEGLRTFDQLD

AISSLPTPSDIFVSYSTFPGFVSWRDPKSGSWYVETLDDIFEQWAHSE

DLQSLLLRVANAVSVKGIYKQMPGCFNFLRKKLFFKTS

In some embodiments, the CAR further comprises a mutated FK506 binding protein (e.g., FKBPf36v) motif. An exemplary mutated FK506 binding protein motif is provided below.

FKBP f36v amino acid sequence
(SEQ ID NO: 30)
MGVQVETISPGDGRTFPKRGQTCVVHYTGMLEDGKKVDSSRDRNKPFK

FMLGKQEVIRGWEEGVAQMSVGQRAKLTISPDYAYGATGHPGIIPPHA

TLVFDVELLKLE

The cytoplasmic signaling sequences within the cytoplasmic signaling portion of the CAR of the invention may be linked to each other in a random or specified order. Optionally, a short oligo- or polypeptide linker or spacer, preferably between 5 and 20 amino acids in length may be inserted between cytoplasmic domains. A GGGGS (SEQ ID NO: 1) or (GGGGS)×3 (SEQ ID NO: 3) provides a particularly suitable linker.

In some embodiments, a CAR comprises or consists of the sequence below, which is broken down by exemplary domains included therein (domain names appear in bold after each domain in the exemplary CARs):

(CD19 scFv domain)
DIQMTQTTSSLSASLGDRVTISCRASQDISKYLNWYQQKPDGTVKLLI

YHTSRLHSGVPSRFSGSGSGTDYSLTISNLEQEDIATYFCQQGNTLPY

TFGGGTKLEITGSTSGSGKPGSGEGSTKGEVKLQESGPGLVAPSQSLS

VTCTVSGVSLPDYGVSWIRQPPRKGLEWLGVIWGSETTYYNSALKSRL

TIIKDNSKSQVFLKMNSLQTDDTAIYYCAKHYYYGGSYAMDYWGQGTS

VTVSSAA (CD28 transmembrane/cytoplasmic domain)
IEVMYPPPYLDNEKSNGTIIHVKGKHLCPSPLFPGPSKPFWVLVVVGG

VLACYSLLVTVAFIIFWVRSKRSRLLHSDYMNMTPRRPGPTRKHYQPY

APPRDFAAYRSAS (Linker)
GGGGSGGGGS (IL-15Ralpha cytoplasmic signal domain)
KSRQTPPLASVEMEAMEALPVTWGTSSRDEDLENCSHHL (Linker)
GGGGSGGGGS (CD3zeta signal domain)
(SEQ ID NO: 31)
RVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTA

TKDTYDALHMQALPPR

In some embodiments, a CAR comprises or consists of the sequence below, which is broken down by exemplary domains included therein (domain names appear in bold after each domain in the exemplary CARs):

(CD30 scFv domain)
QVQLQQWGAGLLKPSETLSLTCAVYGGSFSAYYWSWIRQPPGKGLEWI

GDINHGGGTNYNPSLKSRVTISVDTSKNQFSLKLNSVTAADTAVYYCA

SLTAYWGQGSLVTVSS (Linker)
GSTSGSGKPGSSEGSTKG (CD30 scFv domain)
DIQMTQSPTSLSASVGDRVTITCRASQGISSWLTWYQQKPEKAPKSLI

YAASSLQSGVPSRFSGSGSGTDFTLTISSLQPEDFATYYCQQYDSYPI

TFGQGTRLEIK (Linker)
GSTSGSGKPGSSEGSTKG (CD28 transmembrane domain)
FWVLVVVGGVLACYSLLVTVAFIIFWV (4-1BB intracellular domain)
KRGRKKLLYIFKQPFMRPVQTTQEEDGCSCRFPEEEEGGCEL (CD27 intracellular domain)
QRRKYRSNKGESPVEPAEPCHYSCPREEEGSTIPIQEDYRKPEPACSP (Linker)
GSTSGSGKPGSSEGSTKG (CD3 zeta domain)
RVKFSRSADAPAYKQGQNQLYNELNLGRREEYDVLDKRRGRDPEMGGK

PRRKNPQEGLYNELQKDKMAEAYSEIGMKGERRRGKGHDGLYQGLSTA

TKDTYDALHMQALPPR (Linker)
GSTSGSGKPGSSEGSTKG (truncated iCasp9 domain)
VGALESLRGNADLAYILSMEPCGHCLIINNVNFCRESGLRTRTGSNID

CEKLRRRFSSLHFMVEVKGDLTAKKMVLALLELAQQDHGALDCCVVVI

LSHGCQASHLQFPGAVYGTDGCPVSVEKIVNIFNGTSCPSLGGKPKLF

FIQACGGEQKDHGFEVASTSPEDESPGSNPEPDATPFQEGLRTFDQLD

AISSLPTPSDIFVSYSTFPGFVSWRDPKSGSWYVETLDDIFEQWAHSE

DLQSLLLRVANAVSVKGIYKQMPGCFNFLRKKLFFKTS (FKBP domain)
(SEQ ID NO: 32)
MGVQVETISPGDGRTFPKRGQTCVVHYTGMLEDGKKVDSSRDRNKPFK

FMLGKQEVIRGWEEGVAQMSVGQRAKLTISPDYAYGATGHPGIIPPHA

TLVFDVELLKLE

In some embodiments, the above exemplary, non-limiting arrangements are from left to right, N-terminus to C-terminus of the CAR. The CAR may comprise or further comprise any other combination of elements as described herein.

In some embodiments, a CAR comprises or consists of one the exemplary sequences below, which is broken down by exemplary domains included therein (domain names appear in bold after each domain in the exemplary CARs):

CAR 1
(GD2 scFv heavy chain)
QVQLVESGPGVVQPGRSLRISCAVSGFSVTNYGVHWVRQPPGKGLEWL

GVIWAGGITNYNSAFMSRLTISKDNSKNTVYLQMNSLRAEDTAMYYCA

SRGGHYGYALDYWGQGTLVTVSSASTKGPSVFPLAPSSKSTSGGTAAL

GCLVKDYFPEPVTVSWNSGALTSGVHTFPAVLQSSGLYSLSSVVTVPS

SSLGTQTYICNVNHKPSNTKVDKRVEPKSCDKTHTCPPCPAPELLGGP

SVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEK

TISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHE

ALHNHYTQKSLSLSPGK (218S Linker)
GSTSGSGKPGSSEGSTKG (GD2 scFv light chain)
EIVMTQTPATLSVSAGERVTITCKASQSVSNDVTWYQQKPGQAPRLLI

YSASNRYSGVPARFSGSGYGTEFTFTISSVQSEDFAVYFCQQDYSSFG

QGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACE

VTHQGLSSPVTKSFNRGEC (CD28 transmembrane domain)
GSTSGSGKPGSSEGSTKGFWVLVVVGGVLACYSLLVTVAFIIFWV (4-1BB intracellular domain)
KRGRKKLLYIFKQPFMRPVQTTQEEDGCSCRFPEEEEGGCEL (CD27 intracellular domain)
QRRKYRSNKGESPVEPAEPCHYSCPREEEGSTIPIQEDYRKPEPACSP (218S Linker)
GSTSGSGKPGSSEGSTKG (CD3zeta)
RVKFSRSADAPAYKQGQNQLYNELNLGRREEYDVLDKRRGRDPEMGGK

PRRKNPQEGLYNELQKDKMAEAYSEIGMKGERRRGKGHDGLYQGLSTA

TKDTYDALHMQALPPR (218S Linker)
GSTSGSGKPGSSEGSTKG (truncated Casp9 domain)
VGALESLRGNADLAYILSMEPCGHCLIINNVNFCRESGLRTRTGSNID

CEKLRRRFSSLHFMVEVKGDLTAKKMVLALLELAQQDHGALDCCVVVI

LSHGCQASHLQFPGAVYGTDGCPVSVEKIVNIFNGTSCPSLGGKPKLF

FIQACGGEQKDHGFEVASTSPEDESPGSNPEPDATPFQEGLRTFDQLD

AISSLPTPSDIFVSYSTFPGFVSWRDPKSGSWYVETLDDIFEQWAHSE

DLQSLLLRVANAVSVKGIYKQMPGCFNFLRKKLFFKTS (FKBP domain)
(SEQ ID NO: 33)
MGVQVETISPGDGRTFPKRGQTCVVHYTGMLEDGKKVDSSRDRNKPFK

FMLGKQEVIRGWEEGVAQMSVGQRAKLTISPDYAYGATGHPGIIPPHA

TLVFDVELLKLE

CAR 2
(VH hu3F8)
QVQLVESGPGVVQPGRSLRISCAVSGFSVTNYGVHWVRQPPGKGLEWL

GVIWAGGITNYNSAFMSRLTISKDNSKNTVYLQMNSLRAEDTAMYYCA

SRGGHYGYALDYWGQGTLVTVSS (218S Linker)
GSTSGSGKPGSSEGSTKG (VL hu3F8)
EIVMTQTPATLSVSAGERVTITCKASQSVSNDVTWYQQKPGQAPRLLI

YSASNRYSGVPARFSGSGYGTEFTFTISSVQSEDFAVYFCQQDYSSFG

QGTKLEIK (CD28 transmembrane domain)
FWVLVVVGGVLACYSLLVTVAFIIFWV (4-1BB intracellular domain)
KRGRKKLLYIFKQPFMRPVQTTQEEDGCSCRFPEEEEGGCEL (CD27 intracellular domain)
QRRKYRSNKGESPVEPAEPCHYSCPREEEGSTIPIQEDYRKPEPACSP (218S Linker)
GSTSGSGKPGSSEGSTKG (CD3zeta)
RVKFSRSADAPAYKQGQNQLYNELNLGRREEYDVLDKRRGRDPEMGGK

PRRKNPQEGLYNELQKDKMAEAYSEIGMKGERRRGKGHDGLYQGLSTA

TKDTYDALHMQALPPR (218S Linker)
GSTSGSGKPGSSEGSTKG (truncated Casp9)
VGALESLRGNADLAYILSMEPCGHCLIINNVNFCRESGLRTRTGSNID

CEKLRRRFSSLHFMVEVKGDLTAKKMVLALLELAQQDHGALDCCVVVI

LSHGCQASHLQFPGAVYGTDGCPVSVEKIVNIFNGTSCPSLGGKPKLF

FIQACGGEQKDHGFEVASTSPEDESPGSNPEPDATPFQEGLRTFDQLD

AISSLPTPSDIFVSYSTFPGFVSWRDPKSGSWYVETLDDIFEQWAHSE

DLQSLLLRVANAVSVKGIYKQMPGCFNFLRKKLFFKTS (FKBP domain)
(SEQ ID NO: 34)
MGVQVETISPGDGRTFPKRGQTCVVHYTGMLEDGKKVDSSRDRNKPFK

FMLGKQEVIRGWEEGVAQMSVGQRAKLTISPDYAYGATGHPGIIPPHA

TLVFDVELLKLE

CAR 3
(VH C60c3)
EVKLVESGGGLVLPGDSLRLSCATSEFTFTDYYMTWVRQPPRKALEWL

GFIRNRANGYTTEYNPSVKGRFTISRDNSQSILYLQMNTLRTEDSATY

YCARVSNWAFDYWGQGTTLTVSS

-continued (218S Linker)
GSTSGSGKPGSSEGSTKG (VL C60c3)
DVVMTQTPLSLPVSLGDQASISCRSSQSLLKNNGNTFLHWYLQKSGQS

PKLLIYKVSNRLSGVPDRFSGSGSGTYFTLKISRVEAEDLGVYFCSQS

THIPYTFGGGTKLEIK (CD28 transmembrane domain)
FWVLVVVGGVLACYSLLVTVAFIIFWV (4-1BB intracellular domain)
KRGRKKLLYIFKQPFMRPVQTTQEEDGCSCRFPEEEEGGCEL (CD27 intracellular domain)
QRRKYRSNKGESPVEPAEPCHYSCPREEEGSTIPIQEDYRKPEPACSP (218S Linker)
GSTSGSGKPGSSEGSTKG (CD3zeta)
RVKFSRSADAPAYKQGQNQLYNELNLGRREEYDVLDKRRGRDPEMGGK

PRRKNPQEGLYNELQKDKMAEAYSEIGMKGERRRGKGHDGLYQGLSTA

TKDTYDALHMQALPPR (218S Linker)
GSTSGSGKPGSSEGSTKG (truncated Casp9)
VGALESLRGNADLAYILSMEPCGHCLIINNVNFCRESGLRTRTGSNID

CEKLRRRFSSLHFMVEVKGDLTAKKMVLALLELAQQDHGALDCCVVVI

LSHGCQASHLQFPGAVYGTDGCPVSVEKIVNIFNGTSCPSLGGKPKLF

FIQACGGEQKDHGFEVASTSPEDESPGSNPEPDATPFQEGLRTFDQLD

AISSLPTPSDIFVSYSTFPGFVSWRDPKSGSWYVETLDDIFEQWAHSE

DLQSLLLRVANAVSVKGIYKQMPGCFNFLRKKLFFKTS (FKBP domain)
(SEQ ID NO: 35)
MGVQVETISPGDGRTFPKRGQTCVVHYTGMLEDGKKVDSSRDRNKPFK

FMLGKQEVIRGWEEGVAQMSVGQRAKLTISPDYAYGATGHPGIIPPHA

TLVFDVELLKLE

CAR 4
(VH Hu14.18)
EVQLVQSGAEVEKPGASVKISCKASGSSFTGYNMNWVRQNIGKSLEWI

GAIDPYYGGTSYNQKFKGRATLTVDKSTSTAYMHLKSLRSEDTAVYYC

VSGMEYWGQGTSVTVSS (218S Linker)
GSTSGSGKPGSSEGSTKG (VL Hu14.18)
DVVMTQTPLSLPVTPGEPASISCRSSQSLVHRNGNTYLHWYLQKPGQS

PKLLIHKVSNRFSGVPDRFSGSGSGTDFTLKISRVEAEDLGVYFCSQS

THVPPLTFGAGTKLELK (CD28 transmembrane domain)
FWVLVVVGGVLACYSLLVTVAFIIFWV (4-1BB intracellular domain)
KRGRKKLLYIFKQPFMRPVQTTQEEDGCSCRFPEEEEGGCEL (CD27 intracellular domain)
QRRKYRSNKGESPVEPAEPCHYSCPREEEGSTIPIQEDYRKPEPACSP -continued
(218S Linker)
GSTSGSGKPGSSEGSTKG (CD3zeta)
RVKFSRSADAPAYKQGQNQLYNELNLGRREEYDVLDKRRGRDPEMGGK

PRRKNPQEGLYNELQKDKMAEAYSEIGMKGERRRGKGHDGLYQGLSTA

TKDTYDALHMQALPPR (218S Linker)
GSTSGSGKPGSSEGSTKG (truncated Casp9)
VGALESLRGNADLAYILSMEPCGHCLIINNVNFCRESGLRTRTGSNID

CEKLRRRFSSLHFMVEVKGDLTAKKMVLALLELAQQDHGALDCCVVVI

LSHGCQASHLQFPGAVYGTDGCPVSVEKIVNIFNGTSCPSLGGKPKLF

FIQACGGEQKDHGFEVASTSPEDESPGSNPEPDATPFQEGLRTFDQLD

AISSLPTPSDIFVSYSTFPGFVSWRDPKSGSWYVETLDDIFEQWAHSE

DLQSLLLRVANAVSVKGIYKQMPGCFNFLRKKLFFKTS (FKBP domain)
(SEQ ID NO: 36)
MGVQVETISPGDGRTFPKRGQTCVVHYTGMLEDGKKVDSSRDRNKPFK

FMLGKQEVIRGWEEGVAQMSVGQRAKLTISPDYAYGATGHPGIIPPHA

TLVFDVELLKLE

In some embodiments, the above exemplary, non-limiting arrangements are from left to right, N-terminus to C-terminus of the CAR. The CAR may comprise or further comprise any other combination of elements as described herein.

Vectors

In some embodiments, the present invention encompasses a DNA construct comprising sequences of a CAR, wherein the sequence comprises the nucleic acid sequence of an antigen binding domain operably linked to the nucleic acid sequence of transmembrane domain and a cytoplasmic domain. An exemplary cytoplasmic domain that can be used in a CAR of the invention includes but is not limited to the cytoplasmic domain of IL-15Rα and the signaling domain of CD3-zeta. In some embodiments, a CAR comprises the intracellular domain of CD28, 4-1BB, and/or CD27 and the signaling domain of CD3-zeta. In some instances, a CAR can further comprise the apoptosis inducing gene Casp9.

In some embodiments, the arrangement of the elements of the CAR is selected from one of the following exemplary, non-limiting arrangements:
scFv-CD28-IL-15Rα-CD3z
scFv-CD28-CD27-IL-15Rα-CD3z
scFv-CD28-(4-1BB)-CD27-IL-15Rα-CD3z
scFv-CD8-CD27-IL-15Rα-CD3z
scFv-CD8-(4-1BB)-CD27-IL-15Rα-CD3z
scFv-CD28-(4-1BB)-CD27-CD3z-iCasp9-FKBP
scFv-CD28-CD27-(4-1BB)-CD3z-iCasp9-FKBP
scFv-CD8-(4-1BB)-CD27-CD3z-iCasp9-FKBP
scFv-CD8-CD27-(4-1BB)-CD3z-iCasp9-FKBP
GD2scFv-CD28-(4-1BB)-CD27-CD3z
GD2scFv-CD8-CD28-CD3z
GD2scFv-CD28-(4-1BB)-CD27-CD3z-Casp9-FKBP
GD2scFv-CD8-CD28-CD3z-Casp9-FKBP In some embodiments, the above exemplary, non-limiting arrangements are from left to right, N-terminus to C-terminus of the CAR. The CAR may comprise or further comprise any other combination of elements as described herein.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lenti viral vectors have the added advantage over vectors derived from onco-retroviruses such as murine leukemia viruses in that they can transduce non-proliferating cells, such as hepatocytes. They also have the added advantage of low immunogenicity. In another embodiment, the desired CAR can be expressed in the cells by way of transposons.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration into eukaryotes. Typical cloning vectors contain transcription and translation terminators, initiation sequences, and promoters useful for regulation of the expression of the desired nucleic acid sequence. The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, retrovirus vectors are used. A number of retrovirus vectors are known in the art. In some embodiments, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Factor-1a (EF-1a). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. In some embodiments, the promoter is a EF-1a promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like, and fluorescent genes such as GFP, YFP, RFP and the like. In some embodiments, reporter genes or selectable marker genes are excluded from a CAR polypeptide used in a therapy as described herein.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity, antibiotic resistance or fluorescence. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means. In some embodiments, the host cell is a T cell.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

RNA Transfection

In some embodiments, the genetically modified T cells of the invention are modified through the introduction of RNA (e.g., an mRNA comprises a sequence encoding a CAR as described herein). In some embodiments, an in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is the CAR of the present invention. For example, in some embodiments, the template for the RNA CAR comprises an extracellular domain comprising an anti-CD19 scFv; a transmembrane domain (such as the transmembrane domain of CD28); and a cytoplasmic domain comprises the signaling domain of CD3-zeta and the cytoplasmic domain of IL-15Rα. In some embodiments, the template for the RNA CAR comprises an extracellular domain comprising an anti-CD30 scFv; a transmembrane domain (such as the transmembrane domain of CD28); and a cytoplasmic domain comprises a CD27 intracellular domain, a 4-1BB intracellular domain, and the signaling domain of CD3-zeta. In some embodiments, the template for the RNA CAR comprises an extracellular domain comprising an anti-GD2 scFv; a transmembrane domain (such as the transmembrane domain of CD28); and a cytoplasmic domain comprises a CD27 intracellular domain, a 4-1BB intracellular domain, and the signaling domain of CD3-zeta.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Genetically Modified Immune Cells

In some embodiments, the CAR sequence(s) (e.g., nucleic acid sequences encoding a CAR as described herein) are delivered into cells (e.g., T cells or NK cells) using a retroviral or lentiviral vector. In some embodiments, the arrangement of the elements of the CAR encoded by the CAR sequence(s) is selected from one of the following exemplary, non-limiting arrangements:

scFv-CD28-IL-15Rα-CD3z
scFv-CD28-CD27-IL-15Rα-CD3z
scFv-CD28-(4-1BB)-CD27-IL-15Rα-CD3z
scFv-CD8-CD27-IL-15Rα-CD3z
scFv-CD8-(4-1BB)-CD27-IL-15Rα-CD3z
scFv-CD28-(4-1BB)-CD27-CD3z-iCasp9-FKBP
scFv-CD28-CD27-(4-1BB)-CD3z-iCasp9-FKBP
scFv-CD8-(4-1BB)-CD27-CD3z-iCasp9-FKBP
scFv-CD8-CD27-(4-1BB)-CD3z-iCasp9-FKBP
GD2scFv-CD28-(4-1BB)-CD27-CD3z
GD2scFv-CD8-CD28-CD3z
GD2scFv-CD28-(4-1BB)-CD27-CD3z-Casp9-FKBP
GD2scFv-CD8-CD28-CD3z-Casp9-FKBP In some embodiments, the above exemplary, non-limiting arrangements are from left to right, N-terminus to C-terminus of the CAR. The CAR may comprise or further comprise any other combination of elements as described herein.

CAR-expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In another embodiment, the desired CAR can be expressed in the cells (e.g., T cells or NK cells) by way of transposons.

The disclosed methods can be applied to the modulation of immune cell (e.g., T cell or NK cell) activity in basic research and therapy, in the fields of cancer, stem cells, acute and chronic infections, and autoimmune diseases, including the assessment of the ability of the genetically modified T cell or NK cell to kill a target cell, e.g., a target cancer cell.

The methods also provide the ability to control the level of expression over a wide range by changing, for example, the promoter or the amount of input vector, making it possible to individually regulate the expression level. For example, varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

Sources of Immune Cells

Prior to expansion and genetic modification of the immune cells (e.g., T cells) of the invention, a source of immune cells (e.g., T cells) is obtained from a subject. Immune cells (e.g., T cells) can be obtained from a number of sources, including peripheral blood mononuclear cells, bone marrow, lymph node tissue, cord blood, thymus tissue, tissue from a site of infection, ascites, pleural effusion, spleen tissue, and tumors. The immune cells (e.g., T cells) may also be generated from induced pluripotent stem cells or hematopoietic stem cells or progenitor cells. In some embodiments of the present invention, any number of immune cell lines, including but not limited to T cell and NK cell lines, available in the art, may be used. In some embodiments of the present invention, immune cells (e.g., T cells) can be obtained from a unit of blood collected from a subject using any number of techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, NK cells, other nucleated white blood cells, red blood cells, and platelets. In some embodiments, the cells collected by apheresis may be washed to remove the plasma fraction and to place the cells in an appropriate buffer or media for subsequent processing steps. In some embodiments of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, immune cells (e.g., T cells) are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$T cells, can be further isolated by positive or negative selection techniques. For example, in some embodiments, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In some embodiments, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD1 1b, CD16, HLA-DR, and CD8. In certain embodiments, it may be desirable to enrich for or positively select for regulatory T cells which typically express CD4+, CD25+, CD62L$^{hi}$, GITR+, and FoxP3+.

Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in some embodiments, a concentration of 2 billion cells/ml is used. In some embodiments, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In some embodiments, the concentration of cells used is $5 \times 10^6$/ml. In other embodiments, the concentration used can be from about $1 \times 10^5$/ml to $1 \times 10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen. In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In some embodiments a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, Cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after genetic modification of the T cells to express a desirable CAR, the T cells can be activated and expanded generally using methods as described, for example, in U.S. Pat. Nos. 6,352,694 and 6,534,055.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9): 13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In some embodiments, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In some embodiments, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In some embodiments, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In some embodiments, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In some embodiments, a ratio of particles to cells of 1:1 or less is used. In one particular embodiment, a preferred particle:cell ratio is 1:5. In further embodiments, the ratio of particles to cells can be varied depending on the day of stimulation. For example, in some embodiments, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In some embodiments the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in some embodiments, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In some embodiments of the present invention, the mixture may be cultured for several hours (about 3 hours) to about 14 days or any hourly integer value in between. In another embodiment, the mixture may be cultured for 21 days. In some embodiments of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFNγ, IL-4, IL-7, GM-CSF, IL-10, IL-12, IL-15, TGFp, and TNF-a or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population (¾, CD4+) that is greater than the cytotoxic or suppressor T cell population ($T_c$, CD8+). Ex vivo expansion of T cells by stimulating CD3 and CD28 receptors produces a population of T cells that prior to about days 8-9 consists predominately of ¾ cells, while after about days 8-9, the population of T cells comprises an increasingly greater population of Tc cells. Accordingly, depending on the purpose of treatment, infusing a subject with a T cell population comprising predominately of $T_H$ cells may be advantageous. Similarly, if an antigen-specific subset of Tc cells has been isolated it may be beneficial to expand this subset to a greater degree.

Further, in addition to CD4 and CD 8 markers, other phenotypic markers vary significantly, but in large part, reproducibly during the course of the cell expansion process. Thus, such reproducibility enables the ability to tailor an activated T cell product for specific purposes.

Therapeutic Application

In some embodiments, the present invention provides a cell (e.g., T cell) modified to express a CAR comprises an antigen binding domain, a transmembrane domain (such as CD28 transmembrane domain), and a cytoplasmic domain comprising an IL-15Rα cytoplasmic domain, optionally combined with CD3-zeta and/or any other cytoplasmic domains described herein. In some embodiments, a cell is modified to express a CAR comprising an antigen binding domain, a transmembrane domain (such as CD28 transmembrane domain), and a cytoplasmic domain having a CD27 intracellular domain and a 4-1BB intracellular domain, optionally combined with CD3-zeta and/or any other cytoplasmic domains (e.g., an iCasp9-FKBP domain) described herein. In some embodiments, a cell is modified to express a CAR comprising an antigen binding domain (e.g., a scFV specific for GD2), a transmembrane domain (such as CD28 transmembrane domain), and a cytoplasmic domain. Therefore, in some instances, the transduced T cell can elicit a CAR-mediated T-cell response.

In some embodiments, the invention provides the use of a CAR to redirect the specificity of a primary T cell to an antigen, such as a tumor antigen. Thus, in some embodiments, the present invention also provides a method for stimulating a T cell-mediated immune response to a target cell population or tissue in a mammal comprising the step of administering to the mammal a T cell that expresses a CAR, wherein the CAR comprises an antigen binding domain (e.g., CD19 scFV), a transmembrane domain (such as CD28 transmembrane domain), and a cytoplasmic domain comprising an IL-15Rα cytoplasmic domain, optionally combined with CD3-zeta and/or any other cytoplasmic domains described herein.

In some embodiments, a method for stimulating a T cell-mediated immune response to a target cell population or tissue in a mammal comprising the step of administering to the mammal a T cell that expresses a CAR, wherein the CAR comprises an antigen binding domain (e.g., CD30 scFV), a transmembrane domain (such as CD28 transmembrane domain), and a cytoplasmic domain having a CD27 intracellular domain and a 4-1BB intracellular domain, optionally combined with CD3-zeta and/or any other cytoplasmic domains (e.g., iCasp9 domain and FKBP domain) described herein.

In some embodiments, the disclosure provides a method for stimulating a T cell-mediated immune response to a target cell population or tissue in a mammal comprising the step of administering to the mammal a T cell that expresses a CAR, wherein the CAR comprises an antigen binding domain (e.g., GD2 scFV), a transmembrane domain (such as CD28 transmembrane domain), and a cytoplasmic domain (e.g., comprising a CD28, 4-1BB, and/or CD27 intracellular domain combined with CD3-zeta and/or any other cytoplasmic domains described herein.

In some embodiments, the present invention includes a type of cellular therapy where T cells are genetically modified to express a CAR and the CAR T cell is infused to a recipient in need thereof. The infused cell is able to kill cells expressing the antigen, e.g., tumor cells, in the recipient. Unlike antibody therapies, CAR T cells are able to replicate in vivo resulting in long-term persistence that can lead to sustained tumor control.

In some embodiments, the CAR T cells of the invention can undergo robust in vivo T cell expansion and can persist for an extended amount of time.

While the data disclosed herein specifically disclose lentiviral vector comprising (1) anti-CD19 scFv, a CD28 transmembrane domain, a IL-15Rα cytoplasmic domain and a CD3-zeta signaling domain, (2) anti-CD30 scFv, a CD28 transmembrane domain, a cytoplasmic domain having a CD27 intracellular domain and a 4-1BB intracellular domain, and a CD3-zeta signaling domain, and (3) anti-GD2 scFv, a CD28 transmembrane domain, a cytoplasmic domain having a CD27 intracellular domain and a 4-1BB intracellular domain, and a CD3-zeta signaling domain, the invention should be construed to include any number of variations for each of the components of the construct as described elsewhere herein. That is, the invention includes the use of any antigen binding domain in the CAR to generate a CAR-mediated T-cell response specific to the antigen binding domain. For example, the antigen binding domain in the CAR of the invention can target a tumor antigen for the purposes of treat cancer.

In some embodiments, the antigen bind domain portion of the CAR of the invention is designed to treat a particular cancer. For example, the CAR may be designed to target CD19 for treating B cell malignancies, or CD30 for treating Hodgkin's lymphoma or certain T cell lymphoma, or GD2 for treating small cell neuroendocrine cancer or small cell lung cancer, and neuronal cancer.

The CAR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (e.g., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells. In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised, such as individuals having cancer.

The CAR-modified immune cells (e.g., CAR T cells) of the present invention may be administered either alone, or as a composition (e.g., a pharmaceutical composition) in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants {e.g., aluminum hydroxide); and preservatives.

Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the CAR-modified immune cells (e.g., CAR T cells) described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319: 1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated immune (e.g., T cells) to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In some embodiments, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

In certain embodiments of the present invention, cells activated and expanded using the methods described herein, or other methods known in the art where T cells are expanded to therapeutic levels, or any other compositions described herein, are administered to a patient in conjunction with (e.g., before, simultaneously or following) any number of relevant treatment modalities, including checkpoint inhibitors, such as PD-L1 inhibitors or PD1 inhibitors. In some embodiments, the PD-L1 inhibitors or PD1 inhibitors are PD-L1-specific antibodies or PD1-specific antibodies. Exemplary checkpoint inhibitors include, e.g., pembrolizumab (Merck), ipilimumab (Bristol-Myers Squibb), nivolumab (Bristol-Myers Squibb), MPDL3280A (Roche), MEDI4736 (AstraZeneca), MEDI0680 (AstraZeneca), BMS-936559/MDX-1105 (Bristol-Myers Squibb) and MSB0010718C (Merck). Other PD-L1 and PD1 inhibitors are known in the art (see, e.g., Dolan et al. PD-1 pathway inhibitors: changing the landscape of cancer immunotherapy. Cancer Control. 2014 July; 21(3):231-7). In some embodiments, compositions described herein are administered in conjunction with (e.g., before, simultaneously or following) chemotherapy and/or radiotherapy.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766). Strategies for CAR T cell dosing and scheduling have been discussed (Ertl et al, 2011, Cancer Res, 71:3175-81; Junghans, 2010, Journal of Translational Medicine, 8:55).

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

Interleukin 15Rα as Co-Stimulatory Domain in CD19 CART Cells Enhances the Anti-Leukemia Efficacy Chimeric Antigen Receptor T cells (CARTs) are engineered T cells displaying specificity against tumor antigens, usually based on one or more single chain Fv (scFv) antibody moieties. The initial CAR design consisted of a receptor complex that combined an antigen binding single chain antibody Fv domain (scFv) and a signal transduction domain of T cells (usually CD3ζ) {Eshhar Z, 1993, Specific activation and targeting of cytotoxic lymphocytes through chimeric single chains consisting of antibody-binding domains and gamma or zeta subunits of the immunoglobulins or T cell receptors}. These so called first generation CARs have only limited anti-tumor activities and in vivo survival {Kowolik CM1, 2006, CD28 costimulation provided through a CD19-specific chimeric antigen receptor enhances in vivo persistence and antitumor efficacy of adoptively transferred T cells; Hwu P1, 1995, In vivo antitumor activity of T cells redirected with chimeric antibody/T-cell receptor genes.}. In order to enhance killing efficacy and persistence of CARTs, several second and third generation CARs with the addition of one or two co-stimulatory signals such as CD28 and 4-1BB have been generated {Kowolik CM1, 2006, CD28 costimulation provided through a CD19-specific chimeric antigen receptor enhances in vivo persistence and antitumor efficacy of adoptively transferred T cells; Savoldo B, 2011, CD28 costimulation improves expansion and persistence of chimeric antigen receptor-modified T cells in lymphoma patients; Song D G, 2011, In vivo persistence', tumor localization', and antitumor activity of CAR-engineered T cells is enhanced by costimulatory signaling through CD137 (4-1BB); Milone M C, 2009, Chimeric receptors containing CD137 signal transduction domains mediate enhanced survival of T cells and increased antileukemic efficacy in vivo.}.

CD19 has proved to be an effective tumor antigen to target B cell malignancies using CARTs. The first success with CD19 targeting CARTs was reported in chronic lymphocytic leukemia patients and adults with refractory B cell leukemias {Porter D L, 2011, Chimeric antigen receptor-modified T cells in chronic lymphoid leukemia; Brentjens R J, 2013, CD19-targeted T cells rapidly induce molecular remissions in adults with chemotherapy-refractory acute lymphoblastic leukemia.}. The field is moving extremely fast and recently found to be useful in pediatric acute B cell leukemia {Grupp S A, 2013, Chimeric Antigen Receptor-Modified T cells for Acute Lymphoid Leukemia.}. Preliminary results of CD19 targeted CART clinical trials indicate that this therapy is effective in various settings including post hematopoietic stem cell transplant relapsed leukemia using donor T cells engineered with CD19-CAR {Cruz C R, 2013, Infusion of donor-derived CD19-redirected virus-specific T cells for B-cell malignancies relapsed after allogeneic stem cell transplant: a phase 1 study; Brentjens R J, 2011, Safety and persistence of adoptively transferred autologous CD19-targeted T cells in patients with relapsed or chemotherapy refractory B-cell leukemias; Kochenderfer J N, 2013, Donor-derived CD19-targeted T cells cause regression of malignancy persisting after allogeneic hematopoietic stem cell transplantation.}.

Results of the CART clinical trials conducted so far indicate that several factors may be influencing the performance of CARTs including those related to disease, patient-related factors and last but not least, CART characteristics. The current focus is on generating CARTs with increased efficacy, longer survival and a good safety profile so that they can be applied to a wider range of malignancies including solid tumors which harbor a hostile tumor microenvironment {Maus M V, 2014, Antibody-modified T cells: CARs take the front seat for hematologic malignancies; CJ., 2014, Chimeric antigen receptor modified T cell therapy for B cell malignancies.}. One of the ways this can be accomplished is by potentiating CAR signaling and activation of the genetically modified T cells.

Interleukin-15 (IL-15) is a T cell growth factor which shares many similarities with the more ubiquitously known interleukin-2 (IL-2) {Steel, 2012, Interleukin-15 biology and its therapeutic implications in cancer}. It has a trimeric receptor consisting of an IL-15Rα chain which is unique to IL-15 and the IL-15β (commonly designated as IL-2/15β) along with common gamma chain (γC) which it shares with IL-2. Both these interleukins are involved in T cell growth, expansion, activation and survival, but there are specific differences between the two. Most importantly, IL-15 does not cause activation induced cell death (AICD) unlike IL-2 {Munger, 1995, Studies evaluating the antitumor activity and toxicity of interleukin-15', a new T cell growth factor: comparison with interleukin-2; Marks-Konczalik, 2000, IL-2-induced activation-induced cell death is inhibited in IL-15 transgenic mice}. IL-15 is required for differentiation of NK cells, CD8 cells and maintain memory phenotype CD8 cells which is the main defense mechanism against cancer cells {Jakobisiak, 2011, Interleukin 15 as a promising candidate for tumor immunotherapy}. Its receptor IL-15Rα is involved in high affinity binding of IL-15 which presents it to IL-2/IL-15βγ which in turn leads to the signaling mediated through various pathways including JAK1/3 and STAT3/5 pathways {Budagian, 2006, IL-15/IL-15 receptor biology: a guided tour through an expanding universe; Okada, 2015, STAT3 signaling contributes to the high effector activities of interleukin-15-derived dendritic cells}.

To increase the efficacy of CARTs, extra co-stimulatory and cytokine signaling domains were incorporated to obtain advanced generation of CARs, abrogating the need to administer additional cytokines along with the CART infusion. Based on this approach, a fourth generation CAR was developed with CD27 co-stimulatory domain in addition to CD28 and 4-1BB signaling domains and its therapeutic efficacy was tested in leukemia and lymphoma patients. The study herein reports a novel CAR design incorporating the IL-15Rα-signaling domain and the comparison of the new CAR with both the $3^{rd}$ (19z, with 4-1BB and CD28 domains) and the $4^{th}$ generation CARs (273z, with 4-1BB, CD27 and CD28 domains). The study herein demonstrates that with the addition of IL-15Rα signaling, the CARTs displayed rapid expansion and target killing activities, which could translate into high therapeutic efficacy against B cell malignancies.

Materials and Methods

Cell lines and culture media. RS4;11 and MV4-11 were CD19 positive acute lymphoblastic leukemia and CD19 negative acute mono-myelocytic leukemia cell lines, respectively, which were obtained from American Type Culture Collection (ATCC). Jurkat T cells were purchased from ATCC. All cell lines were maintained in RPMI1640 medium (Life Technologies, Inc., Grand Island, N.Y.) with 10% fetal bovine serum (FBS, Atlanta Biologicals, Inc. Norcross, Ga.) and supplemented with penicillin (100 units) and streptomycin (100 µg). Target cancer cell lines were transduced with lentiviral vectors expressing a green fluorescent protein (wasabi GFP) and the reporter gene positive cells were sorted by flow cytometry. Jurkat T cells were transduced with lentiviral CAR vectors and the copy number of CAR per cell was determined by quantitative PCR using genomic DNA.

Blood donors and primary T cell culture. Buffy coats from anonymous healthy donors (HDs) were purchased from LifeSouth Civitan Blood Center (Gainesville, Fla., USA). PBMCs were isolated from buffy coats by gradient density centrifugation in Ficoll-Hypaque (GE Healthcare Bio-Sciences AB, Piscataway, N.J., USA) as previously described {Chang, 1995, Infection and replication of Tat-human immunodeficiency viruses: genetic analyses of LTR and tat mutations in primary and long-term human lymphoid cells}. Blood and bone marrow samples of children with newly diagnosed acute lymphoblastic leukemia were obtained with the assistance of a Hematological Malignancies Bank. T cells were activated using anti-CD3 and anti-CD28 antibody-conjugated magnetic beads or phytohemagglutinin (PHA). The T cells were maintained in TexMACS medium (Miltenyi Biotec Inc, San Diego, Calif.) supplemented with interleukin-2, -7 and -15 as previously described {Okada, 2015 #33}. Phenotype of the activated cells was verified to confirm T cell purity. After expansion for two to six days, the T cells were transduced with lentiviral CAR vectors.

Lentivector Construction and CAR Gene Transduction.

Lentivectors were generated using the NHP/TYF lentivector system as previously described {Chang, 2005 #181; Wang, 2006 #19}. CAR DNA was chemically synthesized and cloned into pTYF transducing vector behind human EF1α promoter. The final lenti-CAR vectors were verified by restriction enzyme mapping and DNA sequencing.

qPCR Determination of CAR Copies in CARTs.

The CAR transgene copy numbers in CARTs were determined by quantitative SYBR green real time PCR (qRT-PCR) as previously described {Okada, 2015 #33}. Genomic DNA was harvested from CARTs using Promega Wizard genomic DNA purification kit (Promega Corp. Madison, Wis.). Conditions for the qRT-PCR reaction was conducted as suggested by SABioscience using the MX3000P qPCR system (Stratagene, Agilent Technologies, Santa Clara, Calif.).

Calcein AM Labeling of Target Cells.

Fresh or thawed leukemia cells obtained from patients were first washed with RPMI. Then $1 \times 10^6$ cells were suspended in 196 µl of RPMI1640 in a non-attachment tube and 4 µl of 20 µM Calcein AM (Life Technologies Corp) was added to get a final concentration of 0.4 µM. The cells were then incubated at 37° C. for 1 hour and subsequently washed twice with RPMI1640 with FBS before using for co-culture experiments.

CART Killing Assay.

Target cells and CARTs were counted using tryptan blue staining and a hemocytometer. The cells were co-cultured in 96U plate in effector:target ratios of 1-2:1, or as indicated in each experiment. CART numbers ranged from $5 \times 10^4$ to $2 \times 10^5$. The coculture was incubated in TexMACS medium without cytokines. Cells were incubated for 1-2 hours and overnight for short term assays. CART-targeted killing was recorded by quantitative analysis of the shifted side scattered (SSC) population, and early and late apoptotic (annexin V-stained) and Propidium Iodide (PI)-stained (dead) cells {Zhang, 1997, Early detection of apoptosis using a fluorescent conjugate of annexin V}. Samples were run in the LSRII flow cytometer using the DiVa software (BD Biosciences) and results were analyzed using the FlowJo software.

Annexin V and PI Staining for Apoptosis.

After 1 to 2 hours of incubation, cells were transferred to 96-V plate and centrifuged at 400 g for 5 minutes to remove the media. Then the cell pellet was washed with PBS once. Cells were re-suspended in 30 µl of staining mix consisting of 0.25 µl PI (Sigma), 0.5 µl Annexin V (BD Bioscience) and 29.25 µl of binding buffer (BD Bioscience) and then incubated in the dark for 15 min at room temperature. Subsequently, cells are suspended in 200 µl FACS buffer and analyzed in the LSRII flow cytometer using DiVa software (BD Biosciences). Results were evaluated using FlowJo software.

CFSE Cell Proliferation Assay.

$1 \times 10^5$ CARTs were first washed with PBS and then re-suspended in 100 µl of PBS. A working solution of CFSE was prepared in PBS to get a final concentration of 10 µM. Then 100 µl of this was added to the cell suspension to get a final CFSE concentration of 5 µM. The cells were incubated at 37 C in the dark for 15 minutes. Then the cells were washed twice with cold RPMI+10% FBS and again once with Texsmacs medium. These cells were co-cultured with RS4;11 in a effector to target ratio of 1:5 and incubated in the dark at 37 C. For positive control, CFSE labeled T cells were stimulated with anti-CD3 and anti-CD28 Abs with cytokine medium, and for negative control, CFSE labeled T cells were treated with mitomycin C. The cells were analyzed by flow for proliferation indicated by CFSE dilution on Day 2 or 3 after surface staining for CD3 to gate the T cells only.

Monoclonal Antibodies (mAbs).

Fluorochrome-conjugated mAbs against human IFNγ (B27, APC), IL-2 (MQ1-17H12, PE) CD8 (SK1, APC-Cy7), CD4 (RPA-T4, PB), CD22 (S-HCL-1, APC), CD27 (M-T271, APC), CD28 (L-293, PerCp-Cy5.5), CD34 (8G12, PE-Cy7), PD1 (EH12.1, PE-Cy7), and CD107a (H4A3, FITC) were purchased from BD Biosciences (San Diego, Calif.). Anti-CD19 mAb (SJ25C1, PE) was purchased from Caltag laboratories (Life technologies Inc) and anti-CD127 mAb (RDR5, APC-eflour) was purchased from eBiosciences.

Surface Staining and Intracellular Cytokine Staining.

For effector functional analysis, the CARTs were mixed with target in E/T ratio of 1:3 overnight with the addition of 1.50 of FITC-conjugated anti-CD107a Ab. Positive control used T cells (without CAR) stimulated with PMA (1 µg/µl) and Ionomysin (1 µg/µl) for 1 hour. The intracellular cytokines were immobilized using monensin (6 µg/µl) for 6 hours. The samples were then washed, blocked with 10% human and mouse sera for 30 min, stained with anti-CD4 and anti-CD8 Abs for 30 min, fixed and permeabilized with BD Fix/Perm Buffer, stained with anti-IFNγ and anti-IL-2 Abs for 1 hour, and then analyzed by flow cytometry. Data was collected on the BD LSRII flow cytometer and analyzed with Flowjo.

Effector Cytokine Analysis Using Cytokine Bead Array.

The BD CBA™ Human Soluble Protein Flex Set System was used to detect concentrations of cytokines IL-2, IL-6, TNFα and IFNγ in the supernatants collected from the CART killing assays on day 1 or 2 of incubation. The CBA system captures a soluble analyte or set of analytes with beads of known size and fluorescence, making it possible to detect analytes using flow cytometry. Each capture bead was coated with a capture antibody specific for a soluble protein. The detection reagent was a mixture of PE-conjugated Abs, which provided a fluorescent signal in proportion to the amount of bound analyte. First 10 tubes of 50 µl set standard dilutions were prepared. Then 50 µl of each unknown sample was added to an assay tube. 50 µl of the mixed capture beads was added to each assay tube and incubated at room temperature for 1 hr. Then 50 µl of the PE detection reagent was added and incubated for 2 hr at room temperature. 1 ml of wash buffer was added to each tube and centrifuged at 200 g for 5 minutes. After the supernatant was removed, 300 µl of wash buffer was added and vortexed prior to acquiring the results on flow cytometer.

CAR Gene Sequence:

The amino acid sequence of the IL-15Rα CD19 CAR tested in this study is as follows, broken down by the domains included in the CAR:

DIQMTQTTSSLSASLGDRVTISCRASQDISKYLNWYQQKPDGTVKLLIYHTS

RLHSGVPSRFSGSGSGTDYSLTISNLEQEDIATYFCQQGNTLPYTFGGGTKL

EITGSTSGSGKPGSGEGSTKGEVKLQESGPGLVAPSQSLSVTCTVSGVSLPD

YGVSWIRQPPRKGLEWLGVIWGSETTYYNSALKSRLTIIKDNSKSQVFLKMN

SLQTDDTAIYYCAKHYYYGGSYAMDYWGQGTSVTVSSAA (CD19 scFv domain)

IEVMYPPPYLDNEKSNGTIIHVKGKHLCPSPLFPGPSKPFWVLVVVGGVLAC

YSLLVTVAFIIFWVRSKRSRLLHSDYMNMTPRRPGPTRKHYQPYAPPRDFAA

YRSAS (CD28 transmembrane/cytoplasmic domain)

GGGGSGGGGS (linker)

KSRQTPPLASVEMEAMEALPVTWGTSSRDEDLENCSHHL (IL-15R acytoplasmic signal domain)

GGGGSGGGGS (linker)

(SEQ ID NO: 31)
RVKFSRSADAPAYQQGQNQLYNELNLGRREEYDVLDKRRGRDPEMGGKPRRK

NPQEGLYNELQKDKMAEAYSEIGMKGERRRGKGHDGLYQGLSTATKDTYDAL

HMQALPPR (CD3zeta signal domain)

Results

Construction of CARs Containing Various Co-Stimulatory Signaling Domains

The CD19 CAR (19z) sequence was codon optimized and chemically synthesized based on the anti-CD19 scFv of mouse hybridoma FMC63 {Nicholson, 1997, Construction and characterization of a functional CD19 specific single chain Fv fragment for immunotherapy of B lineage leukaemia and lymphoma}. Briefly, the parental 19z CAR (3$^{rd}$ generation) contained a chimeric intracellular signaling element derived from CD28 trans-membrane and cytoplasmic domain, the co-stimulatory 4-1BB intracellular TRAF binding domain and the CD3ζ chain intracellular domain, analogous to the CAR design of Kochenderfer et al. {Kochenderfer, 2009, Construction and preclinical evaluation of an anti-CD19 chimeric antigen receptor}. To establish new generation CARs, the co-stimulatory domains of various immune modulatory receptors were incorporated into the CAR construct including the cytoplasmic domains of CD27 (273z), OX40 (OX40z), ICOS (ICOSz), and IL-15Rα (153z). These CARs were cloned into the lentiviral vector pTYF and packaged with NHP/VSVG lentivector system as illustrated in FIG. 1.

Development of a Simplified Killing Assay for Functional Evaluation of CARs

Figure 2:
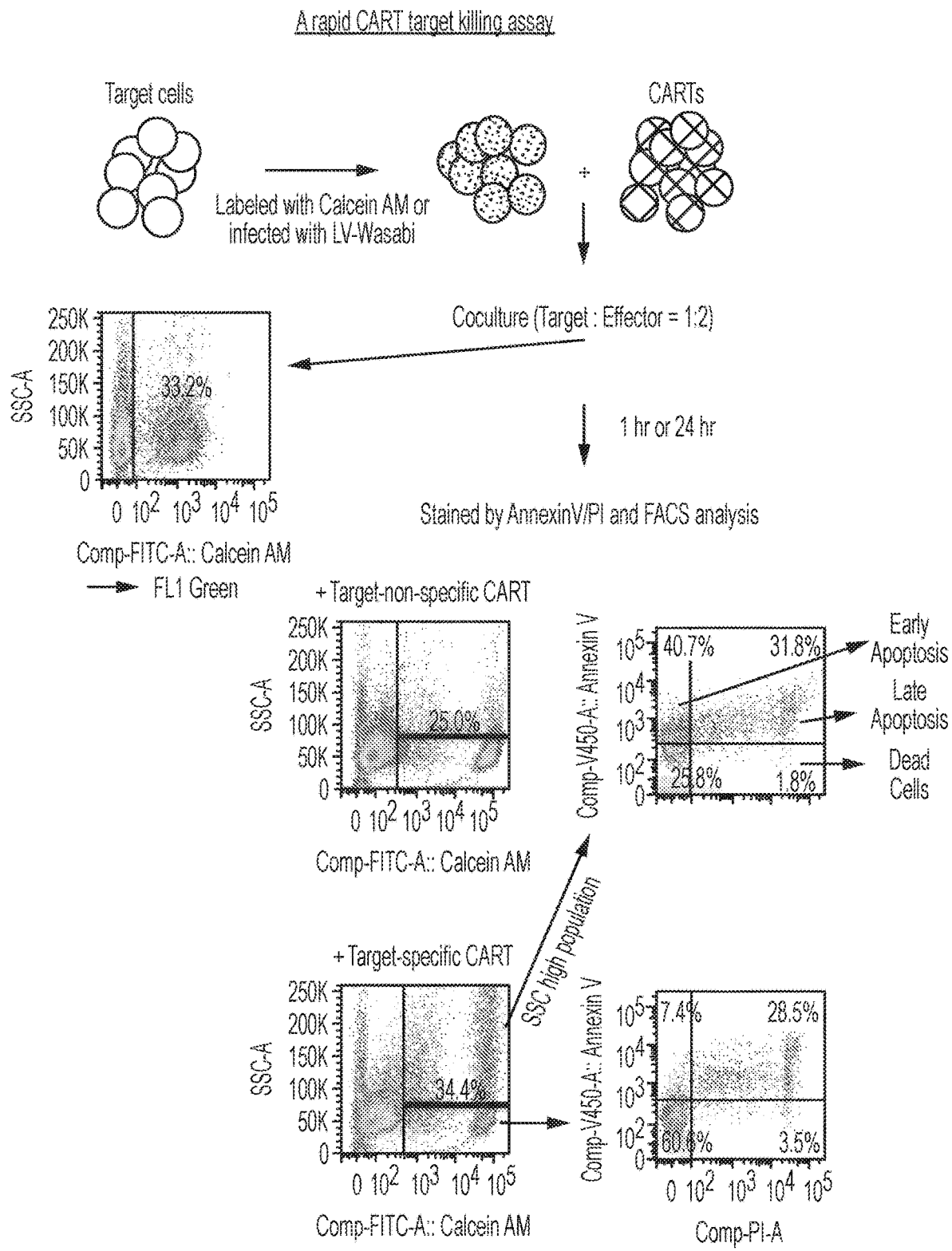
FIG. 2 is a diagram showing an exemplary simple killing assay—Co-culture of green fluorescent protein wasabi (GFP)-labeled target with the CART effector cells and flow cytometry after annexinV/PI staining.

To demonstrate CAR-mediated specific killing of target cells, a simplified killing assay was developed based on CAR-modified Jurkat T cells and target cells that were genetically engineered to express a green fluorescent protein (wasabi) or labeled with calcein AM. To illustrate CART-mediated target killing, the Jurkat-CARTs (effectors) were incubated with the GFP-labeled target at different effector: target ratios, and at various time points, the cultured cells were stained with annexin V and PI and analyzed by flow cytometry. The diagram in FIG. 2 illustrates the killing assay; representative flow cytometry graphs demonstrate the ratio change of the green target cells (%), the altered target cell morphology shown by increased side scatter (SSC) reflecting apoptosis, and the populations of early and late apoptotic cells (annexin V-stained) and dead cells (PI-stained). All CAR constructs were verified for specific target killing activities prior to the primary T cell gene transfer studies.

Evaluation of CART Killing Efficiency Using Primary T cells

Figure 3:
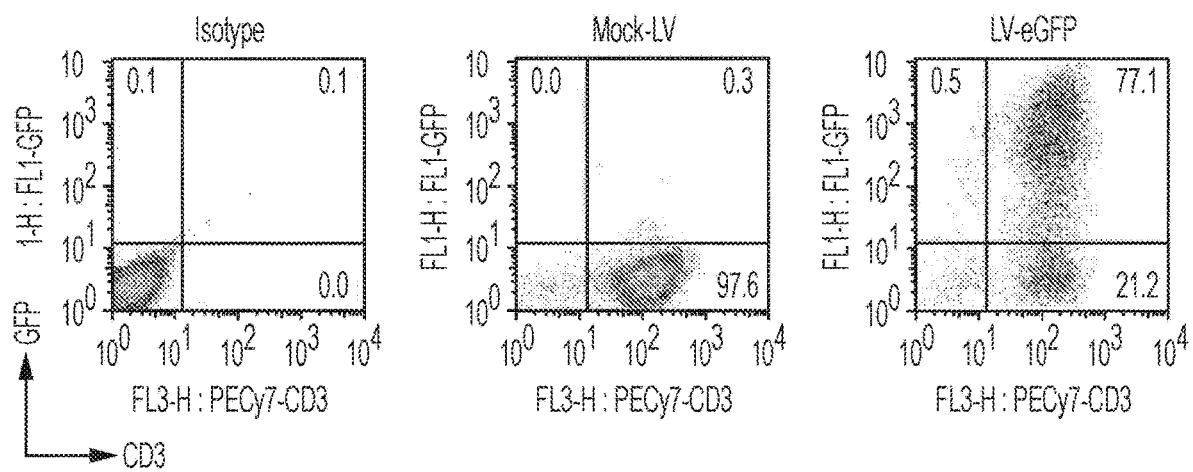
FIG. 3 is a series of plots and two photographs showing that exemplary lentiviral gene transfer into human T cells is very high. The X-axis in each plot shows CD3 staining and the Y-axis in each plot shows GFP staining.
Figure 3:
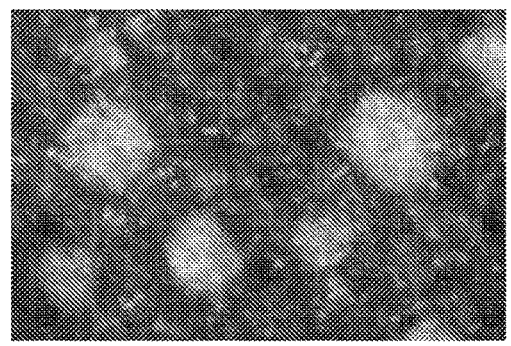
Figure 3:
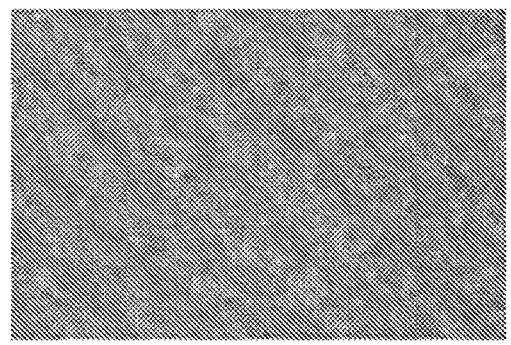
Figure 4:
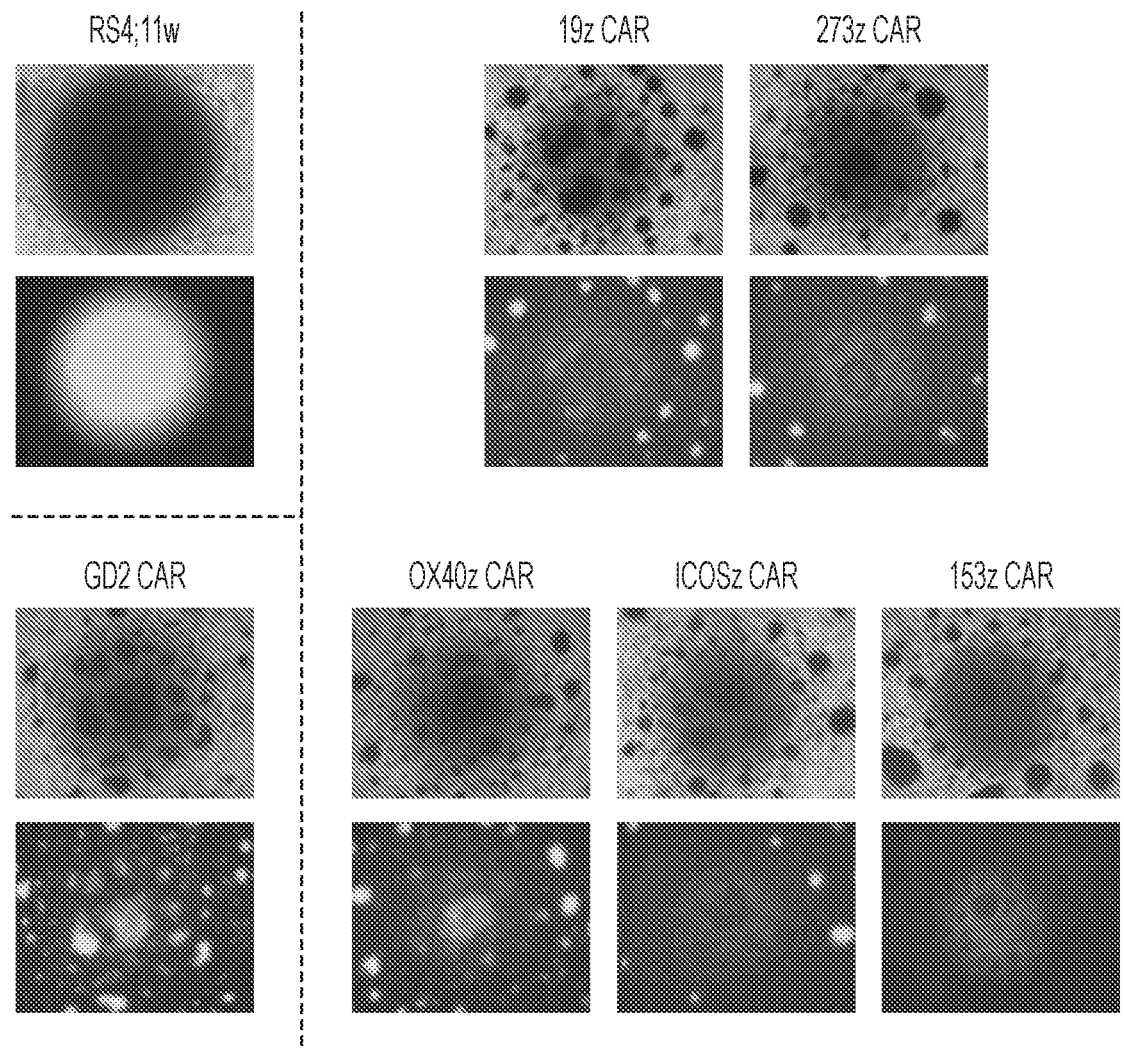
FIG. 4 is a series of photographs showing exemplary primary T cell killing efficiency demonstrated by disappearance of the green (fluorescent) target cells as seen under the fluorescent microscope. Both bright-field and fluorescent images are shown for each sample.

Jurkat CARTs are convenient for short term killing assessment. However, Jurkat CARTs lack long term killing function due to high PD-1 up-regulation after target engagement. Therefore, T cells from healthy donors were transduced with lenti-CAR vectors and tested for CART target killing activities. The efficiency of lentivector modification of primary T cells is very high (FIG. 3). Healthy donor T cells were transduced with 19z, 273z OX40z, ICOSz, and 153z lenti-CAR vectors. As control, GD2-CARTs expressing the ganglioside antigen GD2-specific CAR were included. RS4; 11w, a CD19+ve B-ALL cell line expressing wasabi GFP gene, was used as a specific target. Both target and effector cells were co-cultured in a ratio of 1:2 in a 96 U shaped well plate. Killing was assessed at 24-48 hr and pictures were obtained under fluorescent microscope. Representative results are illustrated in FIG. 4, which shows almost complete disappearance of the green target cells in the 153z coculture well, and decreased target in 19z, 273z, OX40z and ICOSz groups compared to target only and the non-specific GD2-CART groups. Repeated assays showed consistently that 153z had a rapid killing kinetics compared to the others.

Figure 5A:
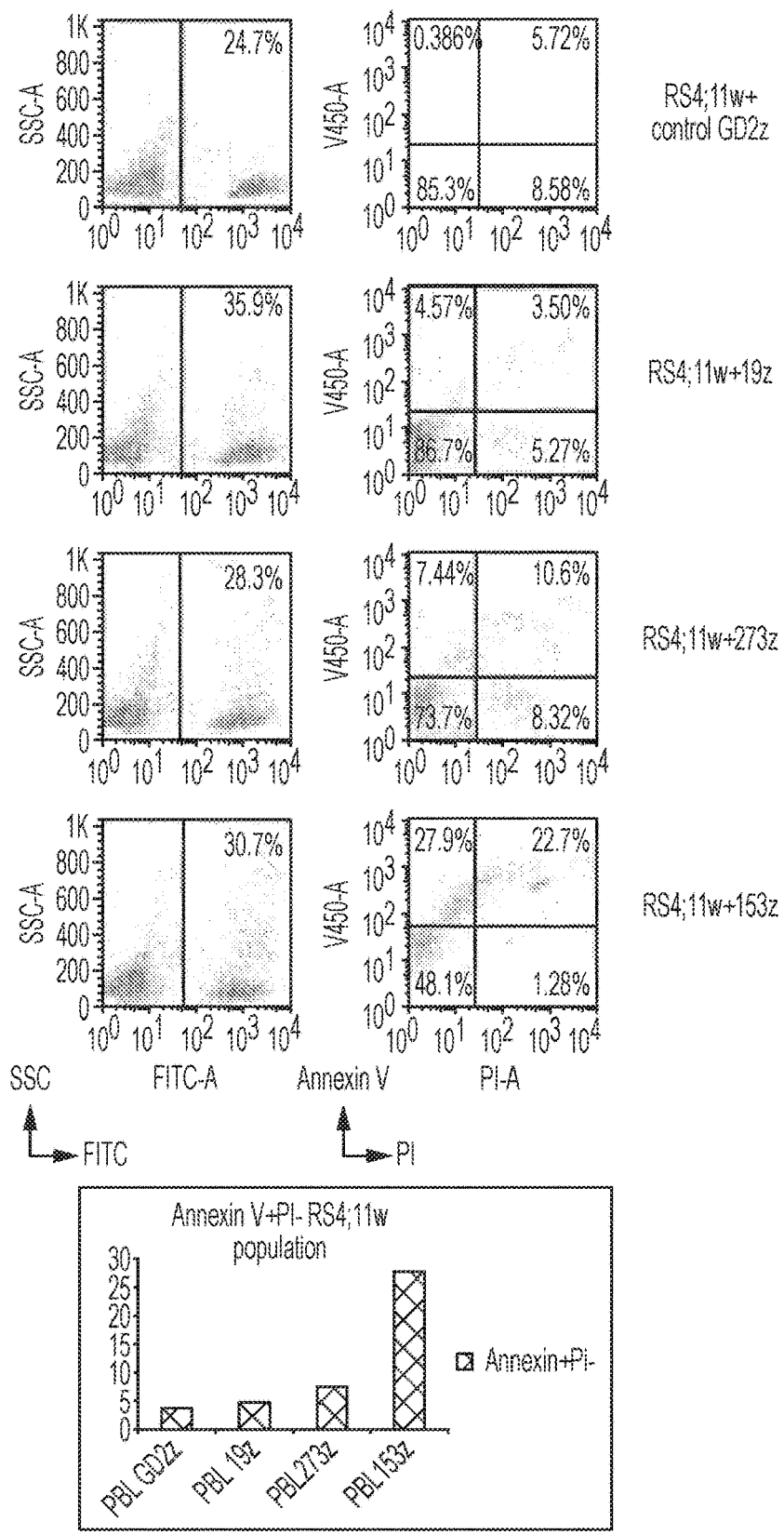
FIG. 5A is a series of plots and a graph showing exemplary healthy donor derived CART cells—Flow data of Killing in terms of % early apoptotic cells with annexinV positive and PI negative staining seen after 1-2 hours of co-culture.
Figure 5B:
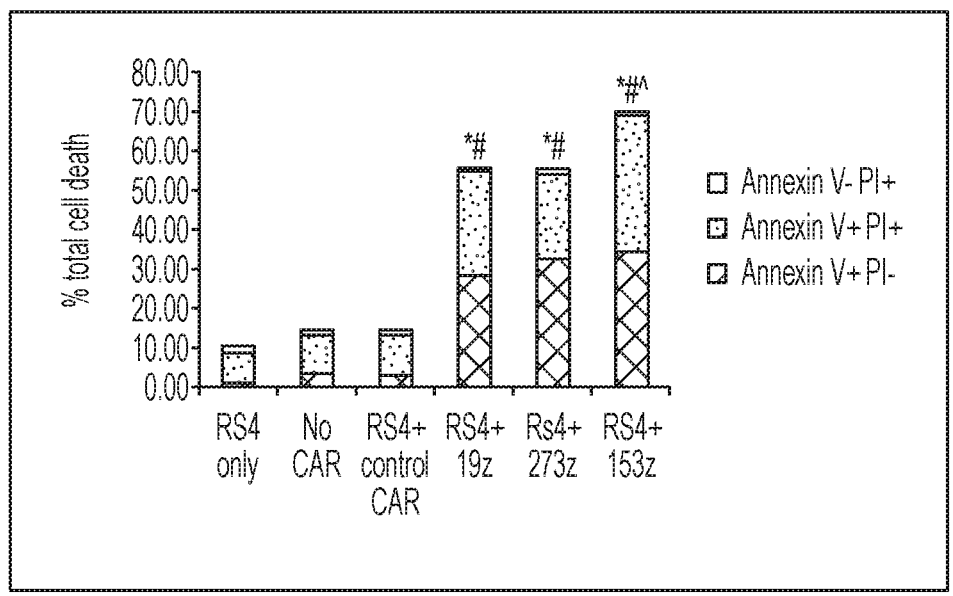
FIG. 5B is two graphs showing exemplary % total cell death (top graph) for each CAR and % specific lysis (bottom graph) for each CAR. This was done in triplicate wells to acquire mean values and statistical significance obtained using student t test ($p<0.05$ considered significant). *$P<0.01$ (comparing with No CAR), #$P<0.01$ (comparing with a control CART), ^$P<0.05$ (comparing 153z with 19z and 273z).
Figure 5B:
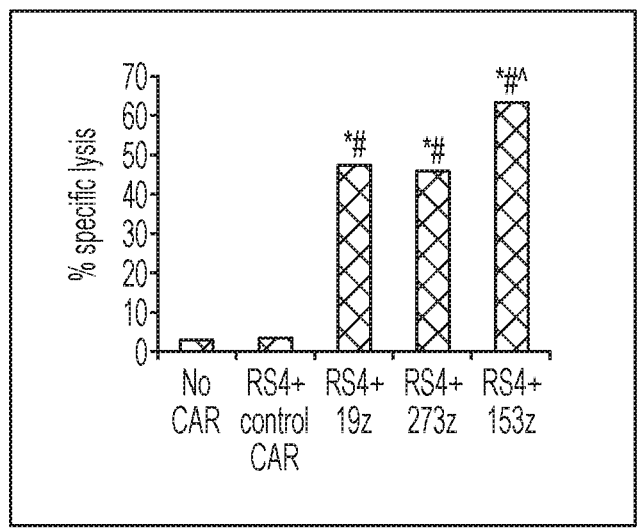

Highly Efficient and Rapid Target Killing Kinetics of 153z CAR in Both Healthy Donor and Leukemic Patient T Cells To further evaluate the rapid target killing activities of 153z CAR, the RS4;11w target was cocultured with healthy donor PBMC-derived 19z, 273z, 153z and control GD2z CARTs at 1:1 ratio for one hour, and cells were stained with annexin V and PI and analyzed by flow cytometry. The result confirmed that 153z CARTs killed the target at the highest efficiency quickly based on the analysis of early apoptotic cells by annexin V staining (annexin V positive and PI negative, FIG. 5A). This assay was repeated in triplicates and both percentages of total cell death and specific target lysis were analyzed, and statistical significance was obtained as shown in FIG. 5B.

Figure 6A:
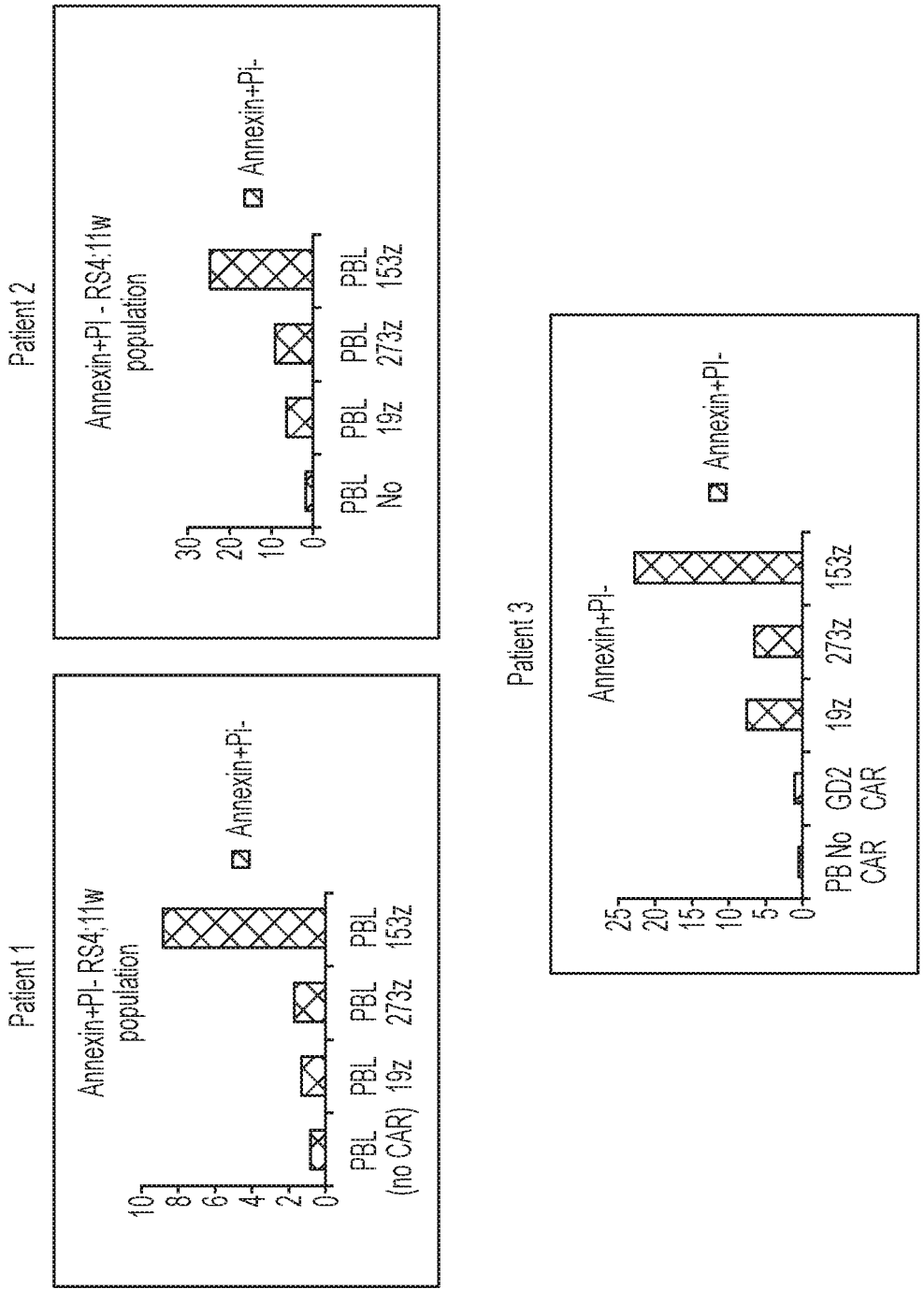
FIG. 6A is a series of graphs showing exemplary flow data of killing after overnight incubation in terms of % early and late apoptotic cells (both annexinV+PI− and double positive for AnnexinV and PI)
Figure 6B:
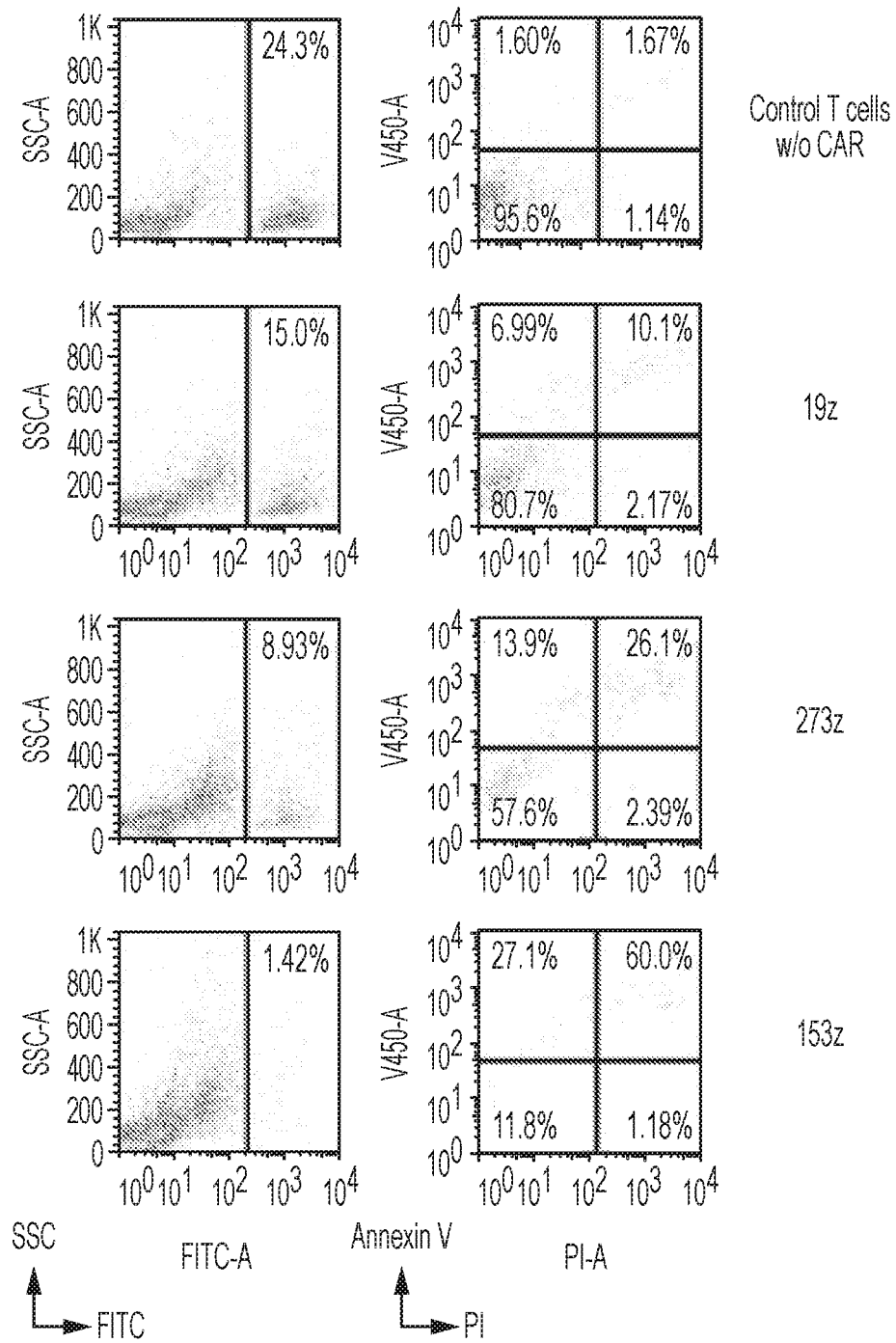
FIG. 6B is a series of plots and graphs showing exemplary long term killing after 3 days of co-coculture of patient derived CART cells with green (fluorescent) target cells. Killing was indicated by disappearance of the green target cells.
Figure 6B:
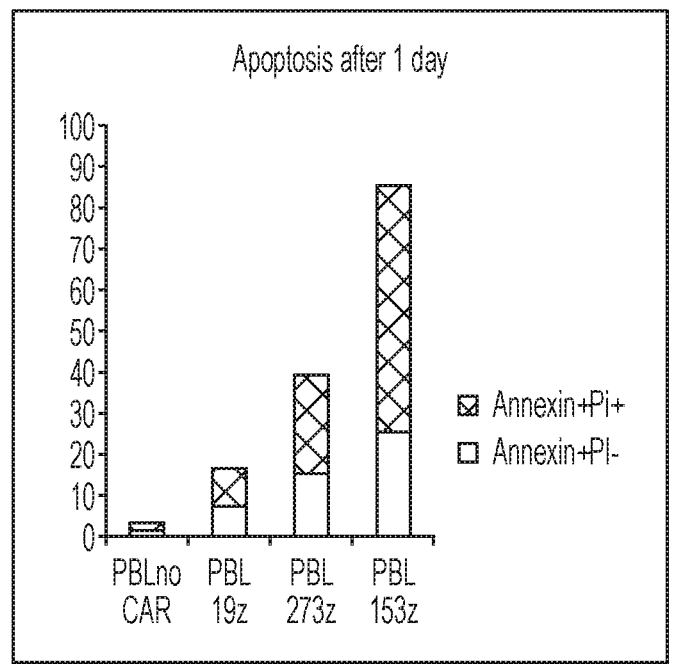
Figure 6B:
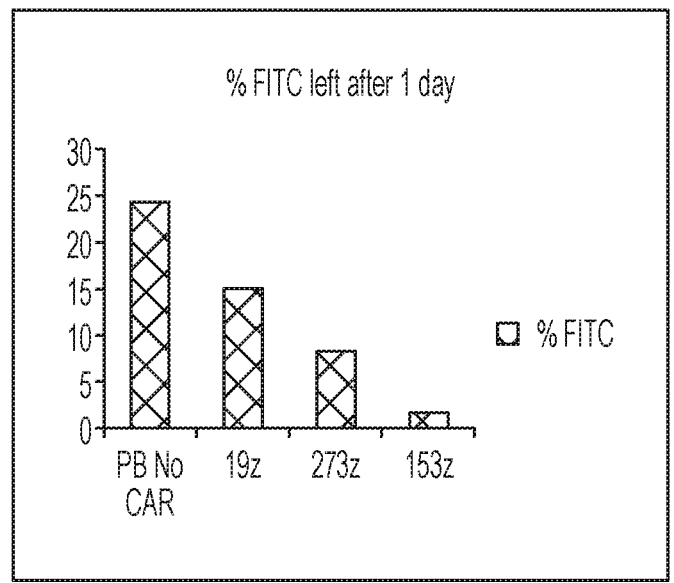
Figure 6C:
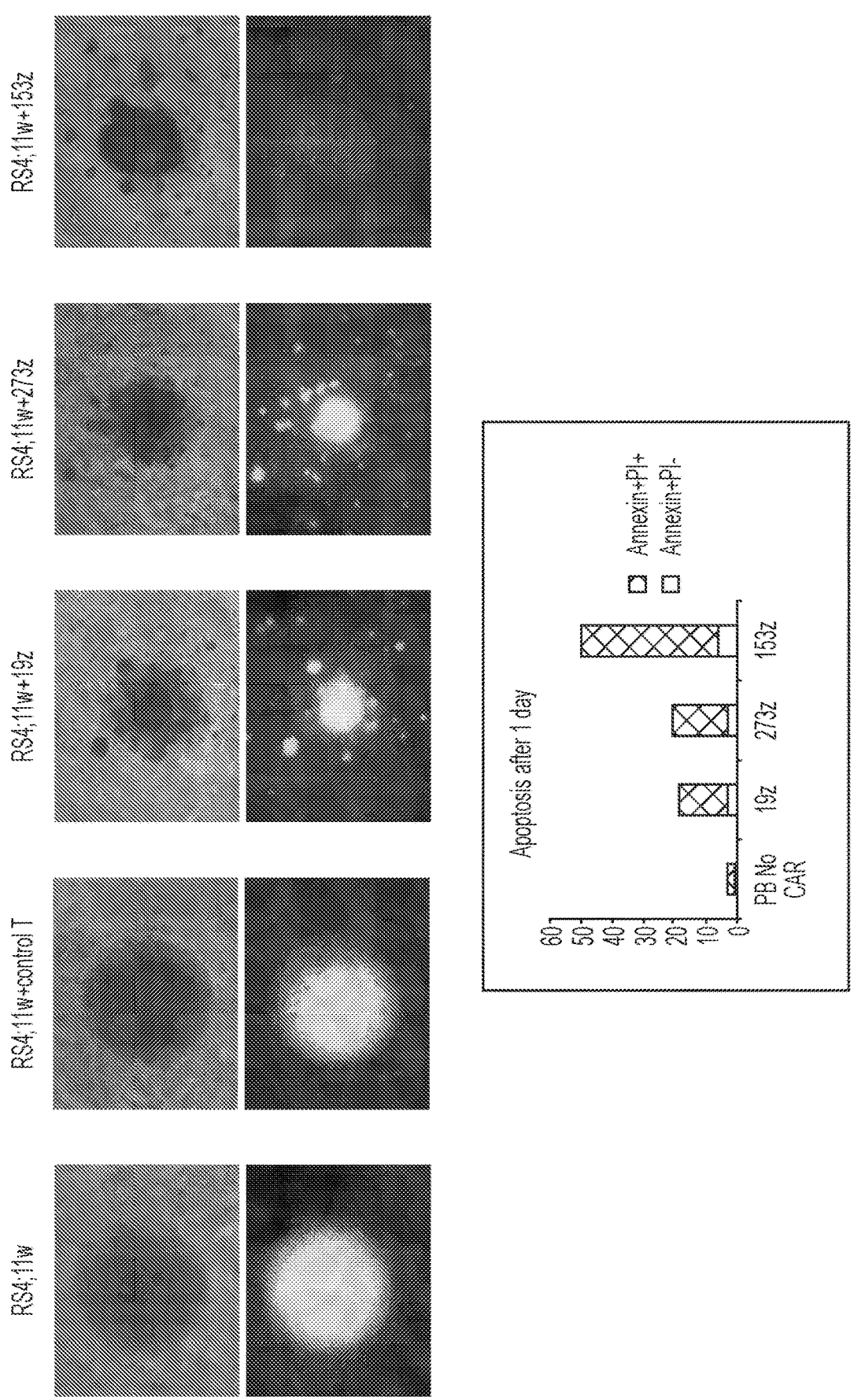
FIG. 6C is a series of photographs and a graph showing exemplary long term killing after 3 days of co-coculture of patient derived CART cells with green (fluorescent) target cells. Killing was indicated by disappearance of the green (fluorescent) target cells.

To examine the activities of 153z CAR in leukemic patients' T cells, RS4;11wasort target killing assay was performed using CARTs generated from B-ALL patients' T cells. 19z, 273z and 153z CARs were compared in three leukemia patients' T cells in a short term assay as described above. The results again confirmed that 153z displayed the fastest killing kinetics as illustrated by annexin V staining for early apoptotic cells in 1-2 hours (FIG. 6A). This was evident after 1-3 day coculture when cell death was analyzed by annexin V/PI staining and the disappearance of GFP+ target cells examined by flow cytometry and under fluorescent microscope (FIGS. 6B, 6C).

Effective Killing of Patient Leukemic Cells by Autologous 153z CARTs

Figure 7A:
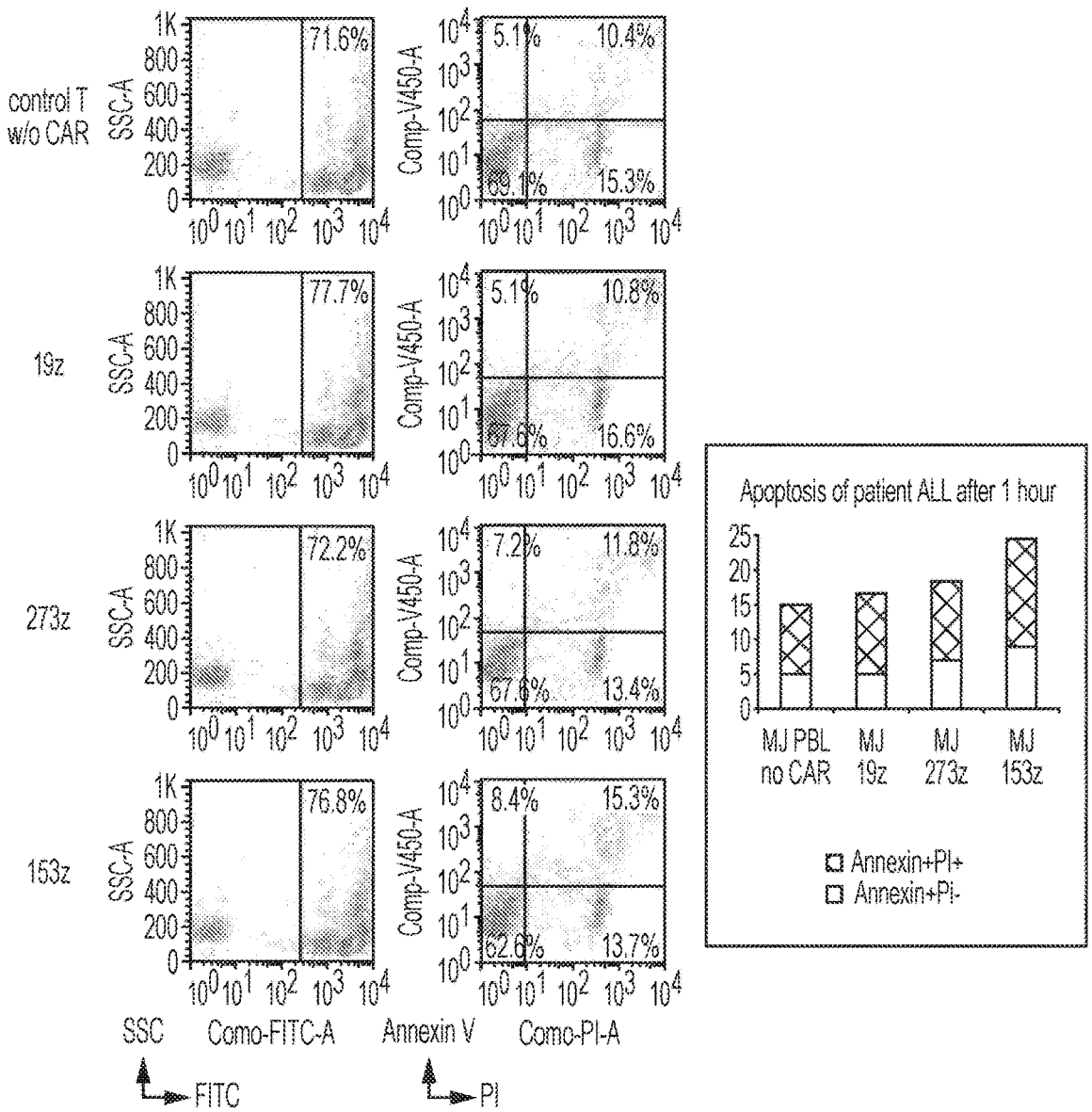
FIGS. 7A and 7B show a series of plots and graphs of exemplary patient ALL cells labeled with Calcein AM and patient derived CART cells incubated in 5:1 ratio. Flow data shows killing at 1 hour (FIG. 7A) and 1 day (FIG. 7B) in terms of early apoptosis with % annexinV positive and PI positive cells.
Figure 7B:
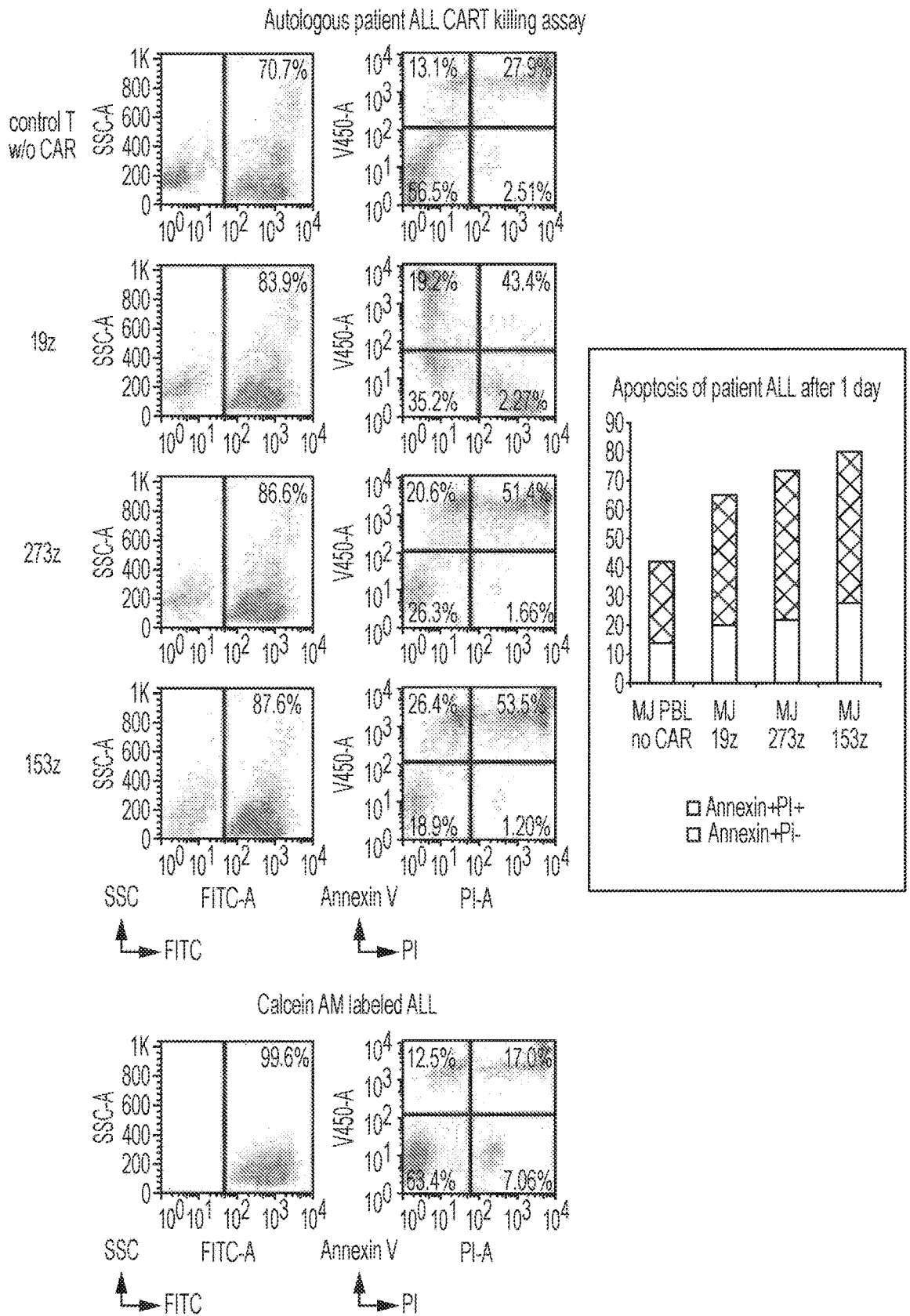

The above assays used B-ALL cell line RS4;11 as target cells. To illustrate killing of the patients' own leukemic cells, B-ALL patients' leukemic cells were obtained from bone marrow of two patients. These cells were labeled with green fluorescent dye calcein AM and co-cultured with autologous CARTs of 19z, 273z and 153z from the two B-ALL patients at effector:target ratio of 1:5. Target cell death was examined after 1 hour and 1 day. FIG. 7 demonstrates that 153z CARTs displayed the same trend of high target killing activities as compared with 19z and 273z in 1 hr (FIG. 7A) and 1 day (FIG. 7B) co-cultures of patients' own leukemic cells. Similar results were obtained for the second patient (not shown).

Prolonged Killing Function of 153z CARTs

Figure 8:
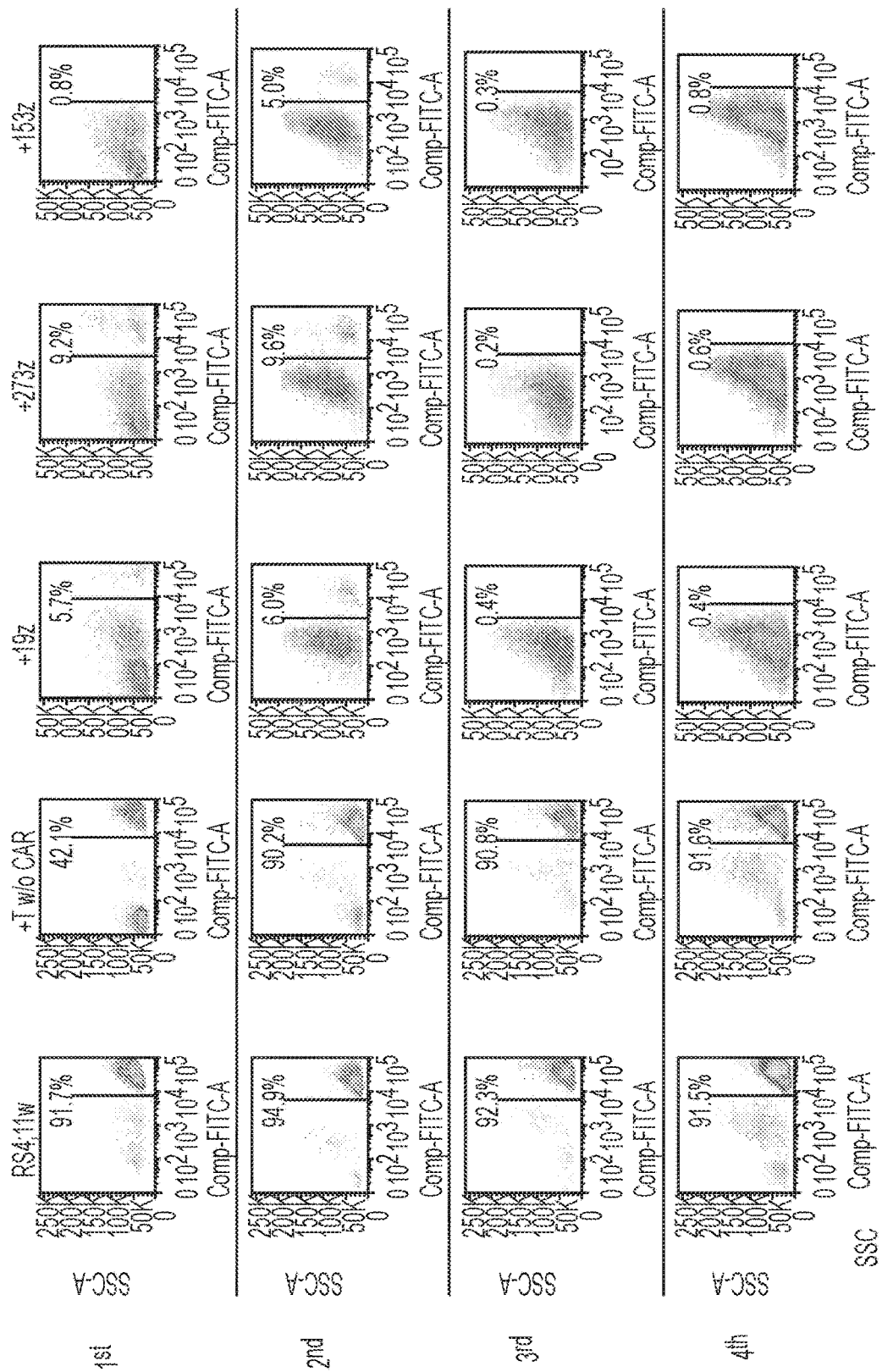
FIG. 8 is a series of plots showing exemplary retargeting of CART effector cells with green (fluorescent) target. Killing seen as indicated by disappearance of target in flow cytometry.

Next it was determined if these CD19 CARTs retained their ability to kill more target cells after they had already been exposed to target once. After the green target was completely gone, the remaining live cells were counted, which were mainly the CART effector cells. An equal number of the various CARTs was added to 10 times RS4;11w target in further rounds of killing, and flow cytometry was performed to determine the green target cells left at various time points. Both a healthy donor and a leukemic patient CARTs were tested. The results showed that target was eliminated efficiently after even fourth rounds of coculture, all within 1-2 days, as shown with the leukemia patient CARTs in FIG. 8. Importantly, 153z, although killed rapidly, retained capacity to further kill more target cells.

Increased T Cell Proliferation and Effector Functions of 153z CAR

Figure 9:
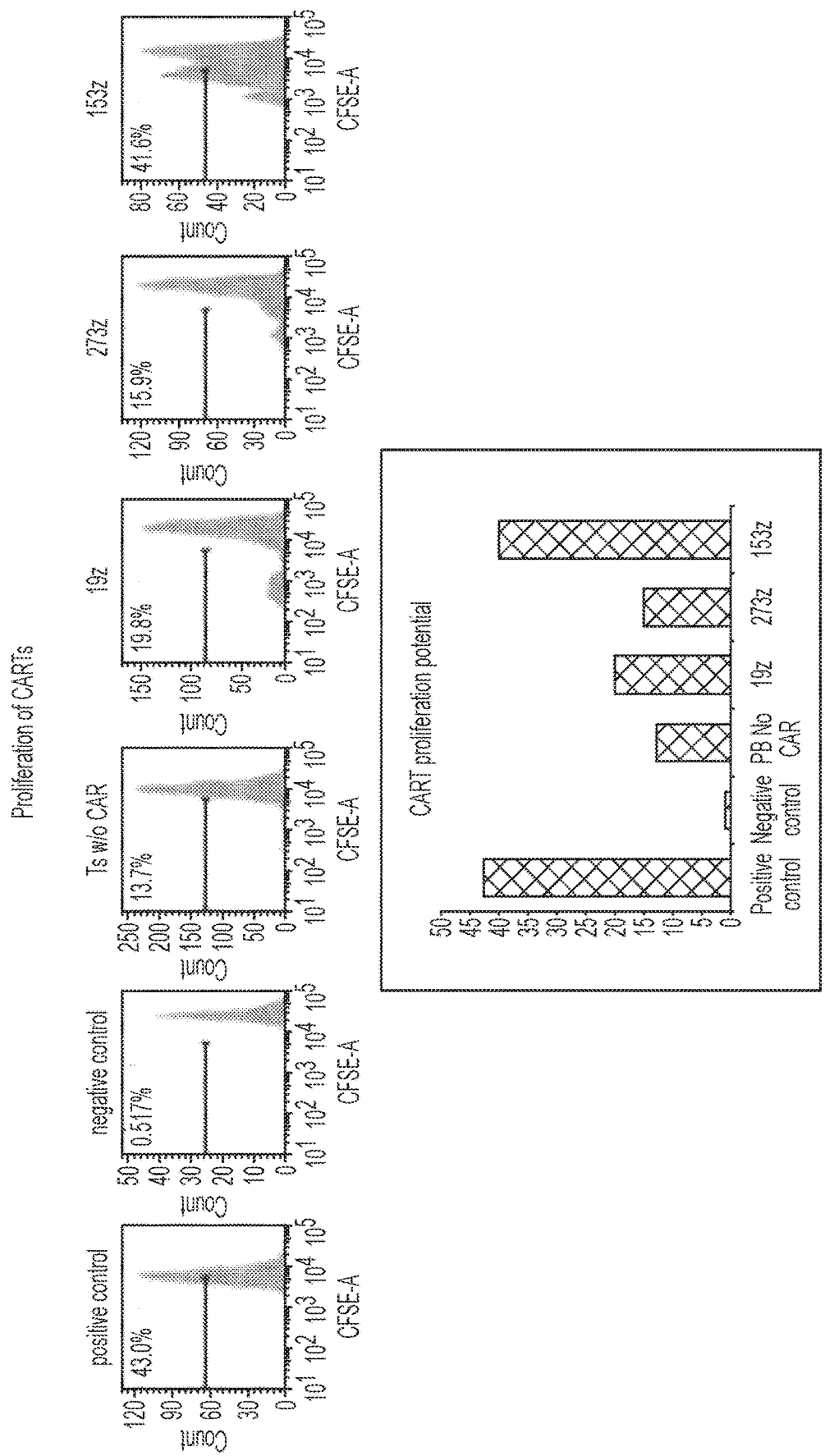
FIG. 9 is a series of plots and a graph showing exemplary CART cell proliferation by a CFSE method. Proliferation peak and % seen after CART cells stimulation with target cells.
Figure 10A:
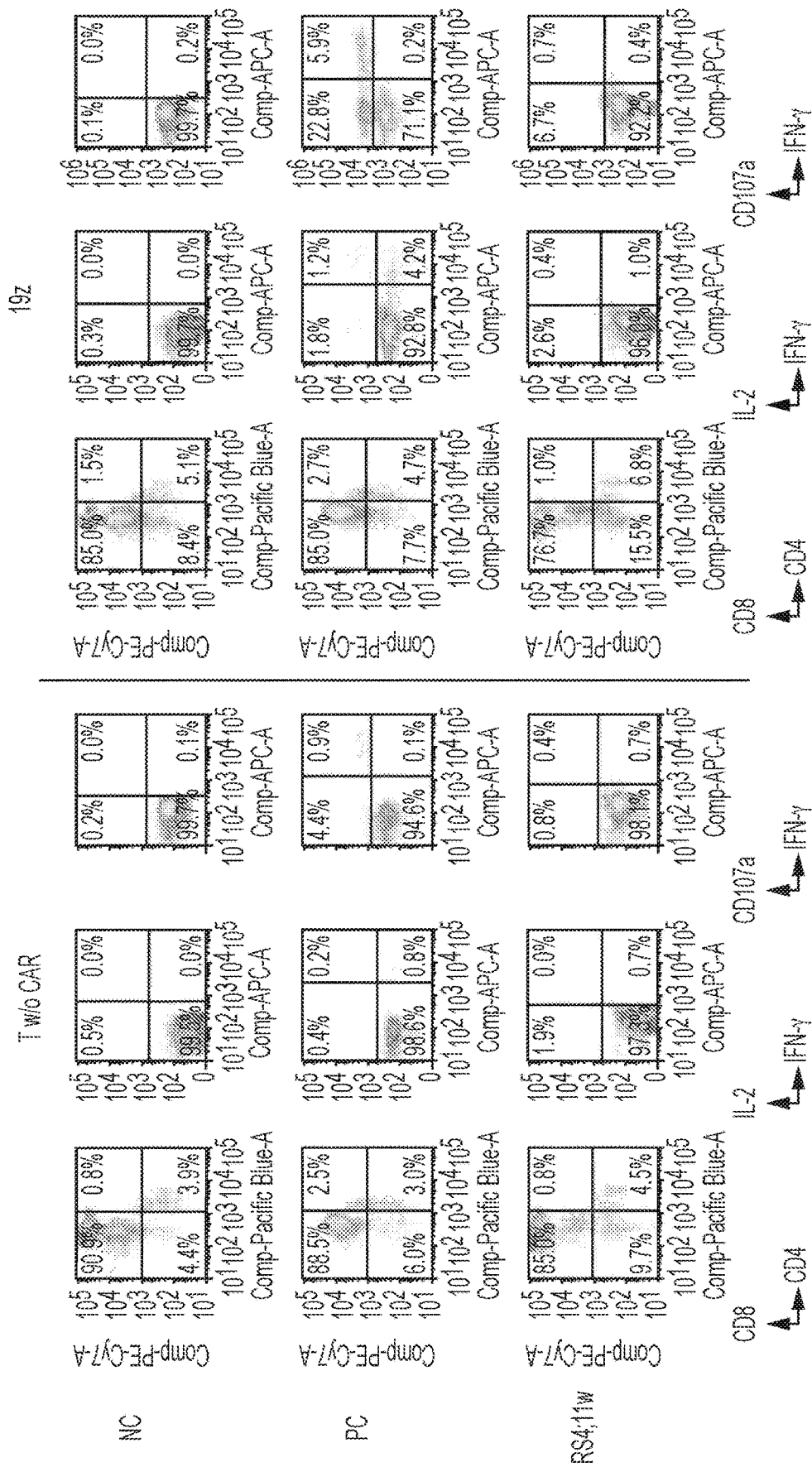
FIGS. 10A and 10B are a series of graphs showing exemplary intracellular effector function analysis flow data of IL-2, IFN-g and CD107a produced after the CART cells are co-cultured with the target cells—RS4-11. Positive control (PC) is PMA/ionomycin stimulation.
Figure 10B:
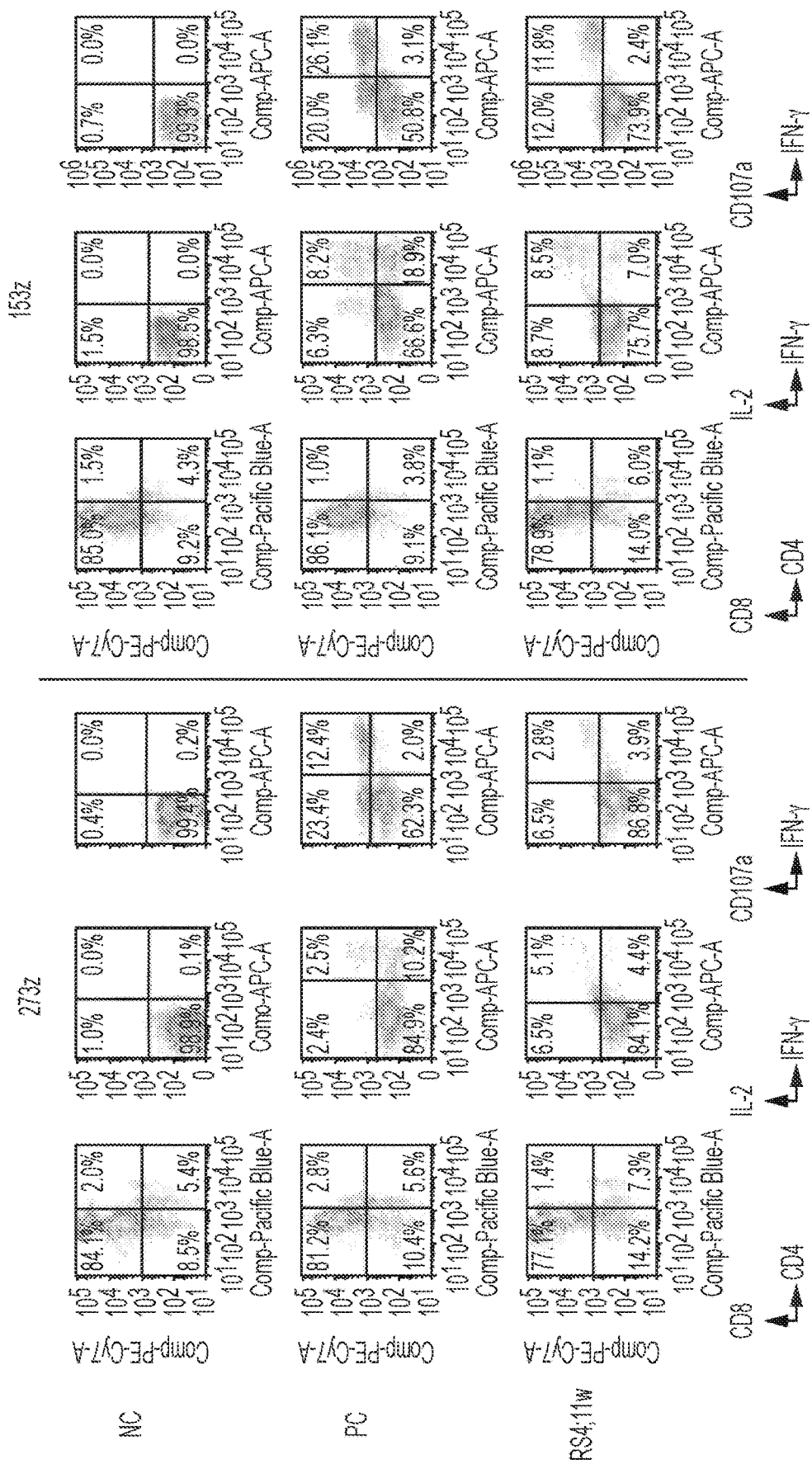
Figure 10C:
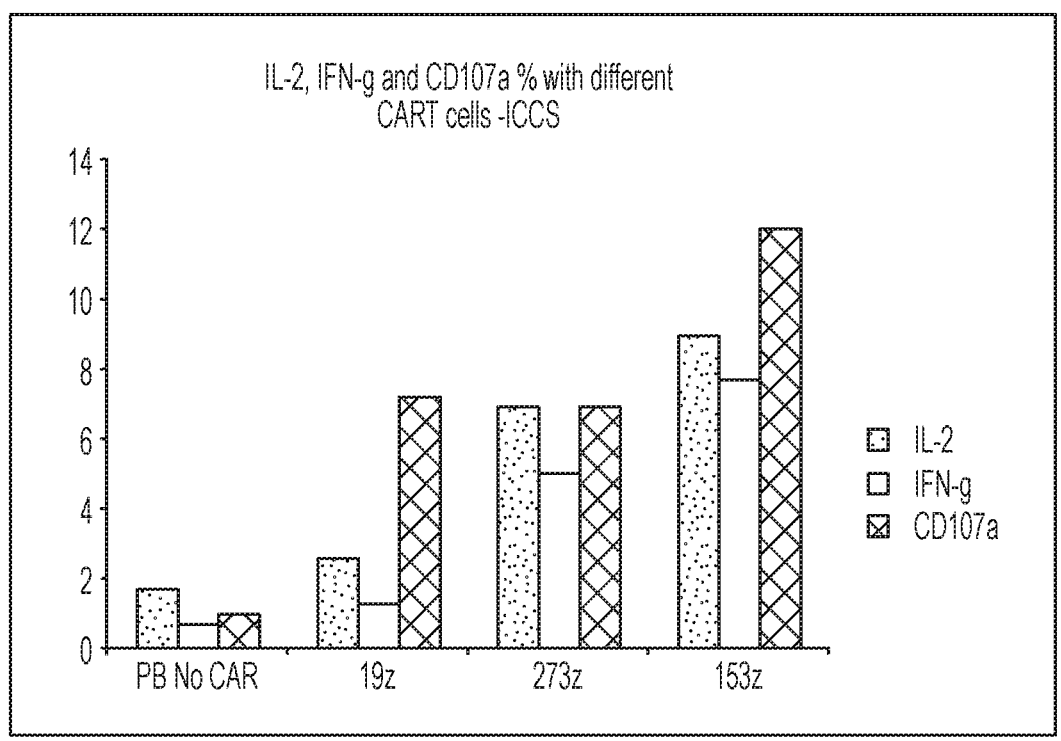
FIG. 10C is a graph showing the exemplary data summarized from FIGS. 10A and 10B in bar graph form. Maximum IL-2, IFN-g and CD107a release was seen with 153z CART cells.

The above results indicate that 153z had high target killing activities compared to 19z and 273z. Without wishing to be bound by theory, the target killing function of the CAR should be correlated with intracellular signaling for T cell proliferation and effector cytokine release. Next, T cell proliferation assays were performed based on CFSE labeling of T cells. Control T cells or CARTs were labeled with CFSE and cocultured with leukemic target cells for 3 days. Flow cytometry analysis revealed that 153z CARTs displayed the highest proliferation rate as compared with 19z and 273z CARTs (FIG. 9). For the effector function analysis, CARTs were stained for intracellular IL-2, IFNγ and degranulated CD107a after incubation with target cells. The results illustrated that 153z CARTs displayed the highest effector cytokine expression when co-cultured with target (FIGS. 10A-10C). To confirm the intracellular cytokine results, a flow cytometry-based cytokine bead assay (CBA) was used to determine the concentration of various cytokines secreted into the cocultures. In this assay, T cells without CAR and with no target added and T cells stimulated with PMA and ionomysin were included as negative and positive controls, respectively. Supernatants from 153z CART co-culture collected on 48 hr contained the highest amount of IFNγ and IL-2 compared to 19z and 273z CART co-cultures.

Genetically modified T cells have shown great promise in the treatment of B cell malignancies in the last five years. Among a number of published CART trials in hematological malignancies, CD19 or CD20 has been an effective target {Porter D L, 2011, Chimeric antigen receptor-modified T cells in chronic lymphoid leukemia; Brentjens R J, 2013, CD19-targeted T cells rapidly induce molecular remissions in adults with chemotherapy-refractory acute lymphoblastic leukemia; Kochenderfer J N, 2013, Donor-derived CD19-targeted T cells cause regression of malignancy persisting after allogeneic hematopoietic stem cell transplantation; Grupp S A, 2013, Chimeric Antigen Receptor-Modified T cells for Acute Lymphoid Leukemia.}. Several variables are still being investigated in determining the CART efficacy and persistence in vivo. One of the important determinants of CART efficacy is the choice of activation or co-stimulatory signals in the CAR structure. The study described herein made an attempt to further perfect the CAR design by exploring the potent activating signal of IL-15Rα (153z CAR) as a co-stimulatory domain and found that these CARTs have rapid reaction kinetics and high targeting efficacy. To assess CAR functions, an efficient lentiviral vector gene delivery system has been applied and a rapid cytotoxic assay without pre-selection of CAR transduced T cells has been developed. The different CARTs were transduced with lenti-CAR vectors at similar efficiencies based on quantitative PCR confirming the CAR transgene copy number in the cells. The 153z CARTs killed target CD19+ cells very rapidly as compared to 19z and 273z CARTs in short term assays from 30 min to two days. To assess long term killing effects, more than ten times of target cells were repetitively added to the CARTs, and interestingly, the CARTs became more effective after the first round of killing, likely due to selective expansion of functional CARTs. The latter is similar to the findings of Henderson et al. who has reported enhanced killing of CARTs on re-encountering the target {Henderson, 2013, Chimeric antigen receptor-redirected T cells display multifunctional capacity and enhanced tumor-specific cytokine secretion upon secondary ligation of chimeric receptor}. This is also consistent with in vivo observation that infused CARTs can expand more than 1,000 fold in leukemia patients {Porter D L, 2011, Chimeric antigen receptor-modified T cells in chronic lymphoid leukemia; Brentjens R J, 2013, CD19-targeted T cells rapidly induce molecular remissions in adults with chemotherapy-refractory acute lymphoblastic leukemia.}.

The assessment was further conducted using the primary patient T cells with CAR and patient ALL cancer cells. A much higher ratio of target:effector such as 10:1 was tested to closely parallel the in vivo situation where tumor burden may be much higher compared to the infused CART cells. Effective killing was observed even in this setting. These results indicate that the CD19-specific CART cells can efficiently target ALL coupled with high proliferation rate, activation of effector functions, resulting in complete eradication of cancer cells. The CFSE-based proliferation assay indicates that the 153z CARTs proliferated to the greatest extent compared to the 19z and 273z CARTs. One of the factors contributing to the enhanced killing seen with 153z CARTs might be the rapid expansion of these cells when they see target. In addition, 153z CARTs secreted increased amount of effector cytokines such as IFNγ, TNFα and IL-2 upon target engagement, as compared with 19z and 273z CARTs. Therefore, without wishing to be bound by theory, the enhanced target killing of 153z CARTs is conceivably a result of both rapid response kinetics and high effector activities.

As with T cell nature and biology, expansion and differentiation could result in exhaustion. 153z cells killed more rapidly and efficiently when they encountered target, so they could exhaust rapidly as well. Re-targeting experiments were performed by counting the cells from the co-culture after all the target was gone and adding more target in a ratio of 10:1 target to effector to a 48 well plate. This retargeting demonstrated that the target was killed more rapidly as the T cells were already in an activated, effector state. The 153z cells retained their capacity to kill as effectively as the 19z and 273z cells in the retargeting experiment. Interestingly, the increased activated state of 153z CART was associated with decreased PD-1 expression on these cells after the first round killing, suggesting that initial expansion of 153z CARTs is not very exhaustive.

Without wishing to be bound by theory, when CART binds the tumor antigen, this sends an activation signal and converts the memory T cells into effector T cells which mediates the killing by perforin-granzyme pathway, and the release of effector cytokines leading to sustained T cell activation {Trapani, 2002, Functional significance of the perforin/granzyme cell death pathway}. CD107a degranulation is another marker for T cell effector function associated with cytolytic activities {Betts, 2004, Detection of T-cell degranulation: CD107a and b. Methods in Molecular Medicine}. The study herein showed the differential production of these cytokines and up-regulation of CD107a expression when the different CART cells were encountering target by intracellular cytokine staining, and confirmed that these effector markers were in line with the strength of the T cell activation signal and target killing function. Again, the highest effector markers were observed with 153z CARTs.

In a similar study, Hoyos et al. have reported CARTs with CD28 co-stimulatory domain along with IL-15 gene and an inducible caspase gene, which ectopically over express IL-15 to enhance killing, which could potentially lead to excessive IL-15 production which is known to be a tumor growth cytokine {Hoyos, 2010, Engineering CD19-specific T lymphocytes with interleukin-15 and a suicide gene to enhance their anti-lymphoma/leukemia effects and safety}. In 153z CAR, the IL-15Rα cytoplasmic domain is engineered in tandem with CD28 and CD3ζ, which confers a stimulating effect only when the CARTs encounter target. Thus, this design endows IL-15 signaling in the CARTs only independent of extracellular IL-15 expression.

In summary, the IL-15Rα endodomain confers a potent stimulus to the CART when it encounters target, leading to enhanced proliferation, effector activities and target killing. In clinical settings, during the initial treatment when disease burden is high, CARTs with rapid killing efficacy could be advantageous and once this effect is seen, maintenance CARTs may be applied for persistence. Besides leukemia, it is also anticipated that the rapid 153z CAR effector kinetics may achieve better therapeutic outcomes in the more difficult to target tumors such as solid tumors.

Example 2

Demonstration of Safety and Efficacy of Chimeric Antigen Receptor (CAR)-Modified T Cells for the Treatment of Relapsed or Refractory CD30 Positive Lymphomas The leukocyte activation marker CD30 (TNFRSF8) is a 120 kDa type I transmembrane cytokine receptor from the tumor necrosis factor receptor (TNFR) superfamily. CD30 is consistently expressed in Hodgkin lymphoma (HL), anaplastic large cell lymphoma (ALCL), and variably expressed in other B and T cell lymphomas, including diffuse large B-cell lymphoma (DLBCL), primary effusion lymphoma, adult T-cell leukemia/lymphoma, mycosis fungoides, and extranodal natural killer/T-cell lymphoma. A large number of CD30 positive lymphoma patients cannot be cured by standard chemo-radiotherapy. Brentuximab Vedotin (SGN-35) is an antibody-drug conjugate directed against the CD30 antigen expressed on lymphoma cells, which has been approved by U.S. Food and Drug Administration (FDA) for the treatment of relapsed or refractory classical HL and systemic ALCL. However, SGN-35 is not available or approved in many countries. Therefore, although CD30 represents an attractive target for immunotherapy, there remains a need to develop alternative CD30-targeting therapeutics.

Described in this example are a experiments related to a chimeric antigen receptor (CAR) that targets CD30 and a clinical trial of autologous T cells expressing this CAR. Pre-clinical study results and the preliminary outcome of one patient enrolled in a clinical trial of anti-CD30 CAR T cells for the management of relapsed and refractory CD30 positive lymphomas (www.clinicaltrials.gov; #NCT02274584) are reported.

Materials and Methods

Cell Lines and Media

Figure 11:
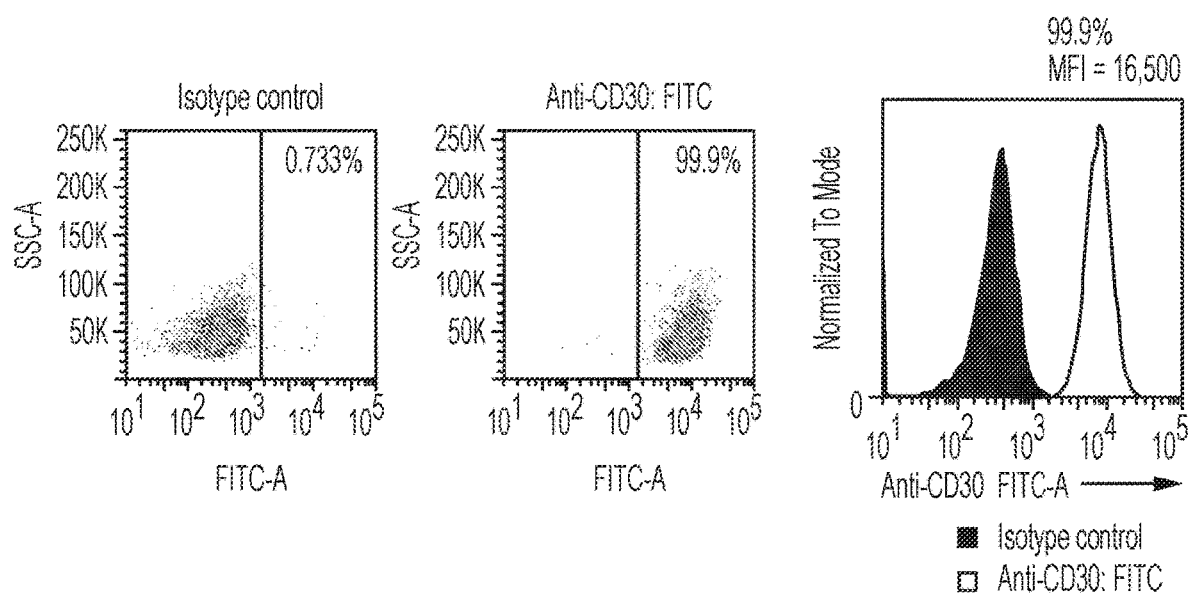
FIG. 11 shows flow cytometry analysis of CD30 surface expression of a primary B cell tumor line.

CD30-positive target cells were used for the CAR T cell target killing assays. Primary CD30+ ALCL cells and B lymphoma cells were established in the laboratory. These cells were maintained in RPMI1640 medium (Life Technologies, Inc. Grand Island, N.Y.) supplemented with 10% fetal bovine serum (Atlanta Biologicals, Inc. Norcross, Ga.), penicillin (100 units/ml) and streptomycin (100 ug/ml). Target cell lines were transduced with lentiviral vectors expressing a green fluorescent protein (wasabi GFP) and the reporter gene positive cells were sorted by flow cytometry (see FIG. 11). T cells were transduced with lentiviral CD30 CAR or control CAR vectors and the copy number of CAR per cell was determined by quantitative PCR using genomic DNA.

Blood Donors and Primary T Cell Culture

Buffy coats from healthy donors (HDs) were purchased from LifeSouth Civitan Blood Center (Gainesville, Fla., USA) with approval of Institutional Review Board (IRB-01) of University of Florida. PBMCs were isolated from buffy coats by gradient density centrifugation in Ficoll-Hypaque (GE Healthcare Bio-Sciences AB, Piscataway, N.J., USA). Blood and bone marrow samples of Hodgkin's lymphoma patients were obtained from Peking University Cancer Hospital with IRB approved protocol. T cells were activated using anti-CD3 and anti-CD28 antibodies or phytohemagglutinin (PHA). The T cells were maintained in TexMACS medium (Miltenyi Biotec Inc, San Diego, Calif.) supplemented with interleukin-2, -7 and -15. Phenotype analysis of the activated cells by flow cytometry was performed to confirm T cell purity. After expansion for two to six days, the T cells were transduced with lentiviral CAR vectors.

CD30 CAR Synthesis, Lentiviral Vector Construction and CAR Gene Transduction

The CD30 CAR sequence was codon optimized and chemically synthesized based on two published mAb clones, AC10 (a murine hybridoma IgG2b clone, J. Immunol. 1993, Dec. 1; 151(11): 5896-5906), and a humanized mAb clone 5F11. The amino acid sequences of the two scFv clones used for CD30 CAR engineering are listed below.

```
AC10 scFv:
VH
QIQLVQSGAEVKKPGASVKVSCKAS

GYTFTDYYIT (CDR1)

WVRQAPGQGLEWMG

WIYPGSGNTKYNEKFKG (CDR2)

RVTMTRDTSISTAYMELSRLRSDDTAVYYCAN

YGNYWFAY (CDR3)

WGQGTLVTVSS (SEQ ID NO: 14)

VL:
DIVMTQSPDSLAVSLGERATINC

KASQSVDFDGDSYMN (CDR1)

WYQQKPGQPPKLLIY

AASNLES (CDR2)

GVPDRFSGSGSGTDFTLTISSLQAEDVAVYYC

QQSNEDPWT (CDR3)

FGQGTKVEIK (SEQ ID NO: 13)

5F11 CD30 scFv:
VH
QVQLQQWGAGLLKPSETLSLTCAVYGGSFS

AYYWS (CDR1)

WIRQPPGKGLEWIG

DINHGGGTNYNPSLKS (CDR2)

RVTISVDTSKNQFSLKLNSVTAADTAVYYCAS

LTAY (CDR3)

WGQGSLVTVSS (SEQ ID NO: 16)

VL
DIQMTQSPTSLSASVGDRVTITC

RASQGISSWLT (CDR1)

WYQQKPEKAPKSLIY

AASSLQS (CDR2)

GVPSRFSGSGSGTDFTLTISSLQPEDFATYYC

QQYDSYPIT (CDR3)

FGQGTRLEIK (SEQ ID NO: 15)
```

Figure 12:
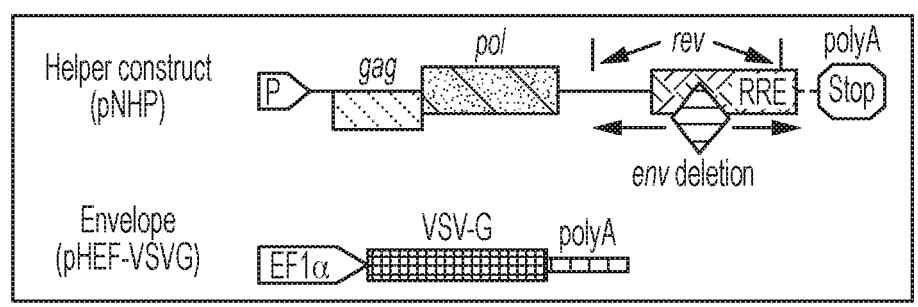
FIG. 12 shows an illustration of the lentiviral vector system.

The CAR contains a chimeric intracellular signaling element derived from CD28 trans-membrane and cytoplasmic domain, the co-stimulatory 4-1BB intracellular TRAF binding domain, a CD27 cytoplasmic domain, and the CD3ζ chain intracellular domain. The CAR gene was cloned into the lentiviral vector pTYF and packaged with NHP/VSVG lentivector system, as shown in FIG. 12.

Lentiviral vectors were generated based on the NHP/TYF lentiviral vector system. CAR DNA was chemically synthesized and cloned into pTYF transducing vector behind human EF1α promoter. The final lentiviral-CAR constructs were verified by restriction enzyme mapping and DNA sequencing.

CAR Gene Sequence

Figure 13:
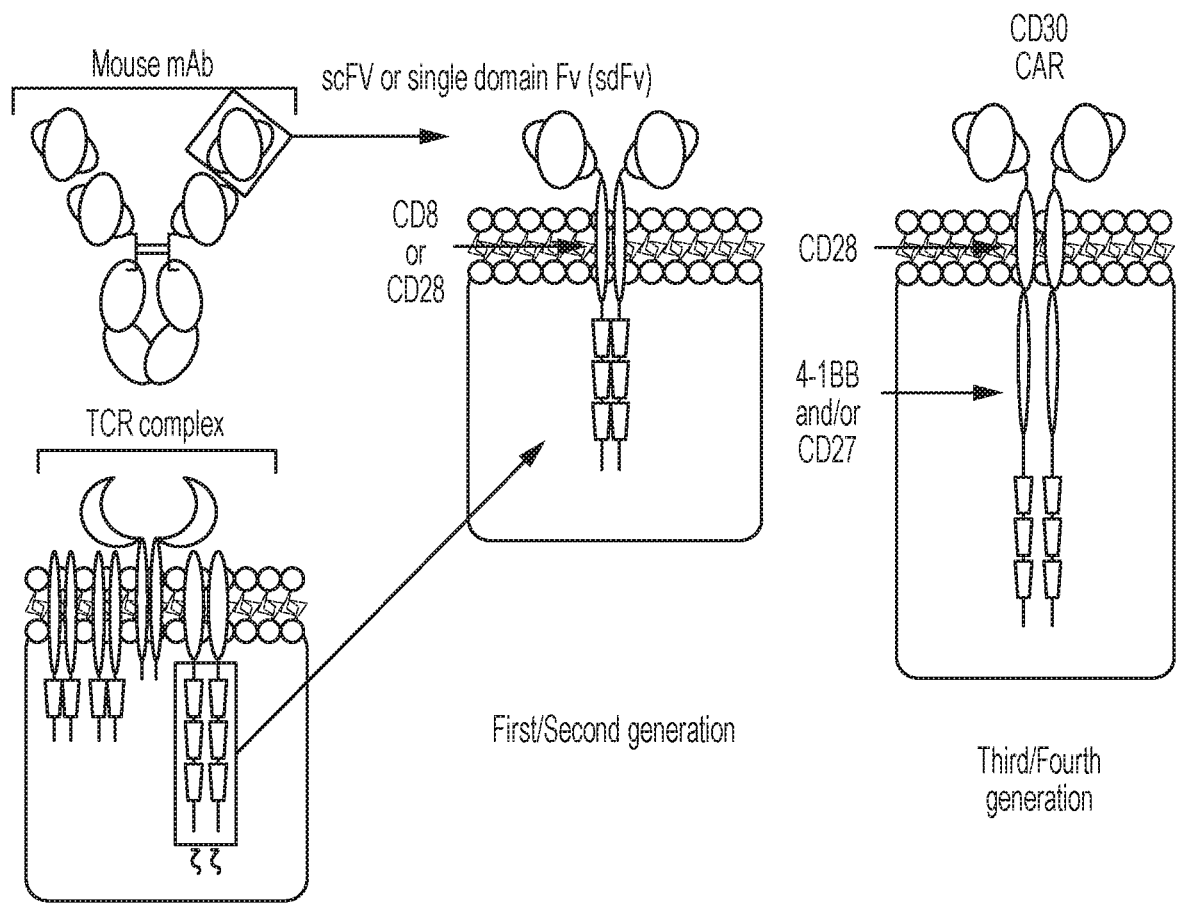
FIG. 13 shows diagrams illustrating embodiments of CAR molecules, including one embodiment of a 4th generation CD30-CAR structure and components.

The amino acid sequence of the CD30 CAR tested in this study is shown as follows, broken down by the domains included in the CAR. A schematic of a CD30 CAR is shown in FIG. 13:

```
QVQLQQWGAGLLKPSETLSLTCAVYGGSFSAYYWSWIRQPPGKGLEWIGDIN

HGGGTNYNPSLKSRVTISVDTSKNQFSLKLNSVTAADTAVYYCASLTAYWGQ

GSLVTVSS (CD30 scFv domain)

GSTSGSGKPGSSEGSTKG (Linker)

DIQMTQSPTSLSASVGDRVTITCRASQGISSWLTWYQQKPEKAPKSLIYAAS

SLQSGVPSRFSGSGSGTDFTLTISSLQPEDFATYYCQQYDSYPITFGQGTRL

EIK (CD30 scFv domain)

GSTSGSGKPGSSEGSTKG (Linker)

FWVLVVVGGVLACYSLLVTVAFIIFWV (CD28 transmembrane domain)
```

-continued

```
KRGRKKLLYIFKQPFMRPVQTTQEEDGCSCRFPEEEEGGCEL (4-1BB intracellu-
lar
domain)

QRRKYRSNKGESPVEPAEPCHYSCPREEEGST1PIQEDYRKPEPACSP
(CD27 intracellular domain)

GSTSGSGKPGSSEGSTKG (Linker)

RVKFSRSADAPAYKQGQNQLYNELNLGRREEYDVLDKRRGRDPEMGGKPRRK

NPQEGLYNELQKDKMAEAYSEIGMKGERRRGKGHDGLYQGLSTATKDTYDAL

HMQALPPR (CD3 zeta domain)

GSTSGSGKPGSSEGSTKG (Linker)

VGALESLRGNADLAYILSMEPCGHCLIINNVNFCRESGLRTRTGSNIDCEKL

RRRFSSLHFMVEVKGDLTAKKMVLALLELAQQDHGALDCCVVVILSHGCQAS

HLQFPGAVYGTDGCPVSVEKIVNIFNGTSCPSLGGKPKLFFIQACGGEQKDH

GFEVASTSPEDESPGSNPEPDATPFQEGLRTFDQLDAISSLPTPSDIFVSYS

TFPGFVSWRDPKSGSWYVETLDDIFEQWAHSEDLQSLLLRVANAVSVKGIYK

QMPGCFNFLRKKLFFKTS (truncated iCasp9 domain)

(SEQ ID NO: 32)
MGVQVETISPGDGRTFPKRGQTCVVHYTGMLEDGKKVDSSRDRNKPFKFMLG

KQEVIRGWEEGVAQMSVGQRAKLTISPDYAYGATGHPGIIPPHATLVFDVEL

LKLE (FKBP domain)
```

In some embodiments, the above exemplary, non-limiting arrangements are from left to right, N-terminus to C-terminus of the CAR. The CAR may comprise or further comprise any other combination of elements as described herein.

CAR Detection by PCR

The CAR transgene copy numbers in CART cells were determined by quantitative SYBR green real time PCR (qRT-PCR). Genomic DNA was harvested from CART cells using Promega Wizard genomic DNA purification kit (Promega Corp. Madison, Wis.). The qRT-PCR reaction condition was as suggested by SABioscience and data collected using MX3000P (Stratagene, Agilent Technologies, Santa Clara, Calif.).

Calcein AM Labeling of Primary Tumor Cells

Fresh or thawed tumor cells were first washed with RPMI1640 medium. Then $1\times10^6$ cells were suspended in 1960 of RPMI1640 in a tube, and 40 of Calcein AM (Life Technologies Corp., 20 μM) was added to get a final concentration of 0.4 μM. The cells were incubated at 37° C. for 1 hour and washed twice with RPMI containing fetal bovine serum before used in co-culture experiments.

CAR T Cell Killing Assay

Figure 14:
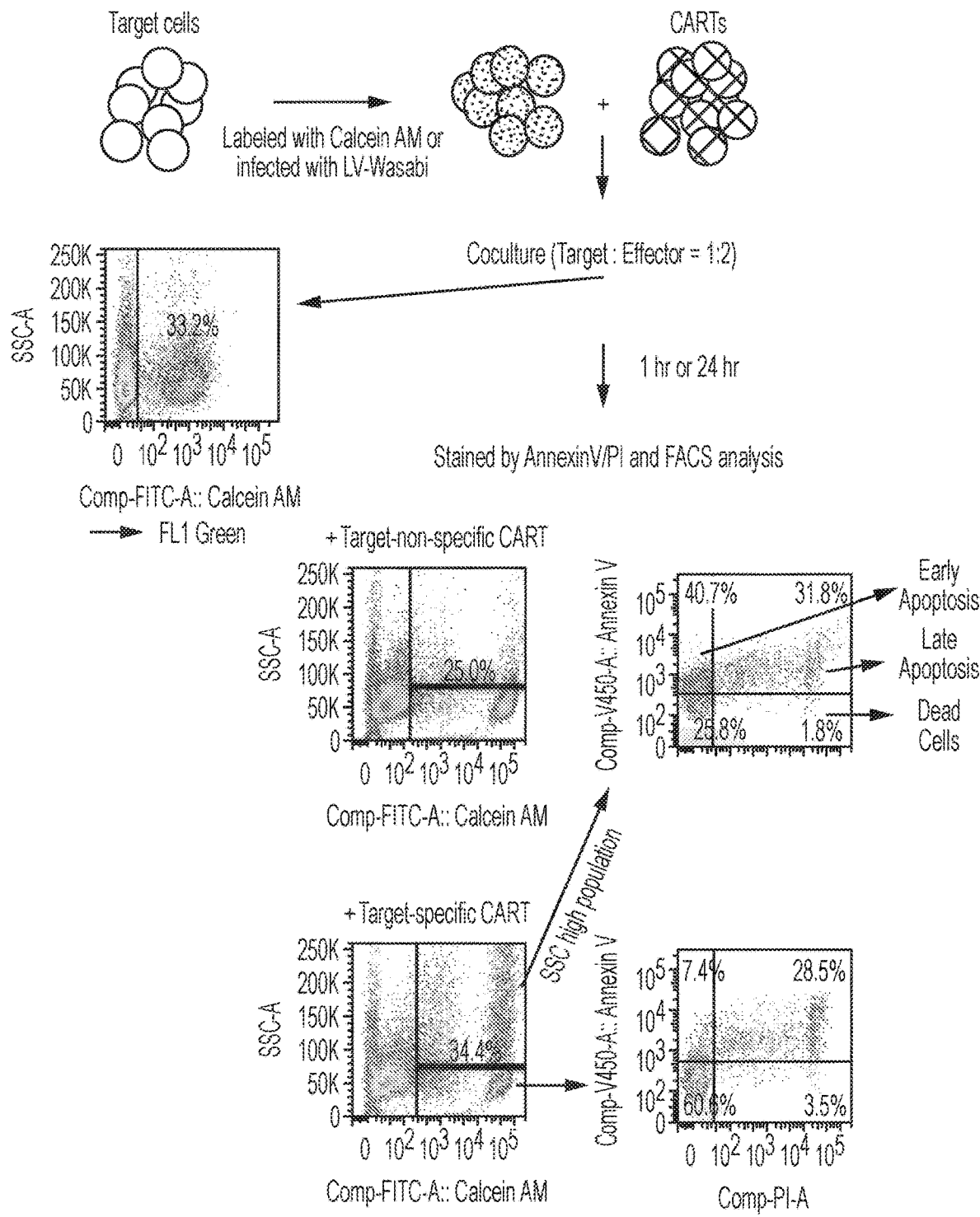
FIG. 14 shows an illustration of a rapid CAR T target killing assay used for the evaluation of CAR functions.

Target cells and CAR T cells were counted using trypan blue staining and a hemocytometer. The cells were co-cultured in 96U plate in effector:target ratios of 1-2:1, or as indicated in each experiment. CAR T cell numbers ranged from $5\times10^4$ to $2\times10^5$. The coculture was incubated in Tex-MACS medium without cytokines. Cells were incubated for 1-2 hours or overnight for short term assays. CAR T-targeted killing was recorded by quantitative analysis of the shifted side scattered (SSC) population, and early and late apoptotic (annexin V-stained) and Propidium Iodide (PI)-stained (dead) cells. Samples were run in the LSRII flow cytometer using the DiVa software (BD Biosciences) and results were analyzed using the FlowJo software. An example of results obtained using this assay is shown in FIG. 14.

Annexin V and PI Staining for Apoptosis

At different time points after incubation, cells were transferred to 96-V plate and centrifuged at 400 g for 5 minutes to remove the media. Then the cell pellet was washed with PBS once. Cells were re-suspended in 30 μl of staining mix consisting of 0.25 μl PI (Sigma), annexin V (BD Bioscience) and 29.25 μl of binding buffer (BD Bioscience), and then incubated in the dark for 15 minutes at room temperature. Subsequently, cells were suspended in 200 μl FACS buffer and analyzed in the LSRII flow cytometer using DiVa software (BD Biosciences). Results were evaluated using FlowJo software.

Monoclonal Antibodies

Fluorochrome-conjugated monoclonal antibodies against human IFNγ (clone B27, APC), IL-2 (clone MQ1-17H12, PE) CD8 (clone SK1, APC-Cy7), CD4 (clone RPA-T4, PB), CD30 (clone 50614, FITC), CD27 (clone M-T271, APC), CD 28 (clone L-293, PerCp-Cy5.5), CD34 (clone 8G12, PE-Cy7), PD1 (clone EH12.1, PE-Cy7), CD107a (clone H4A3, FITC) were purchased from BD Biosciences (San Diego, Calif.). Anti-CD19 (clone SJ25C1, PE) and anti-CD127 (clone eBio-RDR5, APC-eflour) antibodies were purchased from Caltag Laboratories (Life technologies Inc) and eBiosciences, respectively.

Surface Staining and Intracellular Cytokine Staining of CAR T Cells

For effector functional analysis, the CART cells were mixed with target cells in an E:T ratio of 1:3 overnight with the addition of 1.5 μl of FITC-conjugated anti-CD107a Ab. Positive control used T cells (without CAR) stimulated with PMA (1 μg/μl) and Ionomysin (1 ng/μl) for 1 hour. The intracellular cytokines were immobilized after treated with monensin (6 μg/μl) for 6 hours. The samples were then washed, blocked with 10% human and mouse sera for 30 min, stained with anti-CD4 and anti-CD8 Abs for 30 min, fixed and permeabilized with BD Fix/Perm Buffer, stained with anti-IFNγ and anti-IL-2 Abs for 1 hour, and then analyzed by flow cytometry. Data was collected on the BD LSRII flow cytometer and analyzed with FlowJo.

Results

The patient is a 22 year-old male. He was diagnosed with stage III Hodgkin's lymphoma (Nodular Sclerosis), and was treated with six cycles of ABVD and radiation to the residual disease. The response to this treatment was complete remission. Subsequently, the disease relapsed confirmed by biopsy of the left supraclavicular lymphadenopathy. After two cycles of COEP, disease kept progressing. The patient then received two cycles of ICE followed by partial remission. The patient was later treated with auto-transplant. This treatment resulted in complete remission. The disease relapsed again, with nodules in lung and mediastinal, abdominal, retroperitoneal lymphadenopathy. Subsequently, the patient was enrolled in a clinical trial of anti-CD30 chimeric antigen receptor-modified T cells.

Detection of CAR T Cells In Vitro

Figure 15:
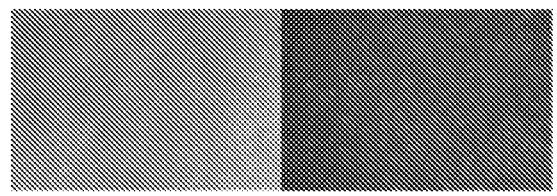
FIG. 15 shows data related to a target killing assay of two different CD30-CAR T cells based on 5F11 and AC10 scFv CD30-CARs.
Figure 15:
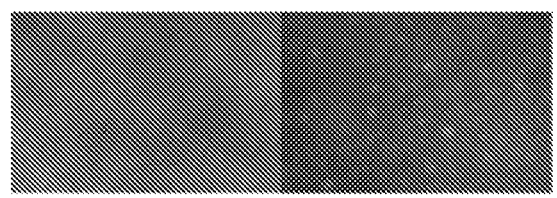
Figure 15:
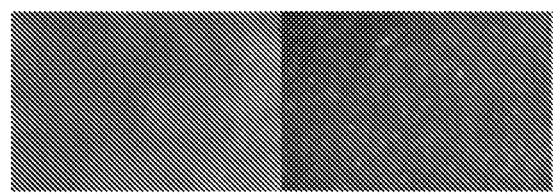
Figure 15:
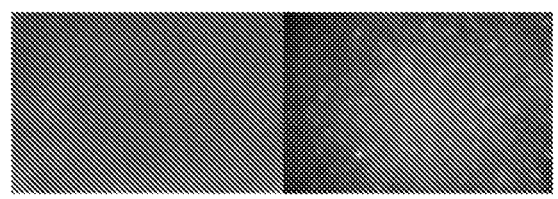
Figure 15:
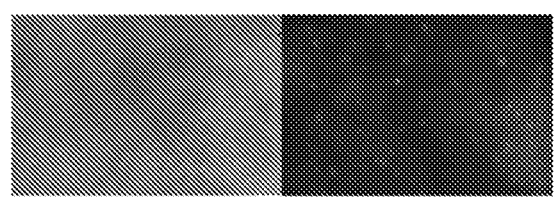

FIG. 15 shows a fluorescent image of target killing assay of two different CD30-CAR T cells based on 5F11 and AC10 scFv CD30-CARs. The primary lymphoma cell line was labeled with green fluorescent protein and used as target cells. CAR T cells and target cells were coincubated in a 96 U shaped well at 1:1 ratio for 12 days. The disappearance of green fluorescent indicates target cell killing by CAR T cells. The AC10 CD30-CAR displayed the best target killing activity.

Figure 16:
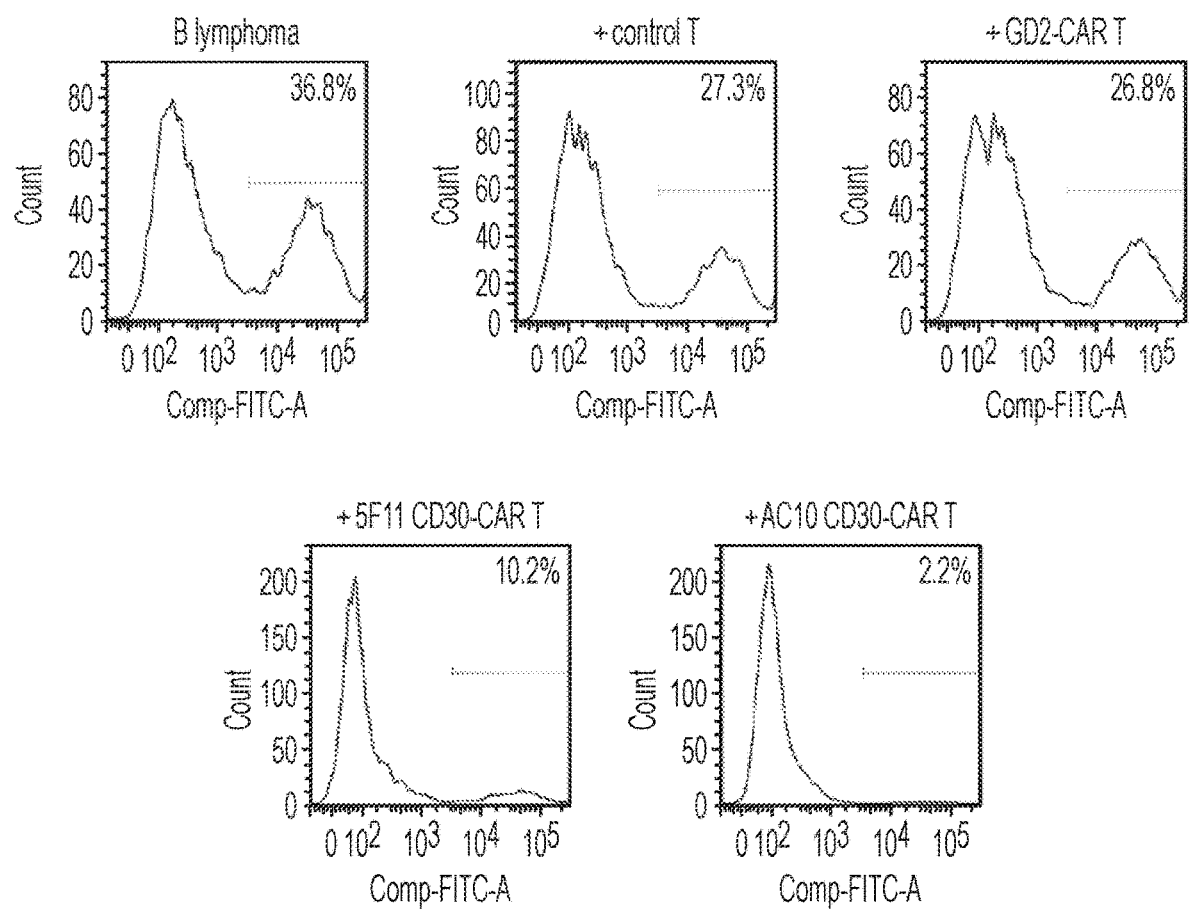
FIG. 16 shows flow cytometry target killing assay of two different CD30-CAR T cells based on 5F11 and AC10 scFv CD30-CARs.

FIG. 16 shows flow cytometry target killing assay of two different CD30-CAR T cells based on 5F11 and AC10 scFv CD30-CARs. The primary lymphoma cell line was labeled with green fluorescent protein and used as target cells. CAR T cells and target cells were coincubated in a 96 U shaped well at 1:1 ratio for 12 days. The disappearance of green fluorescent cells detected by flow cytometry indicates target cell killing by CAR T cells. The AC10 CD30-CAR displayed the best target killing activity.

Detection of CAR T Cells In Vivo

Figure 17:
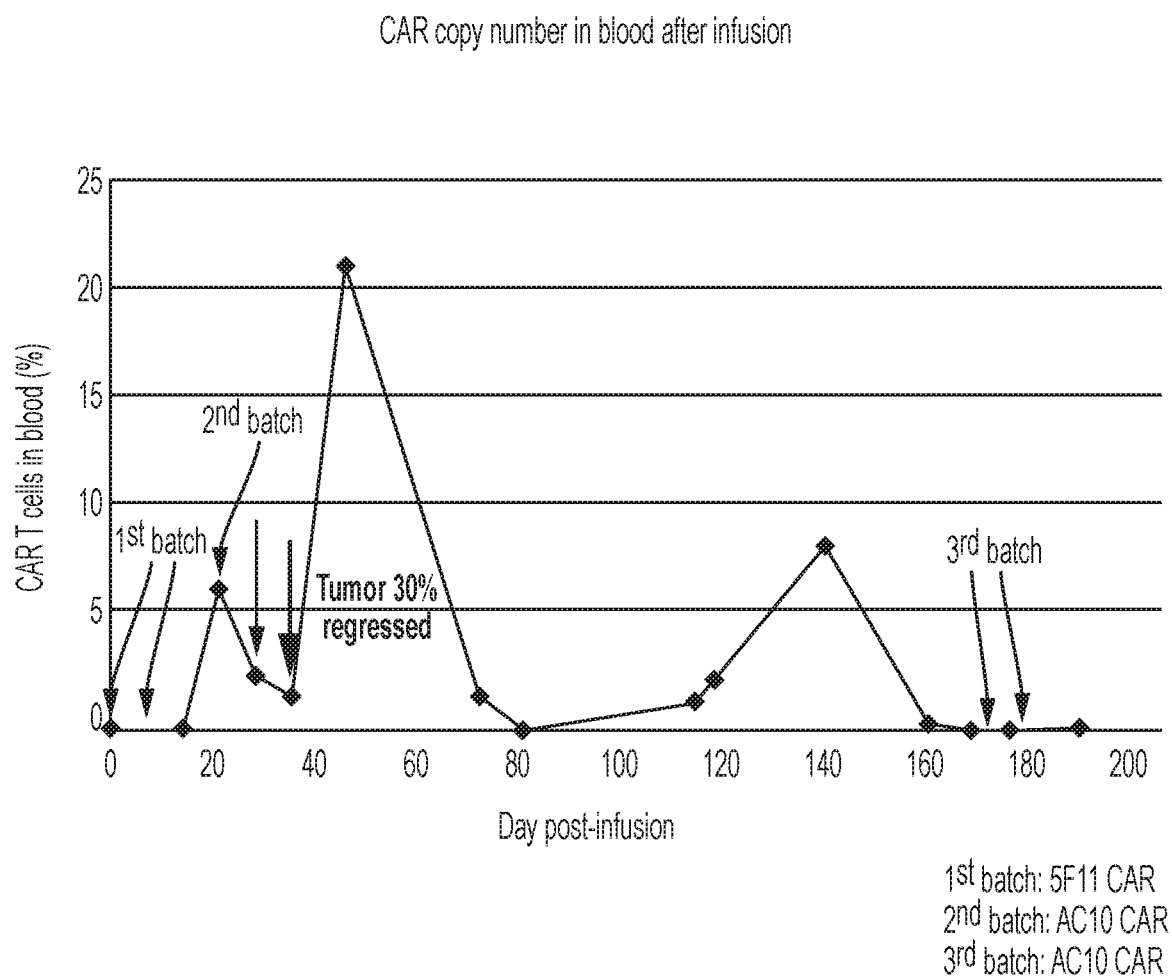
FIG. 17 shows the clinical course of a Hodgkin's lymphoma patient treated with CD30-CAR T cells. The infusion time point was depicted by arrows. Three batches of CAR T cells were prepared and infused as indicated. CAR-positive T cells were detected by qPCR detection of CAR DNA in the genome of blood cells. Clinical evidence of tumor regression was evident at day 40 after the first infusion.

Quantitative polymerase chain reaction was performed to detect CAR T cells in blood. The CD30-CAR T cells were detected on day 14 after first infusion. On day 45, CAR T cells reached its peak level accounting for more than 20% of circulating lymphocytes. This peak level of CAR T cells coincided with the observed disease remission and results of serum cytokine levels. CAR T cells decreased 80 days after cell infusion, which paralleled with disease progression. Interestingly, CAR T cells increased to ~8% again on day 140 indicating in vivo response to tumor relapse (FIG. 17).

Detection of Cytokine Response after CAR T Infusion

Figure 18:
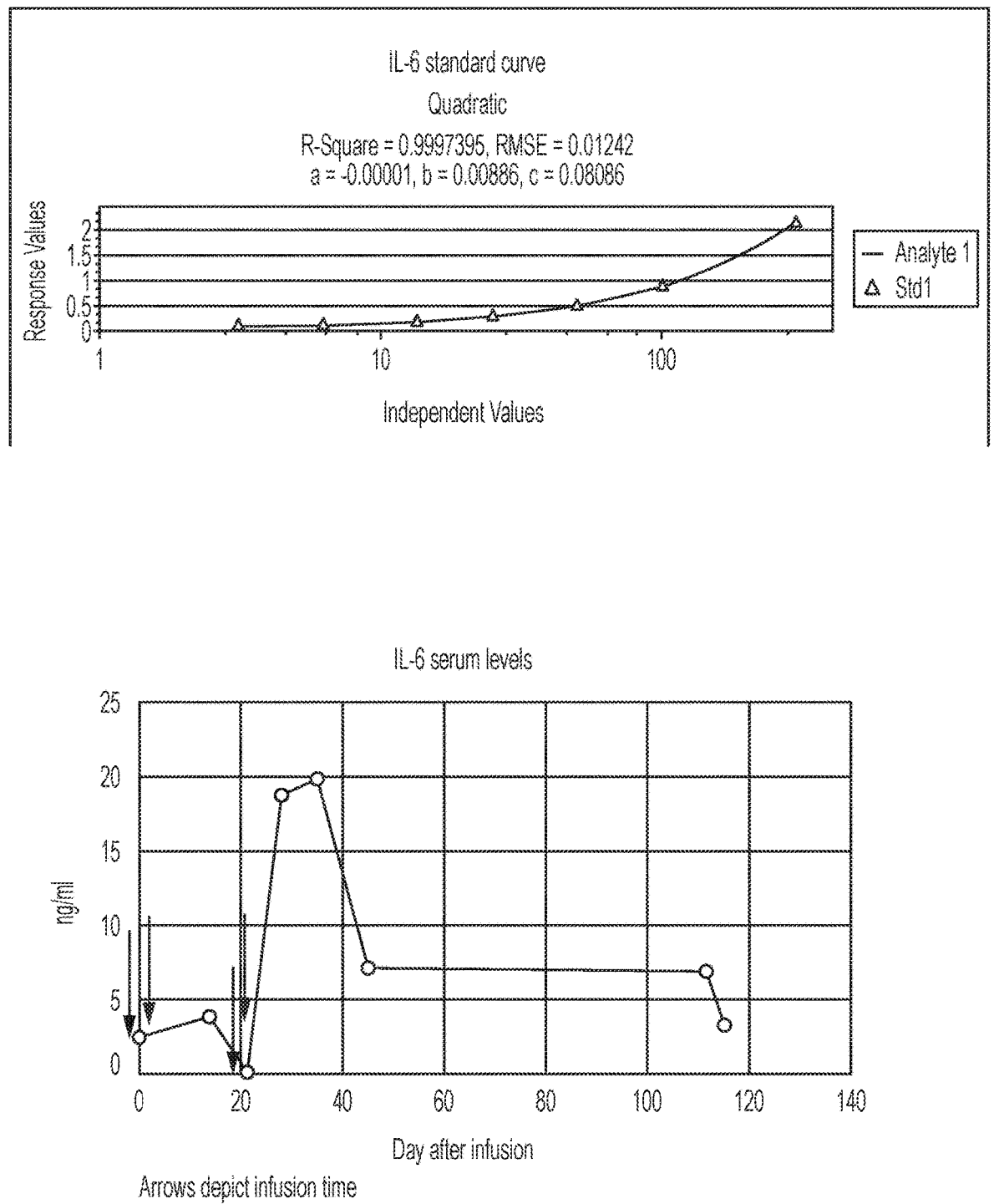
FIG. 18 shows data related to detection of IL-6 cytokine response after CD30 CAR T infusion.
Figure 19:
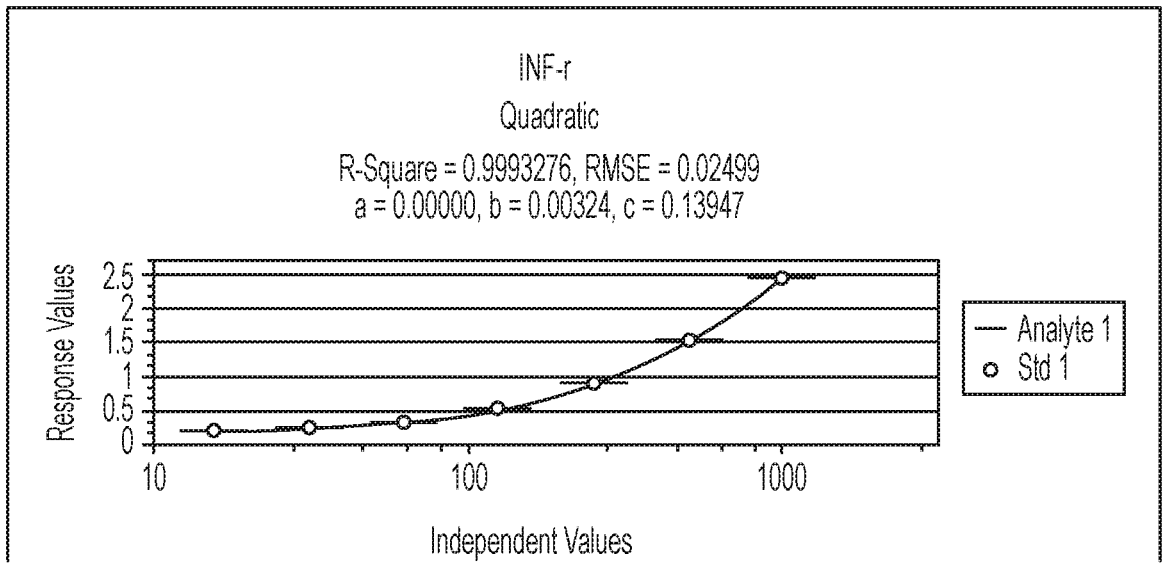
FIG. 19 shows data related to detection of IFN-gamma cytokine response after CD30 CAR T infusion.
Figure 19:
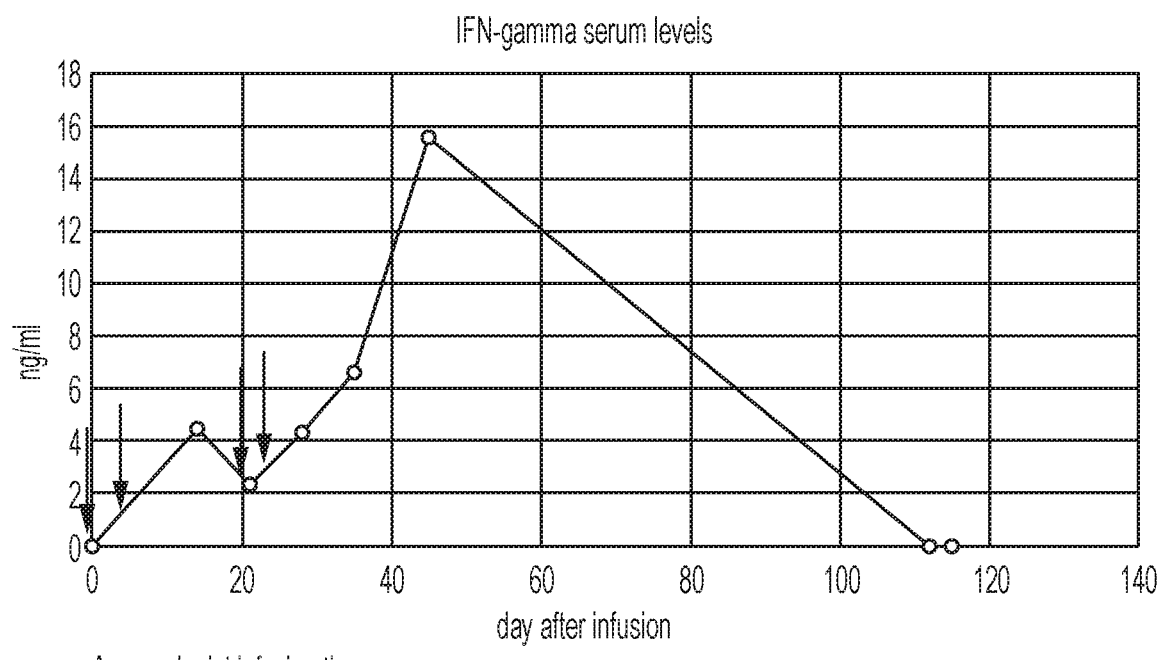

Serum cytokines were measured and showed evidence of immune activation. The patient's disease remission was accompanied by an increase in levels of inflammatory cytokines, with levels of interferon-γ and interleukin-6 peaking around 40 days after first cell infusion. The increase in serum cytokines paralleled with disease remission (FIGS. 18-19).

Example 3

Chimeric Antigen Receptor Expressing T Cells Mediate Activity Against Osteosarcomas Since the prognosis for children with high risk osteosarcoma (OS) remains suboptimal despite intensive multi-modality therapies, there is a clear and urgent need for the development of targeted therapeutics against these refractory malignancies. Chimeric antigen receptor (CAR) modified T cells can meet this need by utilizing the immune system's surveillance capacity and potent cytotoxic mechanisms against tumor specific antigen targets with exquisite specificity. Since OS highly expresses the GD2 antigen, a viable immunotherapeutic target, the study described herein sought to assess if CAR modified T cells targeting GD2 could induce cytotoxicity against OS tumor cell lines. It was demonstrated that the OS cell lines U2OS, HOS, and a primary human OS cell line highly express the GD2 antigen (>80%), and that GD2 CAR modified T cells were highly efficacious for inducing tumor cell death. Interestingly, the OS cells were induced to up-regulate expression of PD-L1 upon interaction with GD2 CAR modified T cells, and the specific interaction induced CAR T cells to overexpress the exhaustion marker PD-1 along with increased CAR T cell apoptosis. To further potentiate CAR T cell killing activity against OS, it was demonstrated that checkpoint blockade along the PD-L1/PD-1 axis can synergize with CAR T cell therapy. In addition, conventional chemotherapy in combination with CAR T cell therapy can also synergize the effects showing an increased target cell killing activities.

Materials and Methods

Cell Lines

HOS and U2OS cells were cultured at 37° C. in 4% CO2 atmosphere in Dulbecco's modified eagle medium; DMEM (GIBCO®, Life technologies, CA, USA) supplemented with 10% fetal bovine serum, 1% penicillin and 1% streptomycin.

Jurkat cells were cultured at 37° C. in 4% CO2 atmosphere in RPMI-1640 medium (GIBCO, Life Technologies) supplemented with 10% fetal bovine serum, 1% penicillin and 1% streptomycin.

Detection of GD2 Surface Expression

The ~80% confluent cells were harvested using 2.5 mM EDTA for HOS and 5 mM EDTA for U2OS. The cells were sampled, mixed with trypan blue and counted. For GD2 surface staining, $10^5$ cells were collected and washed twice with PBS and blocked with 10% human-mouse (1:1) serum in FACS buffer (2% FBS, 0.1% NaN3 in PBS) at 4° C. for 30 minutes. The cells were washed with FACS buffer and stained with PE conjugated anti-GD2 Ab (BD biosciences, CA, USA) and kept in the dark at 4° C. for 30 minutes. The cells were washed with FACS buffer and fixed with 1% paraformaldehyde in PBS. GD2 surface expression were detected by BD LSRII flow cytometer and analyzed with FlowJo. Percentage of GD2 expression and MFI were determined by subtraction background obtained from isotype control (PE conjugated mouse IgG2a, BD Pharmingen, CA, USA).

Construction of Lentiviral Vectors

Lentiviral vectors were generated using the NHP/TYF lentiviral vector system as previously described [16, 17]. CAR DNA was chemically synthesized and cloned into pTYF transducing vector behind human EF1α promoter using standard molecular cloning approaches. The final lentiviral-constructs were verified by restriction enzyme mapping and DNA sequencing.

Blood Donors, PBMC Isolation and T Cell Activation

Blood samples were obtained from a donation center or osteosarcoma patients. PBMC were isolated using Ficoll-Paque plus (GE Healthcare). T cells were activated using anti-CD3 and anti-CD28 antibody-conjugated magnetic beads or phytohemagglutinin (PHA). The T cells were maintained in TexMACS (Miltenyi Biotec Inc, San Diego, Calif.) or AIM-V (Invitrogen) supplemented with interleukin-2, -7 and -15 as previously described [18]. Phenotype analysis of the activated cells were verified to confirm T cell purity. After expansion for two to six days, the T cells were transduced with lentiviral CAR vectors and evaluated killing function.

GD2-CAR-T Cell Cytotoxicity Analysis

GFP-positive OS cells were prepared as single cell suspension as mentioned above. The cells were resuspended in DMEM growth medium at $1.5 \times 10^5$ cells/ml and 200 µl of the OS cells were seeded into 48-well plate and cultured at 37° C. in 5% CO2 for two hours. CAR-modified T cells (primary T cells or Jurkat cells) were added to the wells of OS cells at various effecter to target (E:T) ratio and co-cultured for various period of time in the present or absent of anti-PD-L1 antibody (BioLegend, CA, USA). The cells were monitored periodically under fluorescence microscope (Zeiss Axiovert 25) and photographed. For flow cytometer analysis of cell death, the cells were harvested using EDTA as described. The harvested cells were washed once with PBS and stained with Annexin V-V450 (BD Biosciences) and propidium iodide (Sigma) for 10 minutes at room temperature. After staining, the cells were resuspended in 1% paraformaldehyde in PBS. Data were collected by BD LSRII flow cytometer and analyzed with FlowJo. The difference of cell death between GD2 CAR-modified T cells and control-CAR T cells was analyzed by independent t-test with P value≤0.05 being significant. Percent specific lysis of target cells was calculated based on the following formulation [19]:

% specific lysis=(% apoptosis of target cell−% spontaneous cell apoptosis)/(100%−% spontaneous cell apoptosis)×100

PD-1 and PD-L1 Surface Staining of the Co-Cultured Cells

The co-cultured OS cells and CAR-modified T cells were harvested and blocked with 10% human-mouse (1:1) serum at 4° C. for 30 minutes. The cells were washed and stained with PE-Cy7 conjugated anti-PD-L1 (eBiosciences, CA, USA) or PE-Cy7 conjugated anti-PD-1 (BD Biosciences) at 4° C. for 30 minutes in the dark. The cells were washed with FACS buffer and fixed with 1% paraformaldehyde in PBS. PD-1 or PD-L1 surface expression was analyzed using BD LSRII flow cytometer and FlowJo software. For analysis of PD-1 expression in CAR-modified T cells, the FITC negative T cells were gated while for PD-L1 expression the FITC positive cells were gated. Percentage of PD-1 or PD-L1 expression and mean fluorescence index (MFI) were determined by subtraction of background isotype control (PE-Cy7 conjugated mouse IgG1κ; BD Biosciences).

Results

Analysis of GD2 Surface Expression in OS Cell Lines.

Figures 20A, 20B, 20C:
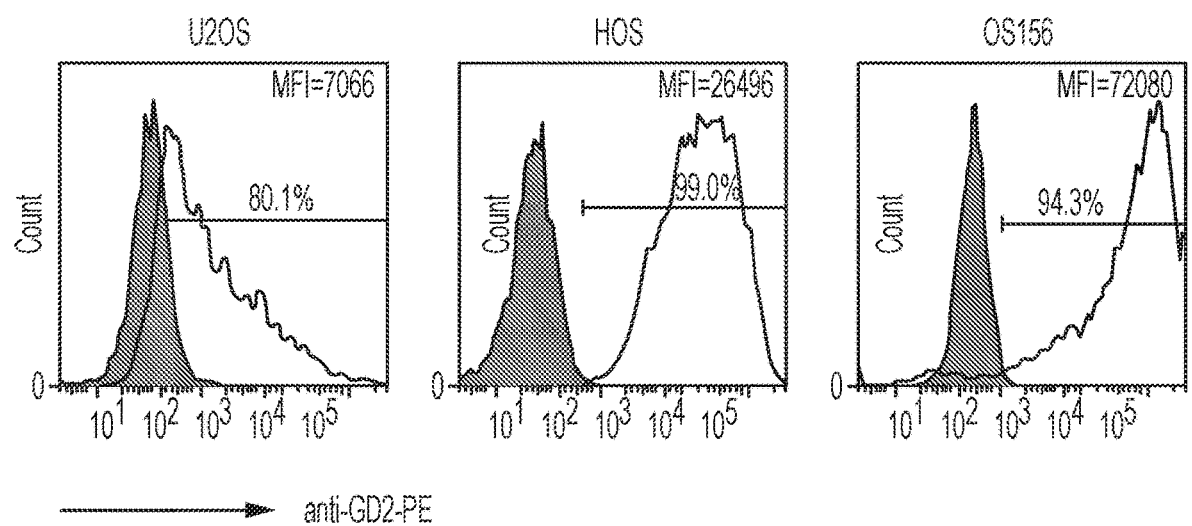
FIGS. 20A-20C shows graphs of exemplary GD2 surface expression in osteosarcoma (OS) cell lines. Flow cytometry histogram overlays show surface expression of GD2 in (FIG. 20A) HOS (FIG. 20B) U2OS and (FIG. 20C) OS156 cells. The dark line represents GD2 positive and the shadowed grey line represents isotype control. Inner number indicates percent positive population and mean fluorescence intensity (MFI) of the positive population
Figure 21A:
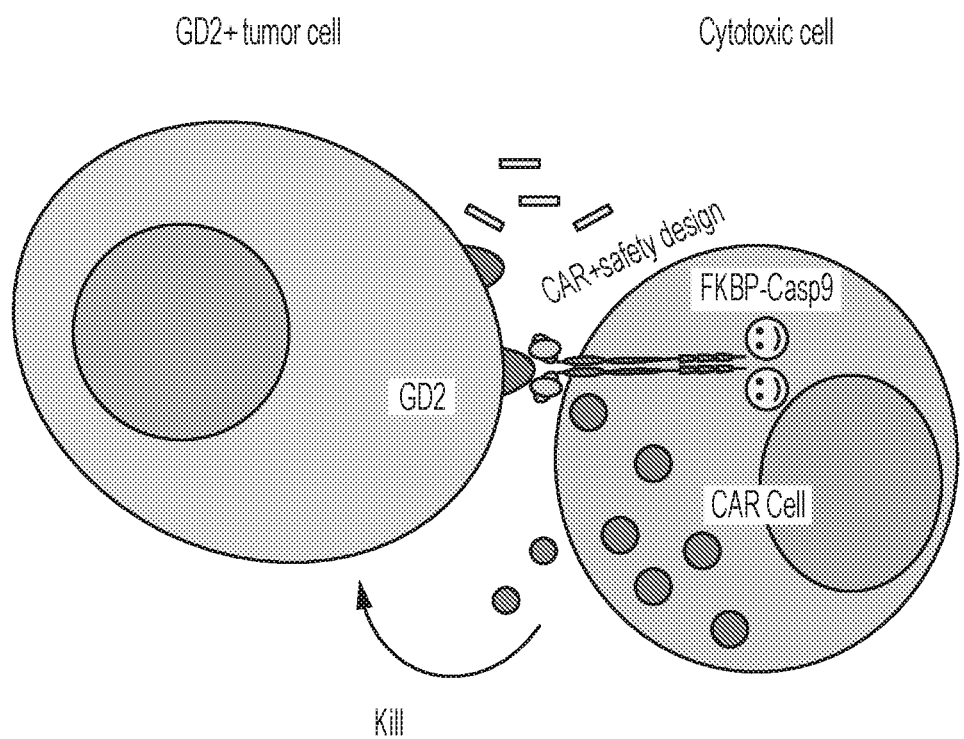
FIG. 21A is a schematic showing an exemplary CAR that targets GD2 binding to a cell expressing GD2.
Figure 21B:
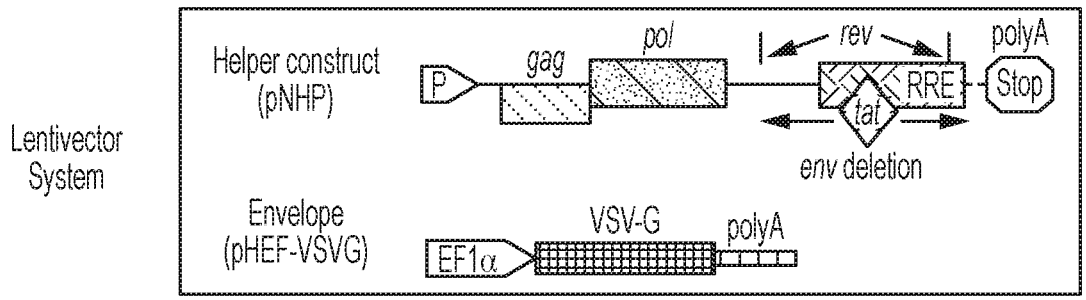
FIG. 21B is a schematic that shows embodiments of CAR molecules, including one embodiment of GD2 CAR construction and 4th generation CAR configurations.
Figure 21B:
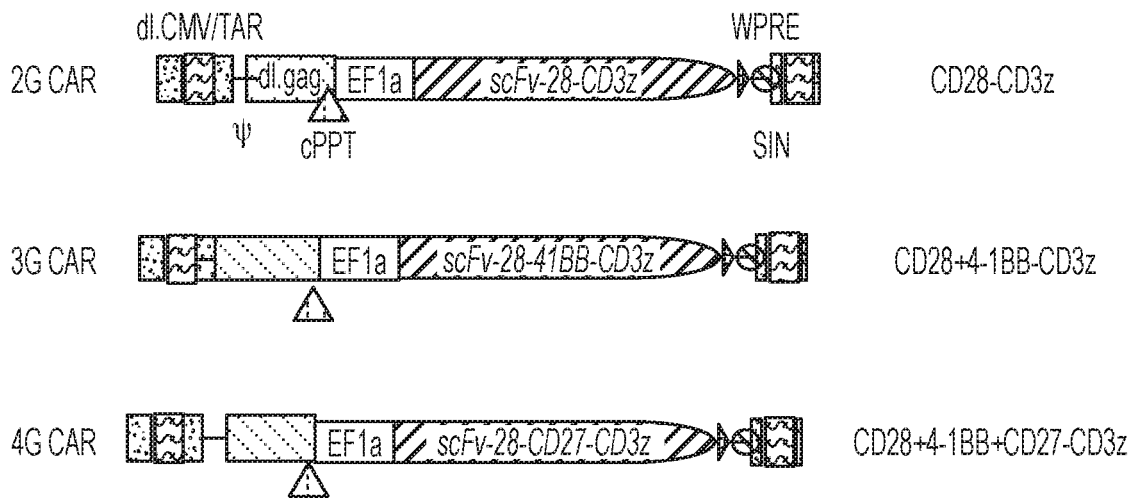
Figure 21B:
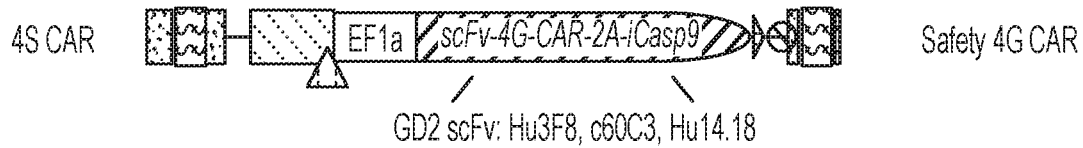

Two OS cell lines including HOS and U2OS cells were analyzed for expression of GD2 by flow cytometry. GD2 expression was found on both OS cell lines, 80.1% and 99% on U2OS and HOS cells, with MFI of 7,066 and 26,796, respectively (FIG. 20). In a primary OS cell culture, OS156, a high level of GD2 expression was detected (94.3%, MFI=72,080, FIG. 20).

Construction of 4th Generation GD2 CAR Lentiviral Vectors.

To engineer GD2-specific CARs, three humanized GD2-specific scFv clones, hu3F8, c.60C3 and hu14.18[15, 20, 21] were selected. These GD2 CAR sequences were then human codon-optimized and chemically synthesized. To establish 4th generation CARs, several intracellular T cell signaling motifs were incorporated in the CARs including CD28 transmembrane and cytoplasmic domain, the co-stimulatory 4-1BB intracellular TRAF binding domain, the CD27 cytoplasmic domain, and the CD3ζ chain intracellular domain as illustrated in FIG. 21. These CAR genes were cloned into the lentiviral vector pTYF and packaged into lentiviral particles for gene transfer.

```
hu3F8 scFv: (VH and VL linked by 218S linker which is underlined)
                                                  (SEQ ID NO: 19)
QVQLVESGPGVVQPGRSLRISCAVSGFSVTNYGVHWVRQPPGKGLEWLGVIW

AGGITNYNSAFMSRLTISKDNSKNTVYLQMNSLRAEDTAMYYCASRGGHYGY

ALDYWGQGTLVTVSSGSTSGSGKPGSSEGSTKGEIVMTQTPATLSVSAGERV

TITCKASQSVSNDVTWYQQKPGQAPRLLIYSASNRYSGVPARFSGSGYGTEF

TFTISSVQSEDFAVYFCQQDYSSFGQGTKLEIK

C60c3 ScFv: (VH and VL linked by 218S linker which is underlined
                                                  (SEQ ID NO: 20)
EVKLVESGGGLVLPGDSLRLSCATSEFTFTDYYMTWVRQPPRKALEWLGFIR

NRANGYTTEYNPSVKGRFTISRDNSQSILYLQMNTLRTEDSATYYCARVSNW

AFDYWGQGTTLTVSSGSTSGSGKPGSSEGSTKGDVVMTQTPLSLPVSLGDQA

SISCRSSQSLLKNNGNTFLHWYLQKSGQSPKLLIYKVSNRLSGVPDRFSGSG

SGTYFTLKISRVEAEDLGVYFCSQSTHIPYTFGGGTKLEIK

Hu14.18 scFv: (VH and VL linked by 218S linker which is underlined
                                                  (SEQ ID NO: 21)
EVQLVQSGAEVEKPGASVKISCKASGSSFTGYNMNWVRQNIGKSLEWIGAID

PYYGGTSYNQKFKGRATLTVDKSTSTAYMHLKSLRSEDTAVYYCVSGMEYWG
```

```
                        -continued
QGTSVTVSSGSTSGSGKPGSSEGSTKGDVVMTQTPLSLPVTPGEPASISCRS

SQSLVHRNGNTYLHWYLQKPGQSPKLLIHKVSNRFSGVPDRFSGSGSGTDFT

LKISRVEAEDLGVYFCSQSTHVPPLTFGAGTKLELK
```

The above scFv domains were linked to the following CAR-inducible caspase 9 sequence (domain names are listed after each domain in bold);

```
(CD28 transmembrane domain)
FWVLVVVGGVLACYSLLVTVAFIIFWV (4-1BB intracellular domain)
KRGRKKLLYIFKQPFMRPVQTTQEEDGCSCRFPEEEEGGCEL (CD27 intracellular domain)
QRRKYRSNKGESPVEPAEPCHYSCPREEEGSTIPIQEDYRKPEPACSP (218S linker)
GSTSGSGKPGSSEGSTKG (CD3zeta)
RVKFSRSADAPAYKQGQNQLYNELNLGRREEYDVLDKRRGRDPEMGGK

PRRKNPQEGLYNELQKDKMAEAYSEIGMKGERRRGKGHDGLYQGLSTA

TKDTYDALHMQALPPR (218S linker)
GSTSGSGKPGSSEGSTKG (truncated Casp9)
VGALESLRGNADLAYILSMEPCGHCLIINNVNFCRESGLRTRTGSNID

CEKLRRRFSSLHFMVEVKGDLTAKKMVLALLELAQQDHGALDCCVVVI

LSHGCQASHLQFPGAVYGTDGCPVSVEKIVNIFNGTSCPSLGGKPKLF

FIQACGGEQKDHGFEVASTSPEDESPGSNPEPDATPFQEGLRTFDQLD

AISSLPTPSDIFVSYSTFPGFVSWRDPKSGSWYVETLDDIFEQWAHSE

DLQSLLLRVANAVSVKGIYKQMPGCFNFLRKKLFFKTS (FKBP domain)
                                    (SEQ ID NO: 37)
MGVQVETISPGDGRTFPKRGQTCVVHYTGMLEDGKKVDSSRDRNKPFK

FMLGKQEVIRGWEEGVAQMSVGQRAKLTISPDYAYGATGHPGIIPPHA

TLVFDVELLKLE
```

Functional Evaluation of GD2-CARs Based on a Rapid Killing Assay.

Figure 22:
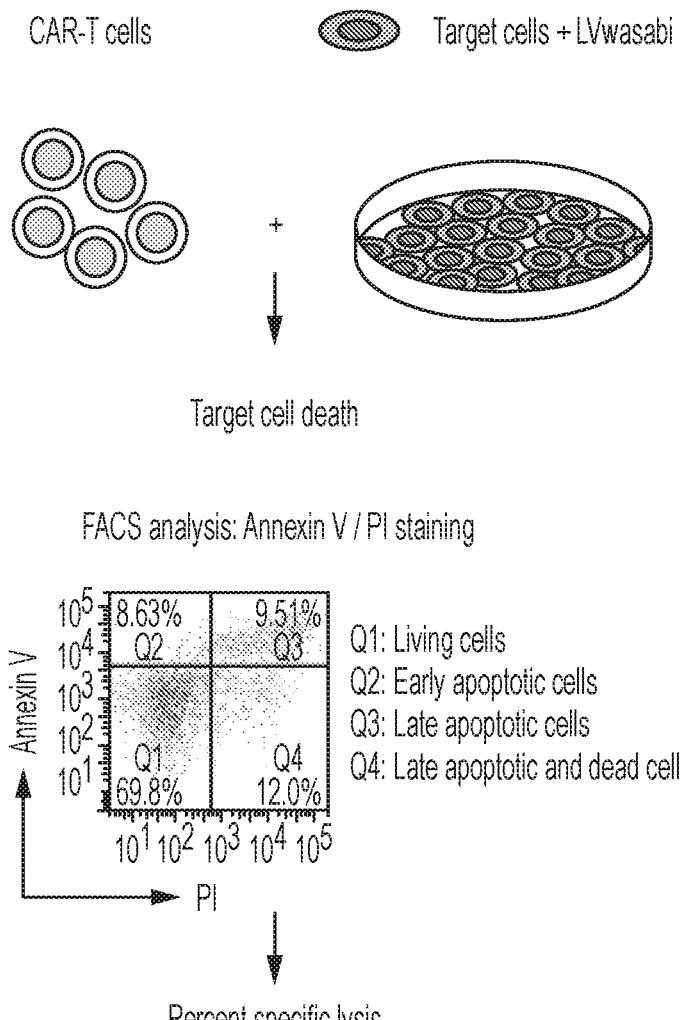
FIG. 22 is a diagram that shows an exemplary CAR-JK/T cell killing assay.

A simple and quick killing assay was developed to demonstrate GD2-CAR-mediated specific killing of OS cells. The assay was based on co-incubation of CAR-modified T cells and green fluorescent (wasabi GFP) GD2-positive OS cells. CAR T cells (effectors) were incubated with green target cells at different effector/target ratios, and at various time points, the cultured cells were analyzed by flow cytometry after staining with annexin V and propidium iodide (PI). FIG. 22 demonstrates the killing assay; the target cell death is detected by disappearance of green cells shown by change in E/T ratios and increased apoptotic and PI-stained dead cells. The hu3F8 CAR was chosen as the focus for the following experiments.

GD2-CAR-T Cell Cytotoxicity Against OS Cell Lines.

Figure 23A:
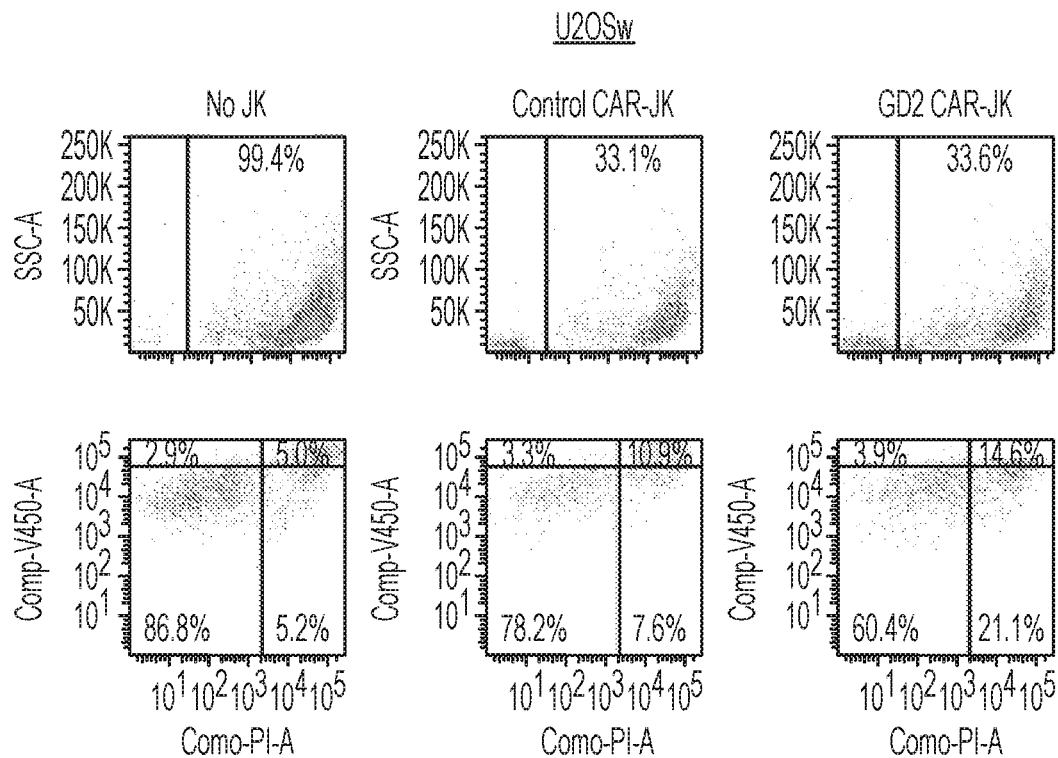
FIGS. 23A-23D are a series of plots and graphs that show short term GD2 JK killing. JK cells were used for CAR construction as a preliminary determination of GD2 CAR killing ability.
Figure 23B:
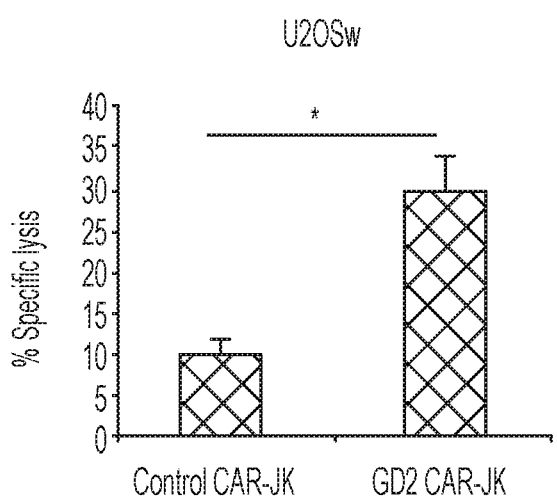
Figure 23C:
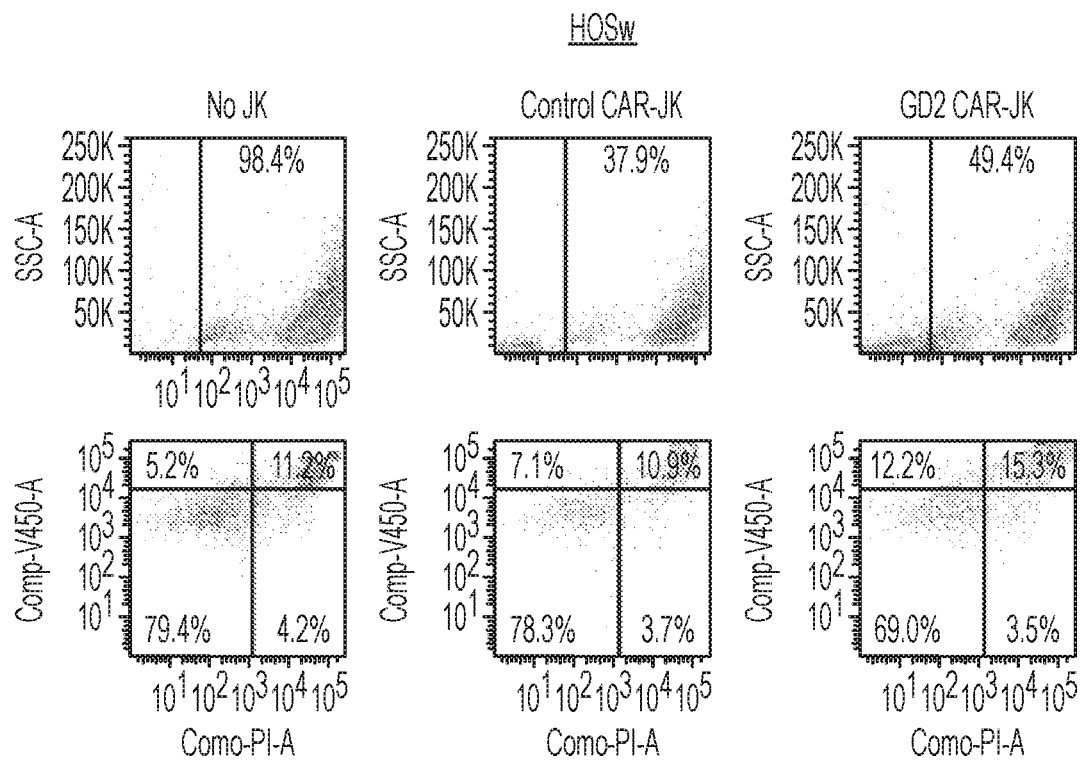
Figure 23D:
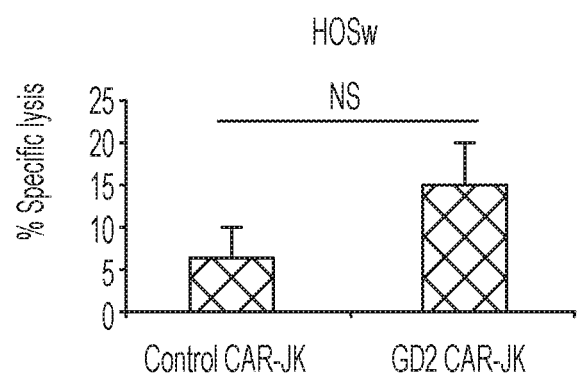

To demonstrate specific OS killing, the target U2OS and HOS cells were transduced with a lentiviral green fluorescence wasabi gene to generate U2OSw and HOSw reporter cell lines. The percent specific lysis was assessed for early and late apoptosis by flow cytometric analysis of Annexin V and PI. In a simplified assay, JK cells were transduced with GD2-CAR or control CD19-CAR and cocultured with U2OSw or HOSw to assess the CAR-T killing ability. Compared with control (non-specific) CD19-CAR-JK cell, the percent specific lysis by GD2 CAR-JK cells was significantly increased against U2OSw (FIG. 23A, B; p=0.0049). Similar trend was observed against HOSw (FIGS. 23C, 23D, p=0.078).

Primary GD2 CAR T Cells Targeting Established and Primary OS Cell Lines.

Figure 24E:
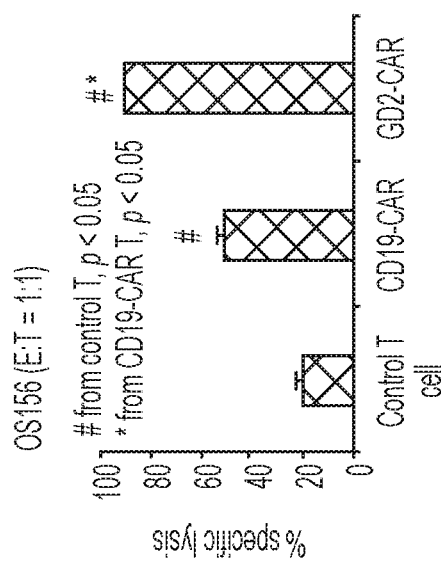
Figure 24F:
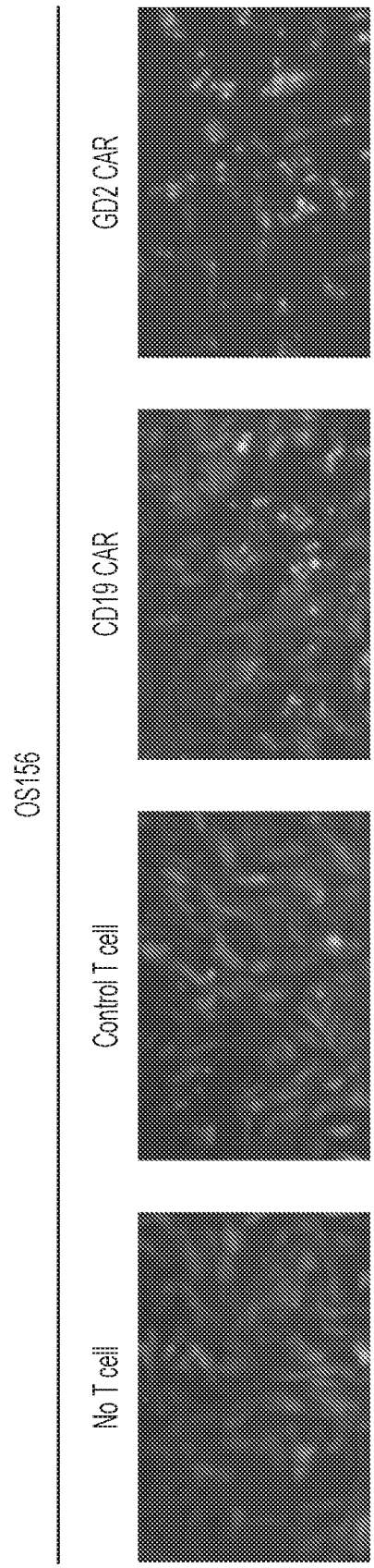

Primary T cells from healthy donors were transduced with GD2 CAR and co-cultured with OS cell lines U2OSw and HOSw in a series of effecter to target ratios (4:1, 2:1, 1:1 and 1:2), and the cells were harvested and evaluated after 1 day. Compared with control T cells and/or non-specific CAR (CD19-CAR), percent specific lysis of U2OSw was increased when co-cultured with GD2 CAR T cells but not with non-specific control CD19-CAR T cells (FIGS. 24A, 24B). Similar results were obtained with HOSw cells using GD2-CAR T cells but not another non-specific glypican 3 (GPC3)-CAR T cells (FIGS. 24C, 24D). To see if the OS target killing effects could be detected with primary tumor cell line, the OS156 cells, established from an OS patient, was tested for GD2-CAR T killing assay. A green fluorescent wasabi gene modified OS156 cell line, OS156w, was generated and used as target cells. After 1 day co-cultured at E:T ratio 1:1, GD2 CAR-T cells also efficiently killed the primary OS156w cells as illustrated by specific lysis of target cells and decreased green fluorescent target cells (FIGS. 24E, 24F).

Figure 24G:
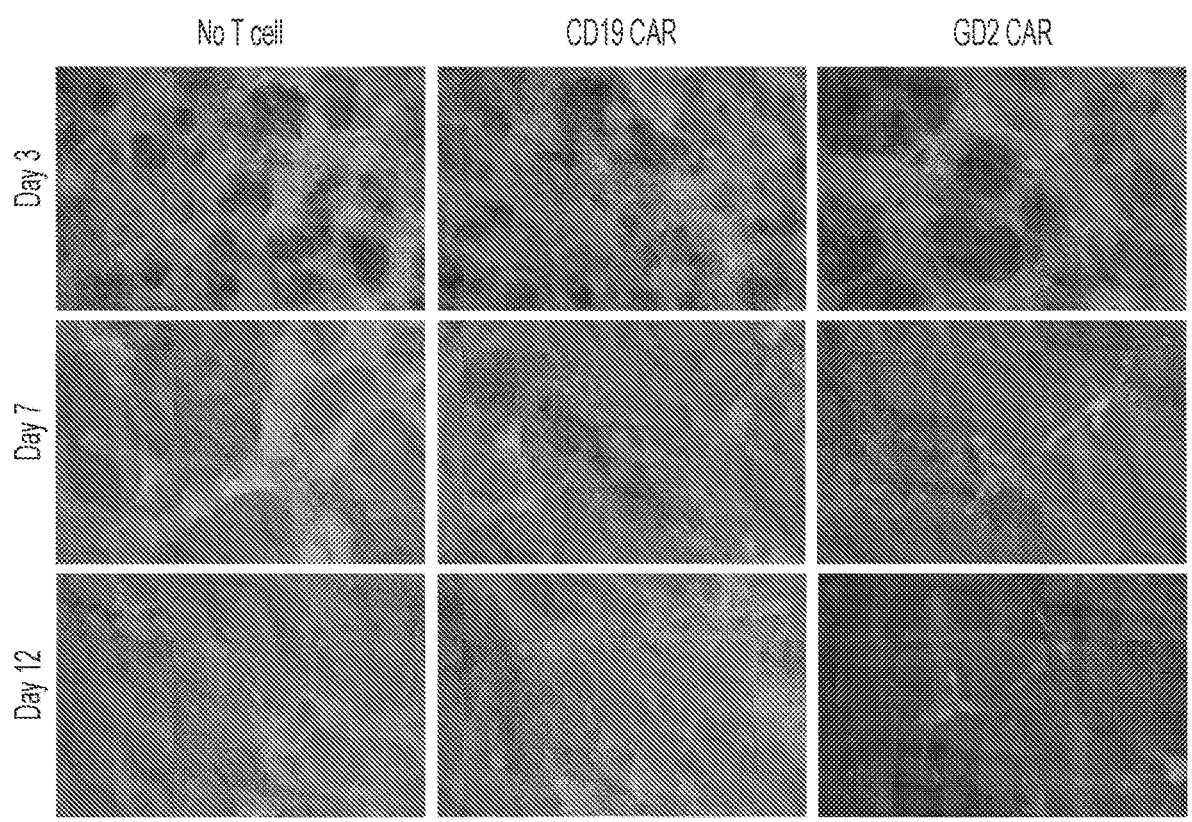

To see if the GD2-CAR T cells could kill target tumors for extended period, after the first coculture when all tumors cells were killed, more tumor cells were added to the GD2-CAR T cells to set up a second round killing, at E:T ratio=1:3. Evident under fluorescent microscope, the results showed that GD2 CAR-T cells, but not control T cells or non-specific CD19-CAR T cells, were able to killed HOSw cells even with the increased tumor ratio after 12 days in culture (FIG. 24G).

Specific Induction of PD-L-1 on OS cells and PD-1 on GD2-CAR T.

Figure 25A:
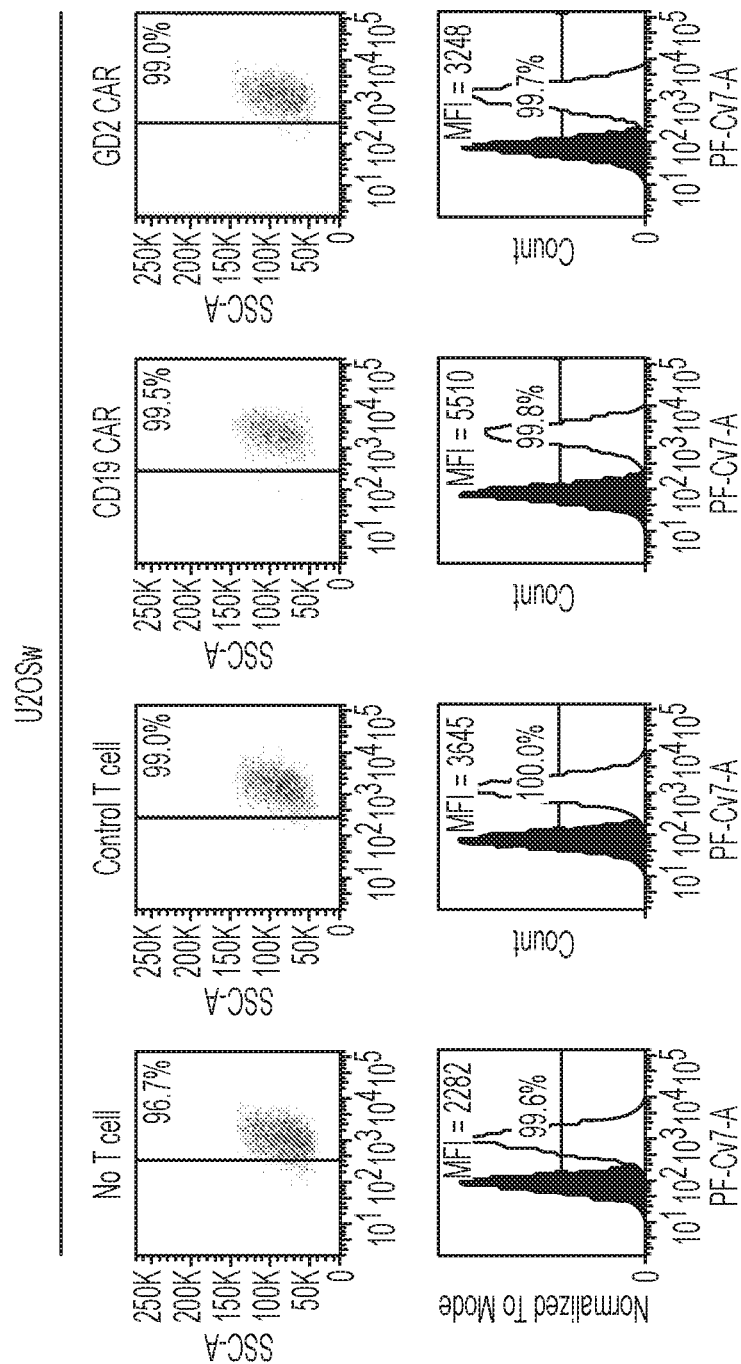
FIGS. 25A-25D show exemplary PDL-1 expression in OS cells after incubation with CAR T cells.
Figure 25B:
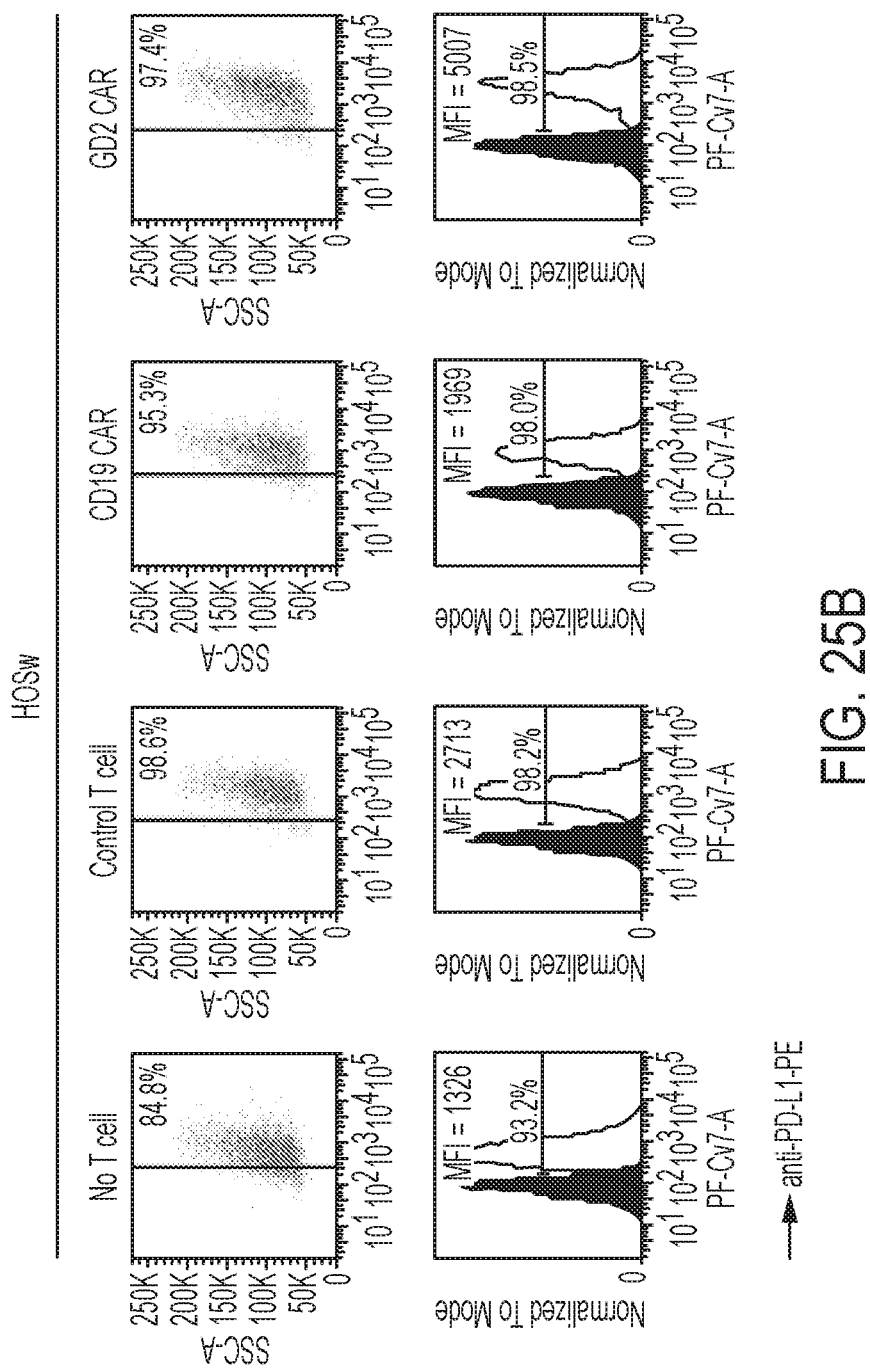
Figure 25C:
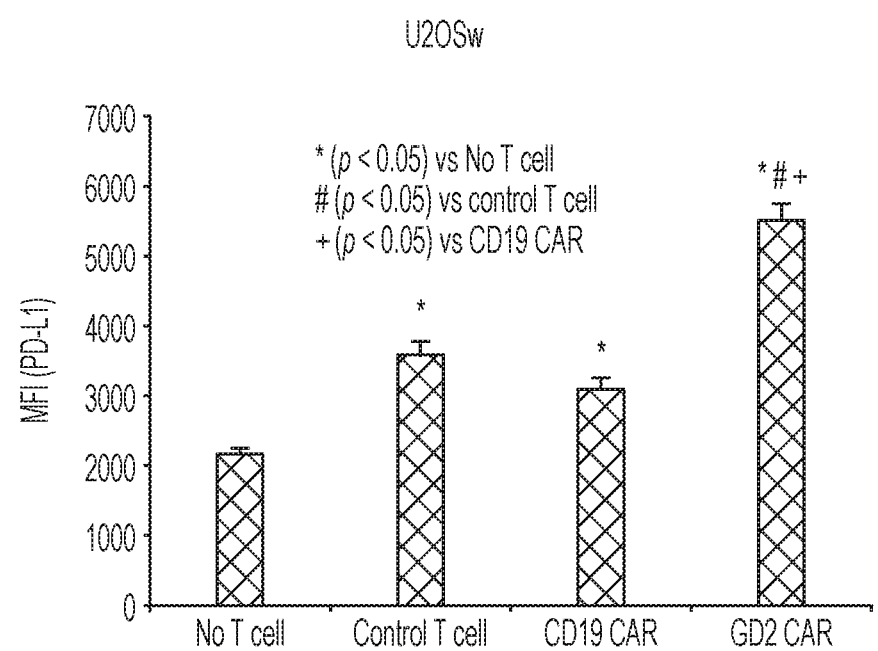
Figure 25D:
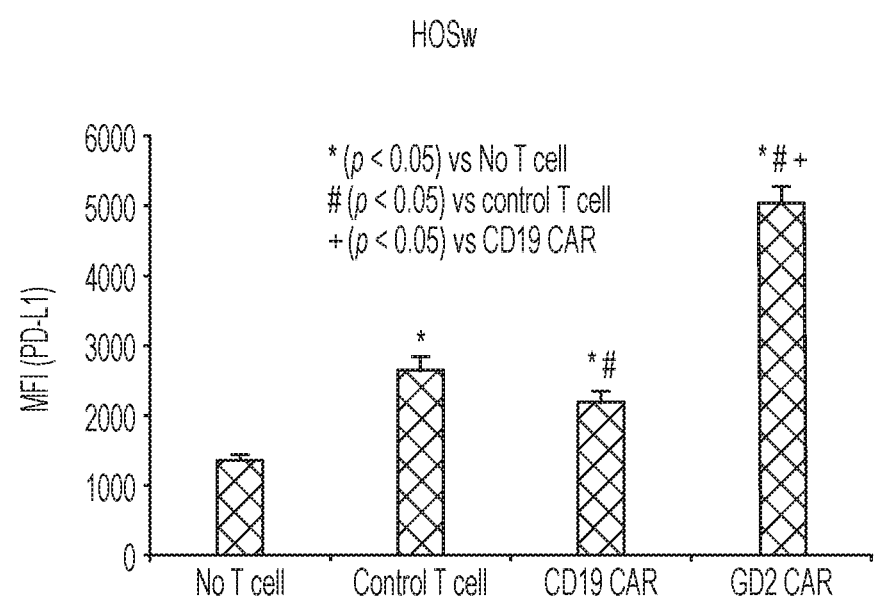
Figure 26A:
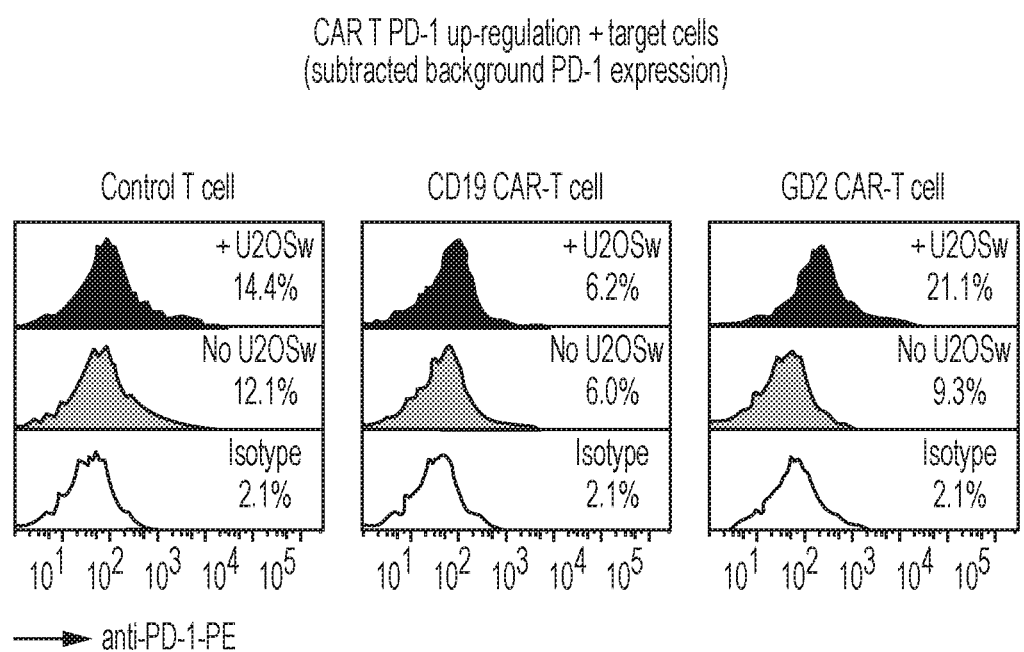
FIGS. 26A-26F show exemplary PD-1 expression in CAR T cells after incubation with OS cells. PD1 expression in primary CAR T cells after 1 day co-culture with target cells (E:T ratio=2:1), U2OSw (FIGS. 26A-26B) and HOSw (FIGS. 26D-26E). A bar graph displays fold increase of PD1 expression from background expression level. The number above the bars show fold increase of PD1 expression.
Figure 26B:
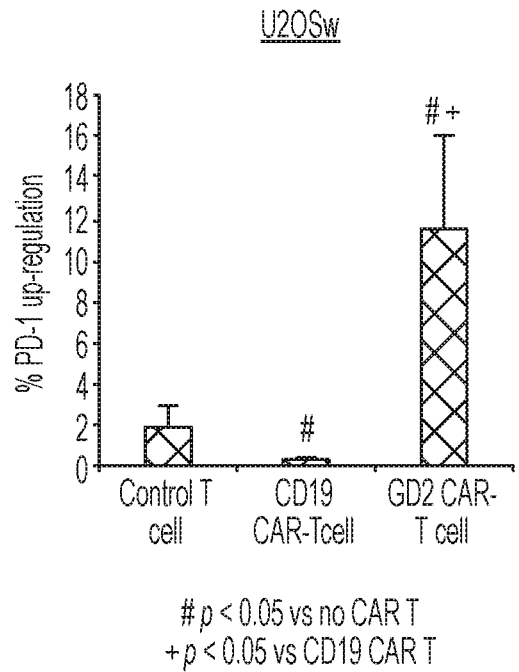
Figure 26C:
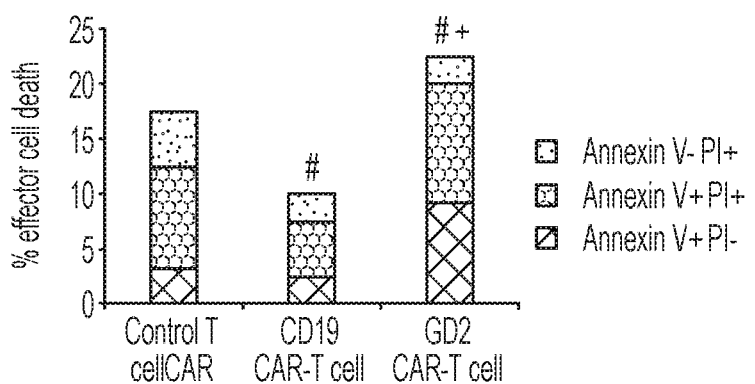
Figure 26D:
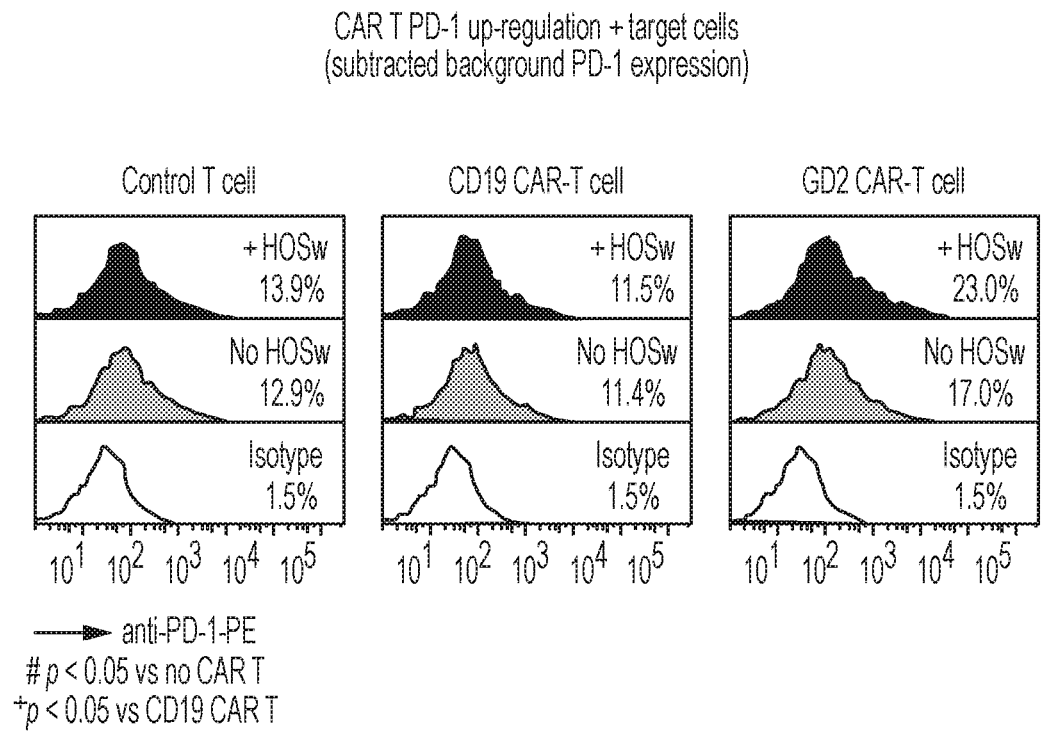
Figure 26E:
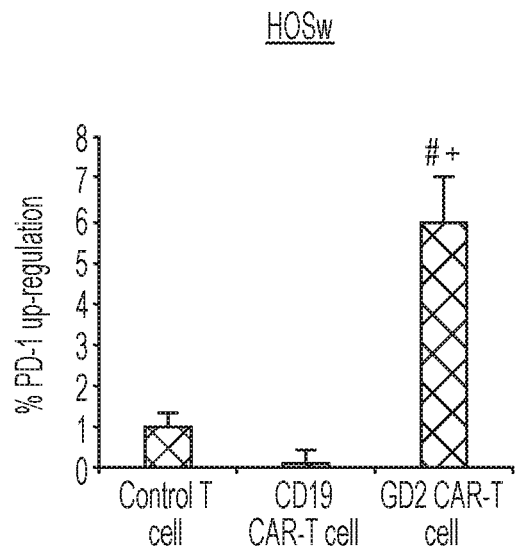
Figure 26F:
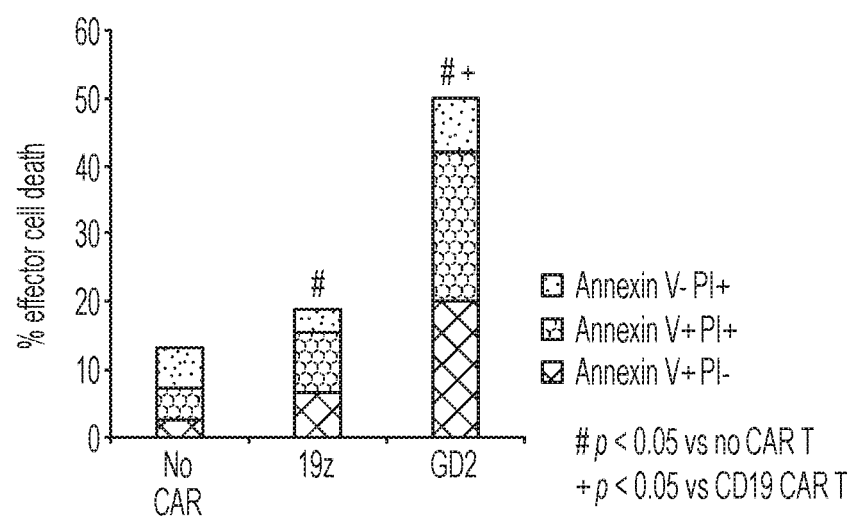

PD-L1 expression is a key immune evasion mechanism of tumor cells[22]. Flow cytometry histogram overlays revealed basal expression of PD-L1 on surface of both HOS and U2OS cells (FIGS. 25A,25B). Upon specific interaction with GD2 CAR T cells, up-regulation of PD-L1 in the co-cultured OS cells was observed as illustrated by increased MFI for PD-L1 signal, as compared with the cells co-cultured with control T cells and CD19 CAR-T cells (FIGS. 25C,25D).

PD-L1 Functions as a Ligand of PD-1 Related to Immune Checkpoint Inhibition of T Cells Functions.

PD-1 expression was next examined on primary CAR T cells. The result showed that primary GD2 CAR T cells displayed increased PD-1 expression when compared to control T cells and non-specific CD19-CAR T cell after 1-day co-cultured with U2OSs and HOSw cells (FIGS. 26A,26B,26C, and 26D,26E,26F, respectively, p<0.05).

Example 4

Disialoganglioside (GD2)-Specific Chimeric Antigen Receptor T Cells has a High Potent Anti-Tumor Activity on Retinoblastoma Cells Retinoblastoma (Rb) is an aggressive eye cancer that is the most common malignant in infant and children. Decreased doses of chemotherapeutic treatments in infant are considered, however, Rb tumors trend to increase resistant to the drug. One of the alternative approaches is immunotherapy based on using chimeric antigen receptor (CAR)-engineered T cells targeting tumor-specific antigens that are highly expressed on Rb tumor, but are present at low levels or not at all in normal tissues. Disialoganglioside 2 (GD2) protein might be a promising target antigen. Therefore, this study aims to investigate the killing efficiency of GD2-specific CAR T cells to eradicate Rb tumor cells in vitro.

Materials and Methods

Cell Culture and Reagents

The human retinoblastoma cell line Y79 RB cells were cultured in suspension in RPMI-1640 medium (Gibco® Life Technologies, USA) supplemented with 15% (v/v) fetal bovine serum (FBS) and 1% Penicillin-Streptomycin solution, and maintained in a 37° C. incubator with 5% $CO_2$. Cytokines recombinant human interleukin (IL)-2, IL-7, and IL-15 (μμg/ml) were purchased from a commercial vendor. AnnexinV-PE and propidium iodide (PI) were purchased from BD Biosciences (BD, USA). Carboplatin was purchased from Sigma.

Generation of GD2 Specific Chimeric Antigen Receptor Lentiviral Constructs

To engineer GD2-specific CARs, the humanized GD2-specific scFv clone, hu3F8 [15] was selected. The GD2 CAR sequence were then human codon-optimized and chemically synthesized. To establish 4th generation CARs, several intracellular T cell signaling motifs were incorporated in the CAR including CD28 transmembrane and cytoplasmic domain, the co-stimulatory 4-1BB intracellular TRAF binding domain, the CD27 cytoplasmic domain, and the CD3 chain intracellular domain as illustrated in FIG. 12. The CAR gene was cloned into the lentiviral vector pTYF and packaged into lentiviral particles for gene transfer.

hu3F8 scFv: (VH and VL linked by 218S linker which is underlined)
(SEQ ID NO: 19)
QVQLVESGPGVVQPGRSLRISCAVSGFSVTNYGVHWVRQPPGKGLEWL

GVIWAGGITNYNSAFMSRLTISKDNSKNTVYLQMNSLRAEDTAMYYCA

SRGGHYGYALDYWGQGTLVTVSS<u>GSTSGSGKPGSSEGSTKG</u>EIVMTQT

PATLSVSAGERVTITCKASQSVSNDVTWYQQKPGQAPRLLIYSASNRY

SGVPARFSGSGYGTEFTFTISSVQSEDFAVYFCQQDYSSFGQGTKLEI

K

The above scFv domain was linked to the following CAR-inducible caspase 9 sequence (domain names are listed after each domain in bold);

(CD28 transmembrane domain)
FWVLVVVGGVLACYSLLVTVAFIIFWV (4-1BB intracellular domain)
KRGRKKLLYIFKQPFMRPVQTTQEEDGCSCRFPEEEEGGCEL (CD27 intracellular domain)
QRRKYRSNKGESPVEPAEPCHYSCPREEEGSTIPIQEDYRKPEPACSP (218S linker)
GSTSGSGKPGSSEGSTKG (CD3zeta)
RVKFSRSADAPAYKQGQNQLYNELNLGRREEYDVLDKRRGRDPEMGGK

PRRKNPQEGLYNELQKDKMAEAYSEIGMKGERRRGKGHDGLYQGLSTA

TKDTYDALHMQALPPR (218S linker)
GSTSGSGKPGSSEGSTKG (truncated Casp9)
VGALESLRGNADLAYILSMEPCGHCLIINNVNFCRESGLRTRTGSNID

CEKLRRRFSSLHFMVEVKGDLTAKKMVLALLELAQQDHGALDCCVVVI

LSHGCQASHLQFPGAVYGTDGCPVSVEKIVNIFNGTSCPSLGGKPKLF

FIQACGGEQKDHGFEVASTSPEDESPGSNPEPDATPFQEGLRTFDQLD

AISSLPTPSDIFVSYSTFPGFVSWRDPKSGSWYVETLDDIFEQWAHSE

DLQSLLLRVANAVSVKGIYKQMPGCFNFLRKKLFFKTS (FKBP domain)
(SEQ ID NO: 37)
MGVQVETISPGDGRTFPKRGQTCVVHYTGMLEDGKKVDSSRDRNKPFK

FMLGKQEVIRGWEEGVAQMSVGQRAKLTISPDYAYGATGHPGIIPPHA

TLVFDVELLKLE

Retinoblastoma Cell Line and T Cells

Y79RB, a GD2 positive retinoblastoma cell line, and Jurkat T cell line were obtained from American Type Culture Collection (ATCC). These cell lines were maintained in RPMI1640 medium (Life Technologies, Inc. Grand Island, N.Y.) supplemented with 10% fetal bovine serum (Atlanta Biologicals, Inc. Norcross, Ga.), penicillin (100 units/ml) and streptomycin (100 ug/ml). Target cancer cell lines were transduced with lentiviral vectors expressing a green fluorescent protein (wasabi GFP gene) and the reporter gene positive cells were sorted by flow cytometry or selected with puromycin. Jurkat T cells were transduced with lentiviral CAR vectors and the copy number of CAR per cell was determined by quantitative PCR using genomic DNA.

Blood Donors and Primary T Cell Culture

Buffy coats from healthy donors (HDs) were purchased from LifeSouth Civitan Blood Center (Gainesville, Fla., USA) with approval of an Institutional Review Board. PBMCs were isolated from buffy coats by gradient density centrifugation in Ficoll-Hypaque (GE Healthcare Bio-Sciences AB, Piscataway, N.J., USA) as previously described [21]. T cells were activated using anti-CD3 and anti-CD28 antibodies. The T cells were maintained in TexMACS medium (Miltenyi Biotec Inc, San Diego, Calif.) supplemented with interleukin-2, -7 and -15 as previously described[20]. Phenotype analysis of the activated cells by flow cytometry was performed to confirm T cell purity. After expansion for two to six days, the T cells were transduced with lentiviral CAR vectors.

Lentiviral Vector Construction and CAR Gene Transduction

Lentiviral vectors were generated based on the NHP/TYF lentiviral vector system as previously described [22,23].

CAR DNA was chemically synthesized and cloned into pTYF transducing vector behind human EF1α promoter. The final lentiviral-CAR constructs were verified by restriction enzyme mapping and DNA sequencing.

CAR Detection by PCR

The CAR transgene copy numbers in CART cells were determined by quantitative SYBR green real time PCR (qRT-PCR) as previously described [20]. Genomic DNA was harvested from CART cells using Promega Wizard genomic DNA purification kit (Promega Corp. Madison, Wis.). The qRT-PCR reaction condition was as suggested by SABioscience and data collected using MX3000P (Stratagene, Agilent Technologies, Santa Clara, Calif.).

Generation of GD2-Specific Chimeric Antigen Receptor (CAR) T-Cells

Peripheral blood mononuclear cells (PBMCs) were isolated by Ficoll-Hypaque density gradient centrifugation, from healthy individuals. Lymphocytes were stimulated by phytohemagglutinin (PHA) treatment for 2-3 days and maintained in TexMACS™ medium (Miltenyi Biotec, CA, USA). Activated lymphocytes were transduced with CD19- or GD2-specific lentiviral particles and maintained in TexMACS™ medium supplemented with human IL-2 (40 U/ml), IL-7 (20 U/ml), and IL-15 (10 U/ml) for 3-4 days.

Immunohistochemistry

Tumor samples from RB patients were fixed and embedded in paraffin blocks.

Tumor Cell Cytolysis Assay

Y79 RB wasort cells (target (T) cells) were co-cultured with effector (E) T cells at various effector:target ratios (E:T) in the wells of 96-well flat-bottom plate at 37° c. for 24 hours. Target cell lysis was monitored under a fluorescence microscope and the cells were collected. Cell death was analyzed using AnnexinV/PI staining by flow cytometry. Specific cell lysis was calculated as [(apoptosis of target cells in co-culture–spontaneous target cells apoptosis)/(100–spontaneous target cells apoptosis)]×100. Spontaneous target cell death was considered as the percentage target cell death that cultured in T cell media without effector T cells. The results were representative of three independent experiments.

Flow Cytometric Analysis

To determine the expression of GD2 on the surface of primary neuroblastoma (NB8858) cells and Y79 RB cells, the cells were stained with PE-conjugated mouse anti-human GD2 mAb clone 14.G2a (BD Biosciences, CA, USA). Antibody staining was monitored with a BD LSRII flow cytometer. Data analysis was carried out using FlowJo software (Tree Star Inc., Ashland, Oreg.). For PD-L1 expression, cells were stained with anti-human CD274 or PD-L1 conjugated with PE-Cyanine7 monoclonal antibody clone MIHI (eBiosciences, CA, USA).

AnnexinV/PI Staining

After co-culture experiment, cell culture samples were collected for analyzing tumor cells apoptosis by AnnexinV-PE/PI staining. The cells were washed and stained with AnnexinV-PE and PI (10 μg/ml) according to manufacturer's instructions (BD Biosciences). The stained cells were analyzed by using flow cytometry on a LSRII. Every group was tested in triplicate.

Early and late apoptotic cells were defined in the population of AnnexinV+/PI−, and AnnexinV+/PI+ cells, respectively, while the necrotic cells were stained with PI+ only. Percent of cell death includes early apoptosis, late apoptosis, and necrotic cells. Flow cytometry data was analyzed by using FlowJo software (Tree Star Inc., OR)

Surface Staining and Intracellular Cytokine Staining of CART Cells

For effector functional analysis, the CART cells were mixed with target cells in an E/:T ratio of 1:1 overnight with the addition of 1.5 μl of FITC-conjugated anti-CD107a Ab. Positive control used T cells (without CAR) stimulated with PMA (1 μg/μl) and Ionomysin (1 ng/μl) for 1 hour. The intracellular cytokines were immobilized after treated with monensin (6 μg/μl) for 6 hours. The samples were then washed, blocked with 10% human and mouse sera for 30 min, stained with anti-CD4 and anti-CD8 Abs for 30 min, fixed and permeabilized with BD Fix/Perm Buffer, stained with anti-IFNγ and anti-IL-2 Abs for 1 hour, and then analyzed by flow cytometry. Data was collected on the BD LSRII flow cytometer and analyzed with Flowjo.

Effector Cytokine Analysis Using Cytokine Bead Array (CBA)

BD CBA™ Human Soluble Protein Flex Set System was used to detect concentrations of cytokines IL-2, IL-6, TNFα and IFNγ in the supernatants collected from the CART cell killing assays on day 1 or 2 of incubation. The CBA system captures a soluble analyte or set of analytes with beads of known size and fluorescence, making it possible to detect analytes using flow cytometry. Each capture bead is coated with an antibody specific for a soluble protein. The detection reagent is a mixture of PE-conjugated antibodies, which provide a fluorescent signal in proportion to the amount of bound analyte. First, 10 tubes of 50 μl set standard dilutions were prepared. Then 50 μl of each unknown sample was added to an assay tube. 50 μl of the mixed capture beads was added to each assay tube and incubated at room temperature for 1 hr. Then 50 μl of the PE detection reagent was added and incubated for 2 hr at room temperature. 1 ml of wash buffer was added to each tube and centrifuged at 200 g for 5 minutes. After the supernatant was removed, 300 μl of wash buffer was added and vortexed prior to acquiring the results on flow cytometer.

Statistical Analysis

All data are presented as mean±SD. The significance of the difference between groups was evaluated by Unpaired Student t-test using Prism software (GraphPad, La Jolla, Calif.). A P value of less than 0.05 was considered statistically significant.

Results

Figure 27A:
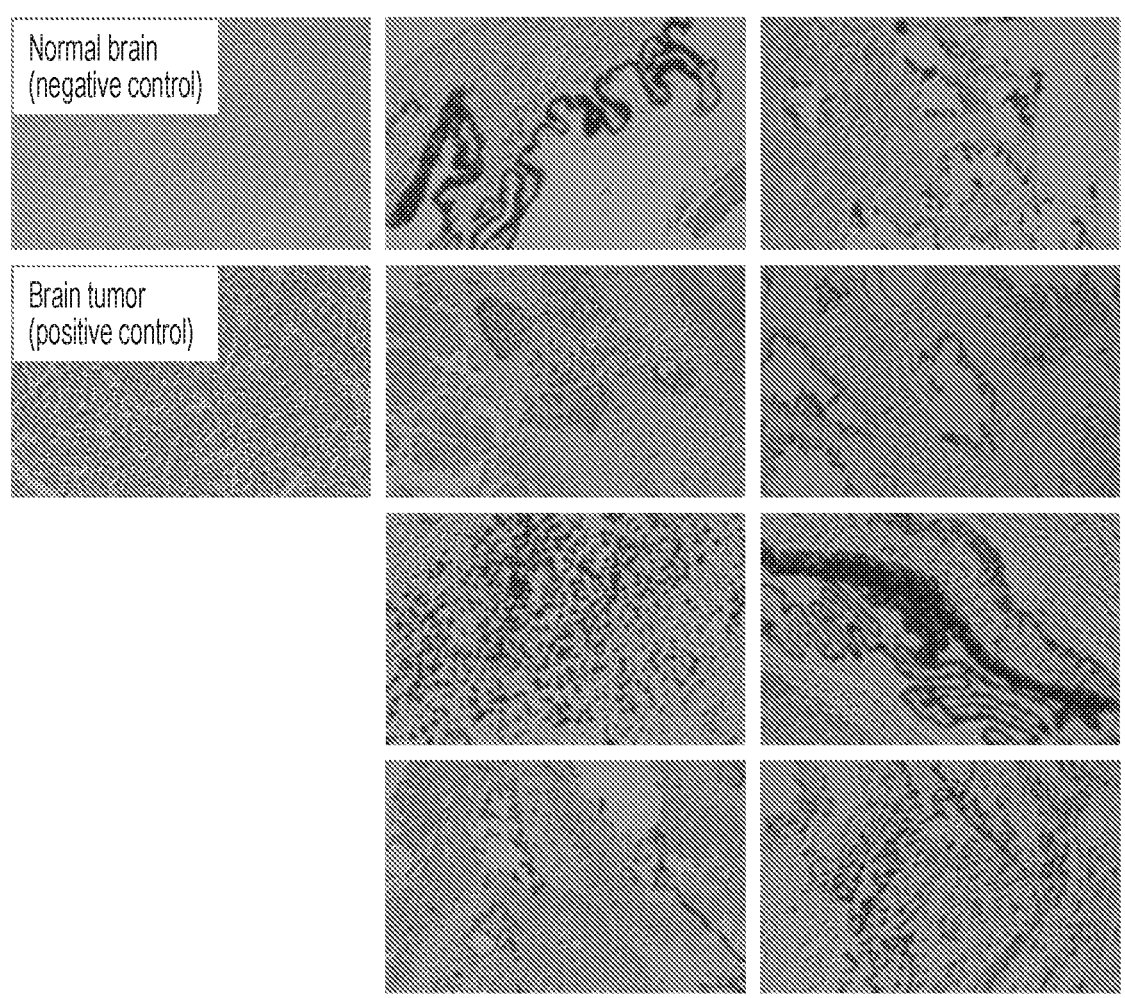
FIG. 27A is a series of photographs that shows immunohistochemistry analyses of GD2 expression in tumor samples from RB patients. Paraffin-embedded retinal tumor samples were stained for GD2 expression by using antibody against human GD2 protein.
Figure 27B:
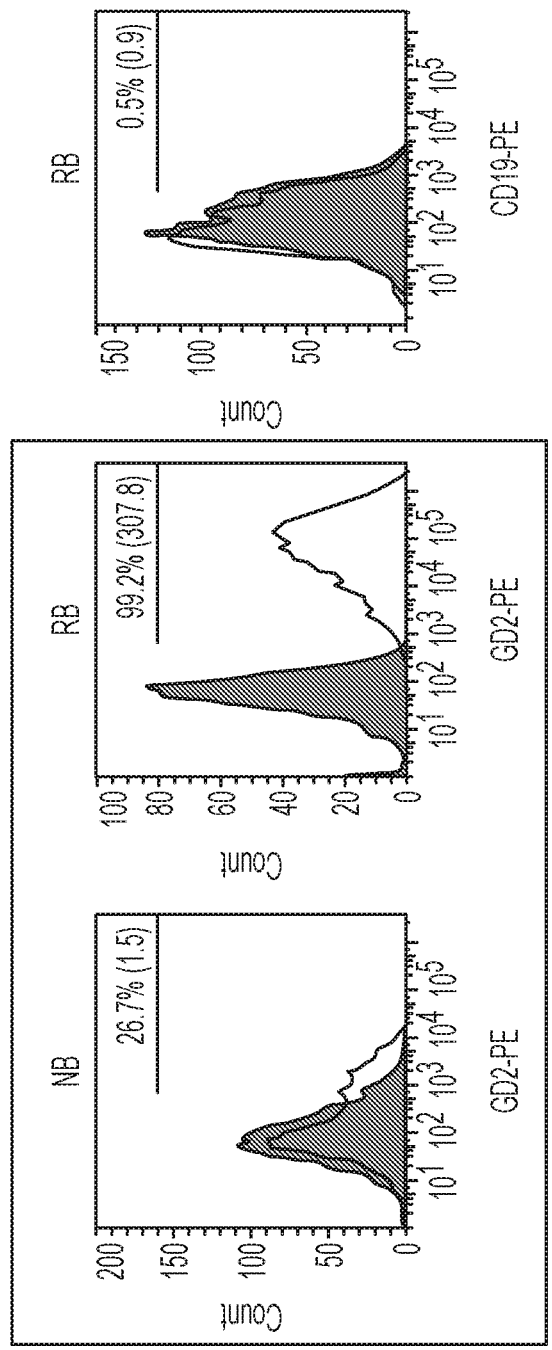
FIG. 27B is a series of graphs that shows surface staining of GD2 expression on Y79 retinoblastoma (RB) cell line. Flow cytometric staining for GD2 and CD19 proteins (black line) or an IgG control (filled histogram) on the surface of Y79 RB cells. Upper right number indicates cell count and the normalized mean fluorescence intensities (nMFI) are shown in parenthesis.

GD2 Protein is Highly Expressed in Retinoblastoma Tumor Samples and Y79 RB Cell Line GD2 is a ganglioside protein that is highly expressed on the cell surface. Retinal tissue sample from eight Rb patients were examined for GD2 expression by using immunohistochemistry. Paraffin-embedded tissues were immunostained with anti-human GD2 antibody and detected by the standard peroxidase enzymatic method. FIG. 27A showed a strong positive signal of GD2 expression in all eight Rb samples and one of brain tumor, while there was no signal in normal brain tissue sample. The expression of GD2 on Y79 retinoblastoma cell line was also investigated by flow cytometry. The results demonstrated that almost 100% of Y79 RB cells expressed GD2 (FIG. 27B). Additionally, low expression of GD2 was found in primary neuroblastoma cells as previously reported. Expression of CD19 protein was not found on Y79 cells and thus the CD19 protein was used as a negative control along with CD19-specific CAR T cells for comparison with the GD2-specific CAR T cells.

Generation of Primary T Cells Expressing GD2-Specific CAR

Figure 28A:
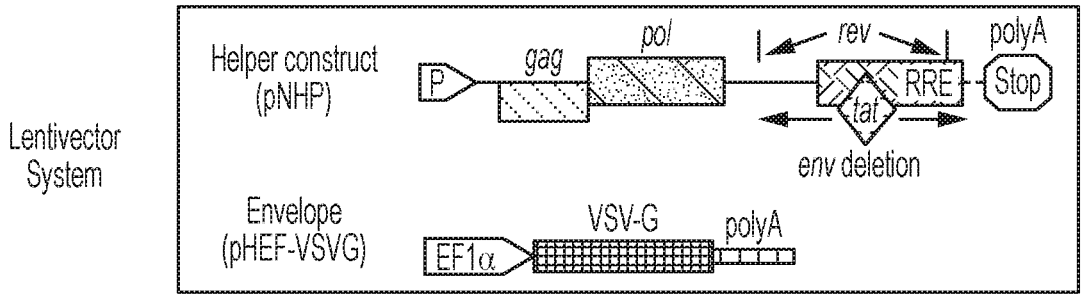
FIG. 28A is a diagram of exemplary GD2 CAR constructs.
Figure 28A:
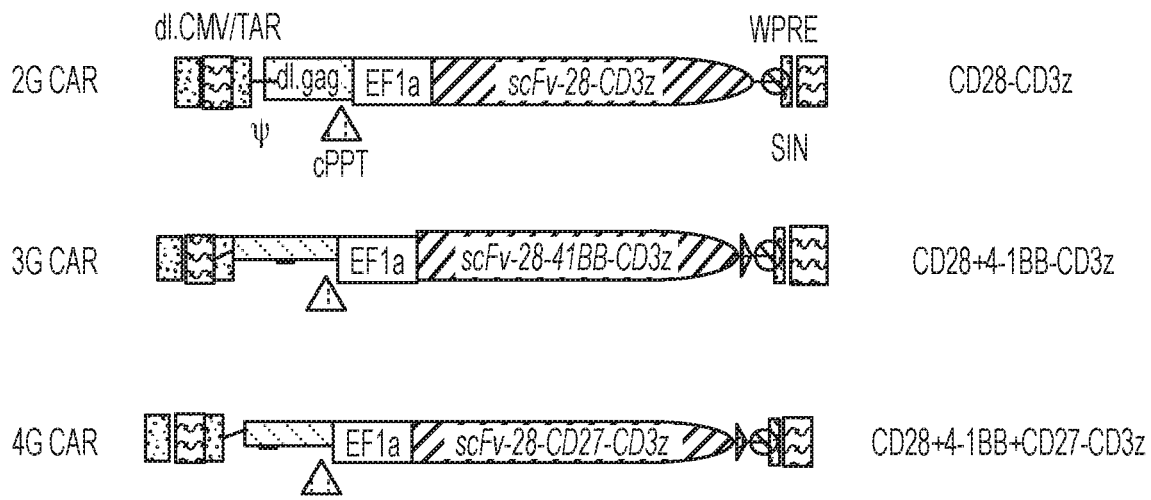
Figure 28A:
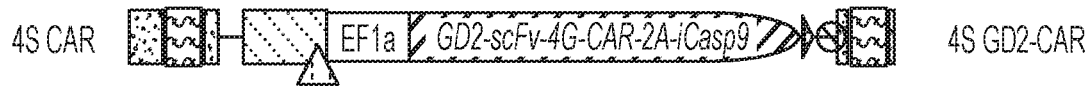

A lentiviral vector was generated encoding a GD2-specific CAR (GD2-CAR), which consisted of (a) anti-GD2 scFv, (b) the hinge and transmembrane regions of the CD8 molecule, (c) the CD28, 4-1BB and CD27 costimulatory signaling moieties, and (d) the cytoplasmic component of CD3ζ molecule (FIG. 28A). Activated lymphocytes from a healthy donor were transduced with lentiviral particles encoding the GD2-CAR or the CD19-CAR, which were used to generate negative control T cells. To determine whether GD2-specific CARs were successfully transferred, the transduced cells were detected for CAR expression on cell surface of T-cells by using antibody. It was found that the CARs were expressed on the T-cells transduced with the lentiviral particles.

Tumor Cell Lysis by GD2-Specific CAR T Cells

Figure 28B:
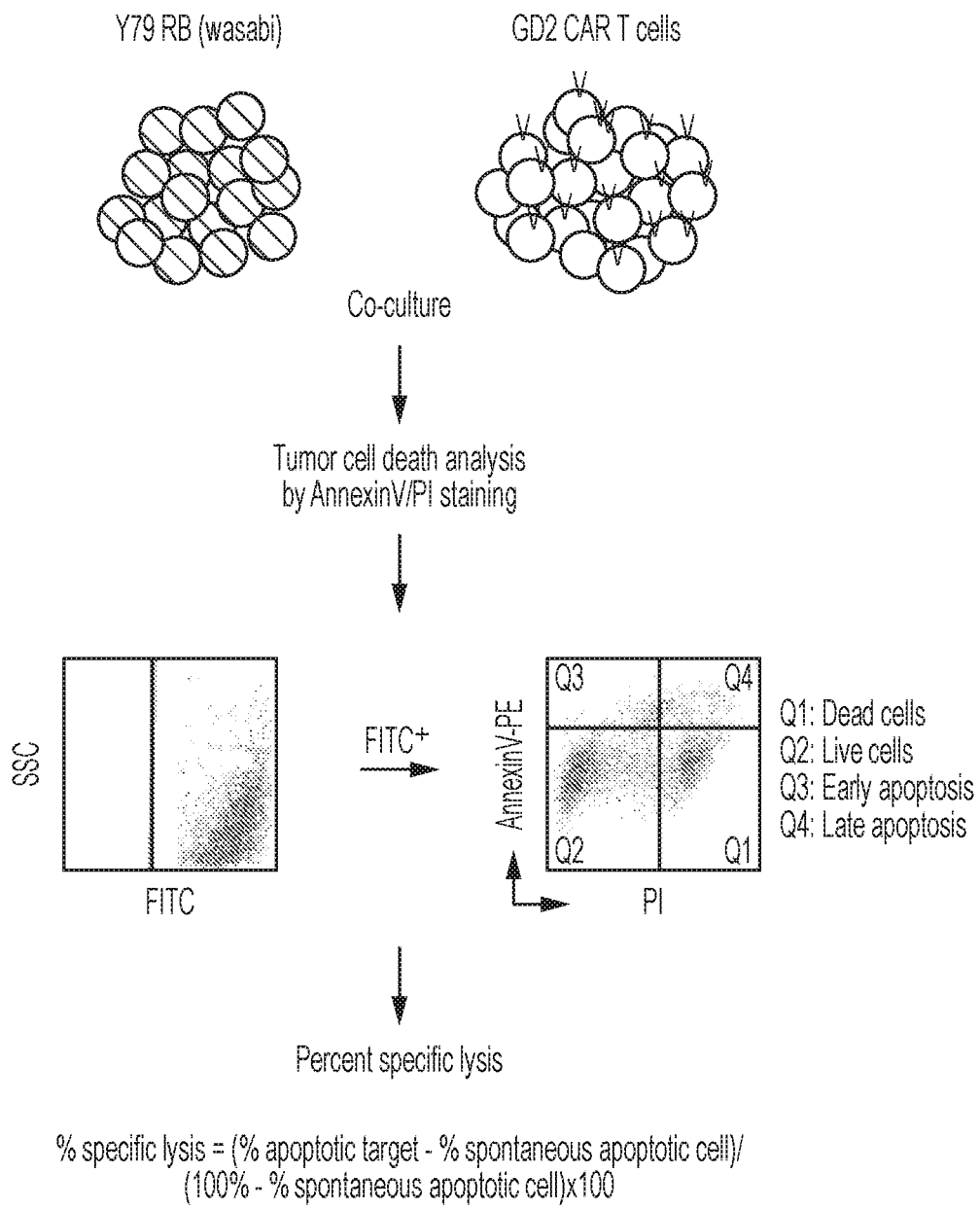
FIG. 28B is a diagram showing an exemplary cell killing assay for RB cells. Y79 RB cells were engineered to express wasort, a green fluorescent protein (GFP), using lentiviral transduction. Y79 RB wasort cells were co-cultured with control T cells or CD19 T cells, or GD2 CAR T cells. After 24 hr of co-cultivation, apoptosis of tumor cells were examined by using AnnexinV/PI staining and analyzed by flow cytometry.
Figure 29A:
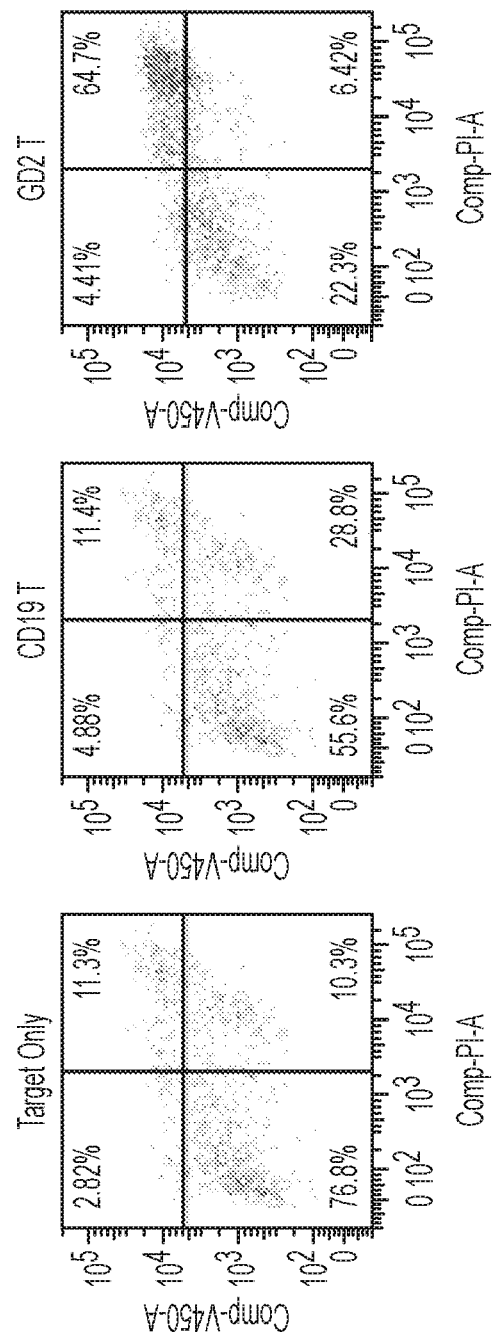
FIGS. 29A-29D show an exemplary short-term killing assay on Y79 RB using CAR T-cells.
Figure 29B:
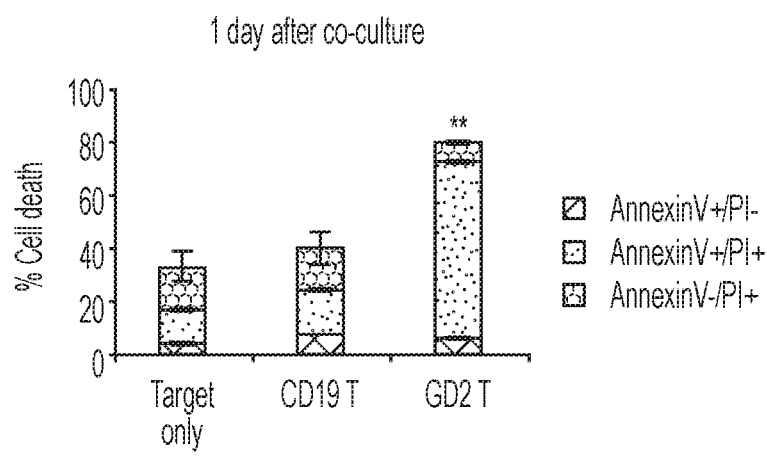
Figure 29C:
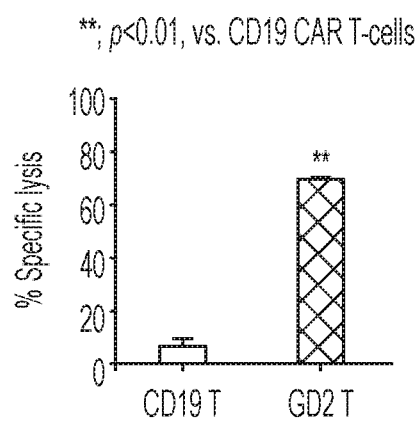
Figure 29D:
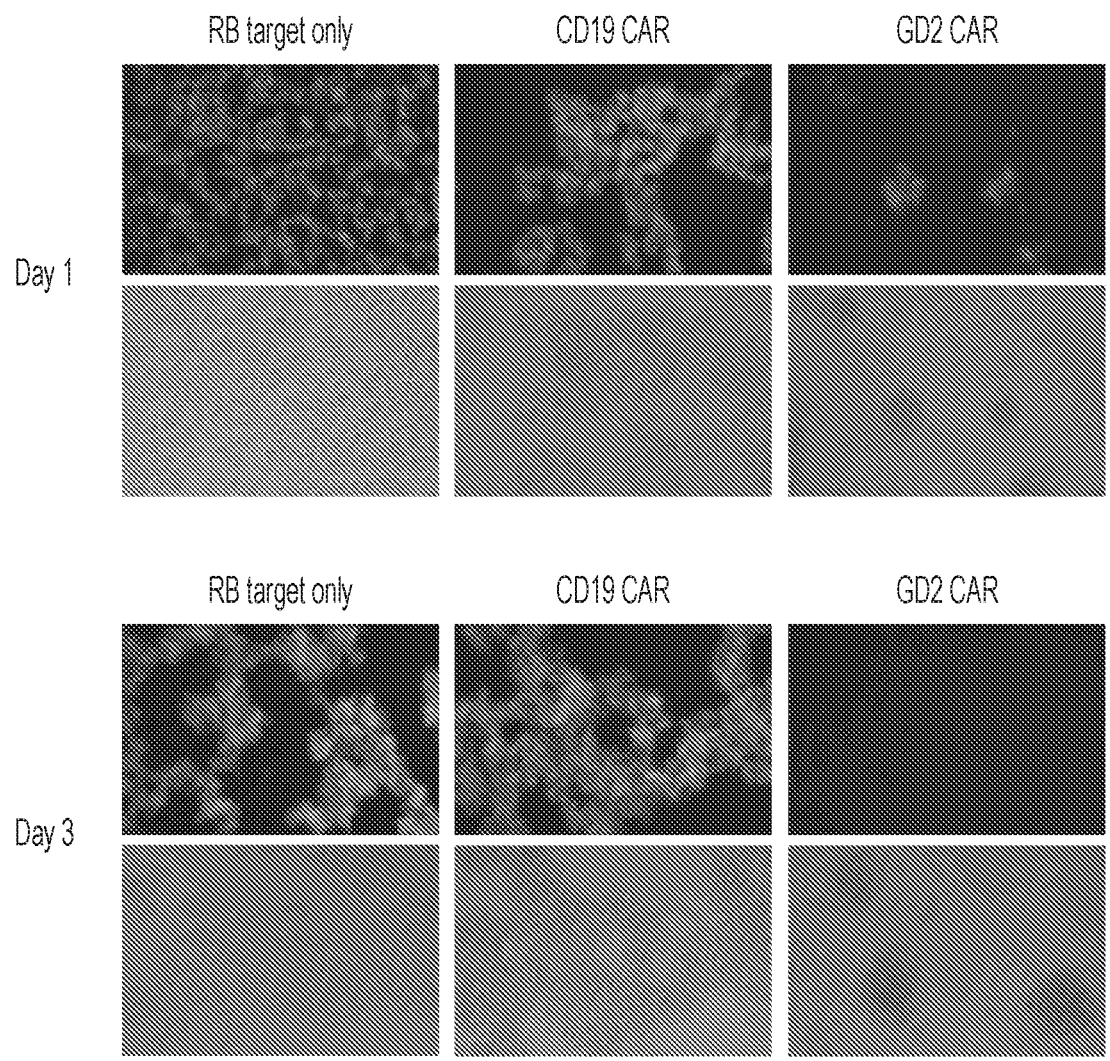
Figure 30:
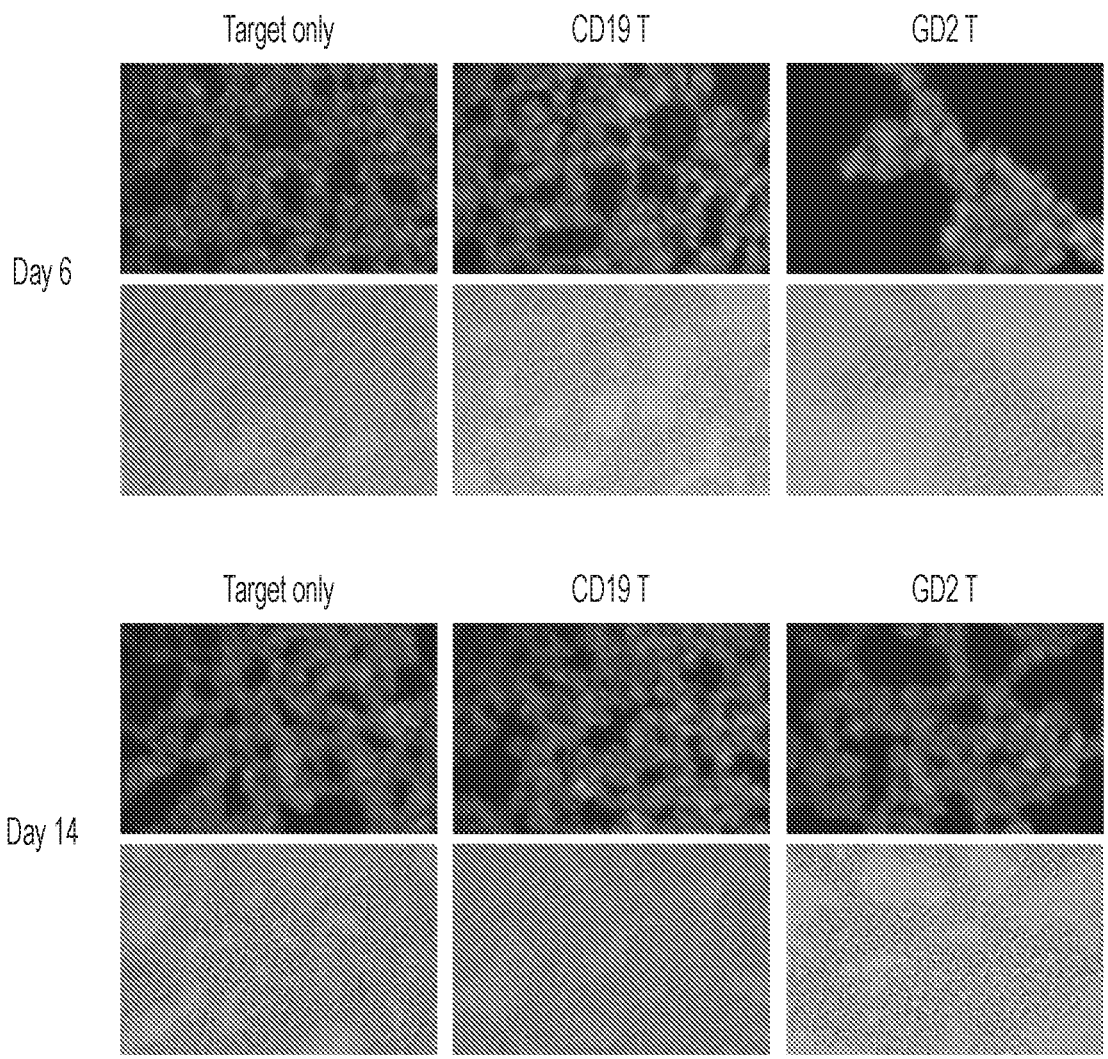
FIG. 30 is a series of photographs that shows exemplary $2^{nd}$ round killing of target RB cells by GD2-CAR T cells at day 6 or day 14 of co-culture.

To test whether GD2-specific CAR T cells could kill the tumor cells, Y79 RB wasort (T) were co-cultured with CD19- or GD2-specific CAR T cells (E). Cell death was analyzed by using AnnexinV/PI staining as demonstrated in schematic diagram FIG. 28B. Co-culture experiment was performed at various E:T ratio to determine killing efficiency of CAR T cells. It was found that GD2-specific CAR T cells induced cell death (FIG. 29A, 29B) and specific lysis of the target cells (FIG. 29C). Killing of target Rb cells was observed both on day 1 of co-culture and day 3 of co-culture with the GD2-CAR T cells (FIG. 29D). Some killing was also observed at day 6 and day 14 of co-culture, although the degree of killing was less than on day 1 or day 3 (FIG. 30). Overall, the GD2-CAR T cells were able to effectively kill the Rb cells.

Figure 31A:
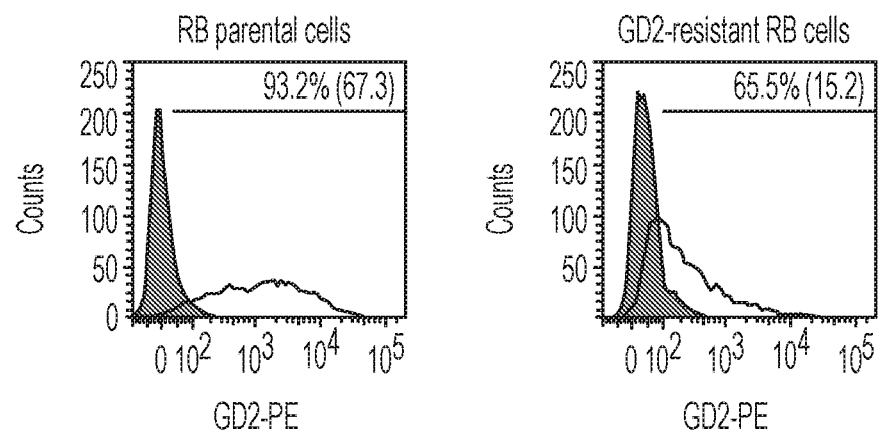
FIGS. 31A and 31B are a series of graphs that show down-regulation of GD2 in RB tumor upon GD2-CAR T targeting.
Figure 31B:
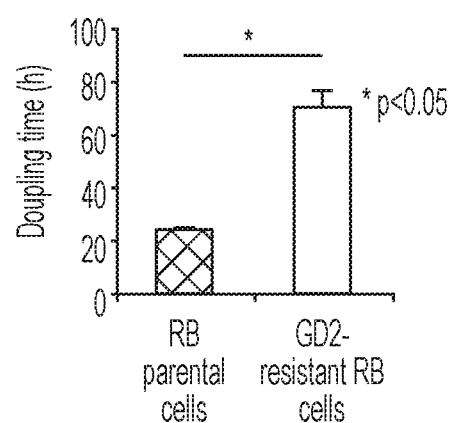
Figures 31C, 31D:
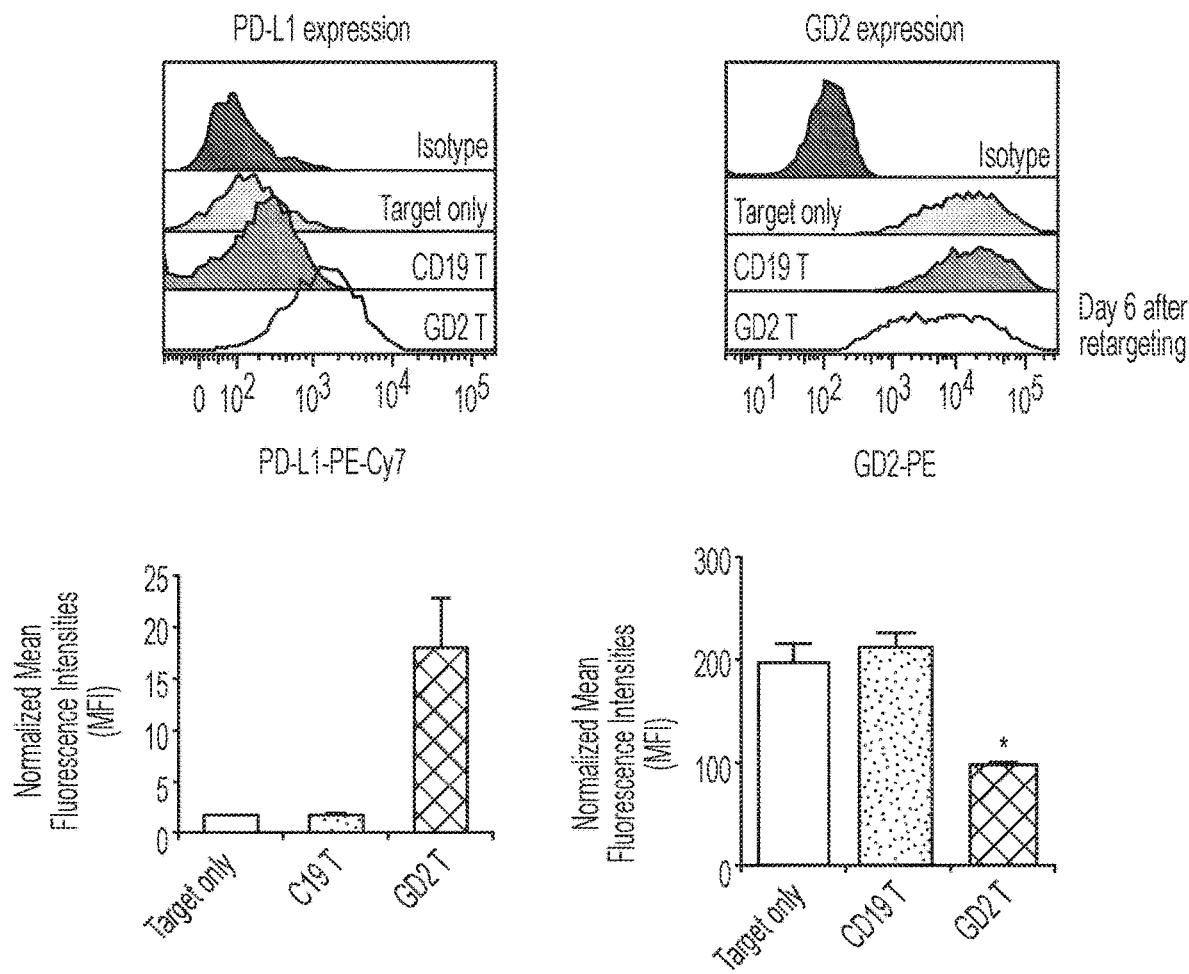
FIG. 31C is a series of graphs that shows upregulation of PD-L1 expression upon GD2-CAR T cell targeting.
FIG. 31D is a series of graphs that shows down-regulation of GD2 expression upon GD2-CAR T cell targeting.

It was determined that GD2 was downregulated in tumor cells upon GD2-CAR T cell co-culture (FIG. 31A) and that GD2-resistant Rb cells developed (FIG. 31B). It was also shown that PD-L1 expression increased upon GD2-CAR T cell co-culture (FIG. 31C). This may indicate that treatment with PD-L1 inhibitors or PD1 inhibitors may increase efficacy of the GD2-CAR T cells. Overall, however, the GD2-CAR T cells were able to effectively kill the Rb cells, indicating that such T cells are useful for treating Rb, either alone or potentially in combination with a PD-L1 or PD1 inhibitor.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A monospecific chimeric antigen receptor (CAR) comprising:
   an antigen binding domain that is monospecific for CD19;
   a transmembrane domain, wherein the transmembrane domain is a CD28 or CD8 transmembrane domain; and
   a cytoplasmic domain containing an interleukin 15-receptor α (IL-15Rα) cytoplasmic domain and a CD3zeta signal transduction domain.

2. The monospecific CAR of claim 1, wherein
   (i) the cytoplasmic domain further comprises a CD27 signaling domain; and/or
   (ii) the antigen binding domain is a single-chain variable fragment (scFv).

3. The monospecific CAR of claim 1, wherein the monospecific CAR further comprises a first spacer between the CD28 transmembrane domain and the IL-15Rα cytoplasmic domain and a second spacer between the IL-15Rα cytoplasmic domain and the CD3zeta signal transduction domain.

4. An immune cell comprising the monospecific CAR of claim 1, wherein the immune cell is a T cell or NK cell.

5. A composition comprising a plurality of the immune cell of claim 4.

6. The monospecific CAR of claim 1, wherein the cytoplasmic domain further comprises a CD28 cytoplasmic domain.

7. The monospecific CAR of claim 6, wherein the CD28 cytoplasmic domain comprises the sequence set forth in SEQ ID NO: 41.

* * * * *